(12) United States Patent
Braun et al.

(10) Patent No.: US 7,432,342 B2
(45) Date of Patent: Oct. 7, 2008

(54) KINASE ANCHOR PROTEIN MUTEINS, PEPTIDES THEREOF AND RELATED DOCUMENTS

(75) Inventors: Andreas Braun, San Diego, CA (US); Charles R. Cantor, Del Mar, CA (US); Stefan M. Kammerer, San Diego, CA (US); Susan Taylor, Del Mar, CA (US); Lora Burns-Hamuro, Somerset, NJ (US); Charles Cook, Mendham, NJ (US); Gary Olson, Moutainside, NJ (US); Christopher Self, West Caldwell, NJ (US)

(73) Assignees: Sequenom, Inc., San Diego, CA (US); The Regents of the University of Califonia, Oakland, CA (US)

( * ) Notice: Subject to any disclaimer, the term of this patent is extended or adjusted under 35 U.S.C. 154(b) by 504 days.

(21) Appl. No.: 10/428,254

(22) Filed: May 1, 2003

(65) Prior Publication Data

US 2003/0232420 A1    Dec. 18, 2003

Related U.S. Application Data

(60) Provisional application No. 60/377,852, filed on May 3, 2002, provisional application No. 60/453,408, filed on Mar. 7, 2003.

(51) Int. Cl.
*C07K 7/08* (2006.01)
*C07K 14/00* (2006.01)

(52) U.S. Cl. .................... 530/324; 530/325; 530/326

(58) Field of Classification Search ..................... None
See application file for complete search history.

(56) References Cited

U.S. PATENT DOCUMENTS

| | | | |
|---|---|---|---|
| 3,645,090 A | 2/1972 | Mochizuki et al. ............. 58/58 |
| 3,687,808 A | 8/1972 | Merigan, Jr. et al. |
| 3,817,837 A | 6/1974 | Rubenstein et al. ....... 195/103.5 |
| 3,850,752 A | 11/1974 | Schuurs et al. ........... 195/103.5 |
| 3,939,350 A | 2/1976 | Kronick et al. .............. 250/365 |
| 3,940,475 A | 2/1976 | Gross ............................ 424/1 |
| 3,996,345 A | 12/1976 | Ullman et al. ................ 424/12 |
| 4,076,982 A | 2/1978 | Ritter et al. |
| 4,179,337 A | 12/1979 | Davis et al. ................. 435/181 |
| 4,275,149 A | 6/1981 | Litman et al. .................. 435/7 |
| 4,277,437 A | 7/1981 | Maggio ........................ 422/61 |
| 4,301,144 A | 11/1981 | Iwashita et al. .............. 424/78 |
| 4,366,241 A | 12/1982 | Tom et al. ...................... 435/7 |
| 4,496,689 A | 1/1985 | Mitra ......................... 525/54.1 |
| 4,511,503 A | 4/1985 | Olson et al. ................. 260/112 |
| 4,562,639 A | 1/1986 | McElroy ...................... 29/584 |
| 4,568,649 A | 2/1986 | Bertoglio-Matte .......... 436/534 |
| 4,640,835 A | 2/1987 | Shimizu et al. ............... 424/94 |
| 4,656,127 A | 4/1987 | Mundy |
| 4,670,417 A | 6/1987 | Iwasaki et al. ................ 514/6 |
| 4,683,195 A | 7/1987 | Mullis et al. .................. 435/6 |
| 4,683,202 A | 7/1987 | Mullis |
| 4,722,848 A | 2/1988 | Paoletti et al. ................ 424/89 |
| 4,791,192 A | 12/1988 | Nakagawa et al. .......... 530/399 |
| 4,826,360 A | 5/1989 | Iwasawa et al. |
| 4,851,018 A | 7/1989 | Lazzari et al. |
| 4,981,957 A | 1/1991 | Lebleu et al. |
| 4,987,071 A | 1/1991 | Cech et al. |
| 4,988,617 A | 1/1991 | Landegren et al. |
| 4,998,617 A | 3/1991 | Ladd, Jr. et al. |
| 5,013,830 A | 5/1991 | Ohtsuka et al. |
| 5,024,939 A | 6/1991 | Gorman ..................... 435/69.1 |
| 5,025,939 A | 6/1991 | Bunn et al. |
| 5,034,506 A | 7/1991 | Summerton et al. |
| 5,082,767 A | 1/1992 | Hatfield et al. ................. 435/6 |
| 5,118,800 A | 6/1992 | Smith et al. |
| 5,118,937 A | 6/1992 | Hillenkamp et al. |
| 5,122,342 A | 6/1992 | McCulloch et al. |
| 5,128,448 A | 7/1992 | Danho et al. ................ 530/329 |
| 5,149,797 A | 9/1992 | Pederson et al. |
| 5,166,315 A | 11/1992 | Summerton et al. |
| 5,175,430 A | 12/1992 | Enke et al. |
| 5,185,444 A | 2/1993 | Summerton et al. |
| 5,214,134 A | 5/1993 | Weis et al. |
| 5,216,141 A | 6/1993 | Benner |
| 5,220,007 A | 6/1993 | Pederson et al. |
| 5,235,033 A | 8/1993 | Summerton et al. |
| 5,247,175 A | 9/1993 | Schoen et al. |
| 5,256,775 A | 10/1993 | Froehler |
| 5,259,044 A | 11/1993 | Isono et al. |
| 5,264,562 A | 11/1993 | Matteucci |
| 5,264,564 A | 11/1993 | Matteucci |
| 5,270,170 A | 12/1993 | Schatz et al. ............... 435/7.37 |
| 5,273,718 A | 12/1993 | Sköld et al. |
| 5,283,173 A | 2/1994 | Fields et al. ................... 435/6 |
| 5,319,080 A | 6/1994 | Leumann |
| 5,338,665 A | 8/1994 | Schatz et al. ................... 435/6 |
| 5,354,934 A | 10/1994 | Pitt et al. ....................... 514/8 |
| 5,363,885 A | 11/1994 | McConnell et al. |
| 5,366,878 A | 11/1994 | Pederson et al. |

(Continued)

FOREIGN PATENT DOCUMENTS

EP    0296781    6/1988

(Continued)

OTHER PUBLICATIONS

Banky, et al., "Related protein-protein interaction modules present drastically different surface topographies despite a conserved helical platform," *J. Mol. Biol.* 330:1117-1129 (2003).

(Continued)

*Primary Examiner*—Rebecca Prouty
(74) *Attorney, Agent, or Firm*—Grant Anderson LLP

(57) ABSTRACT

A-kinase anchor protein (AKAPs) muteins, peptides thereof, and nucleic acids encoding the peptides are provided herein. Also provided are transgenic animals, cells comprising transgenes and various methods employing such peptides.

17 Claims, 2 Drawing Sheets

U.S. PATENT DOCUMENTS

| | | |
|---|---|---|
| 5,393,878 A | 2/1995 | Leumann |
| 5,403,711 A | 4/1995 | Walder et al. |
| 5,405,938 A | 4/1995 | Summerton et al. |
| 5,434,257 A | 7/1995 | Matteucci et al. |
| 5,436,150 A | 7/1995 | Chandrasegaran |
| 5,439,797 A | 8/1995 | Tsien et al. ............... 435/7.21 |
| 5,440,119 A | 8/1995 | Labowsky |
| 5,446,137 A | 8/1995 | Maag et al. |
| 5,453,613 A | 9/1995 | Gray et al. |
| 5,466,677 A | 11/1995 | Baxter et al. |
| 5,466,786 A | 11/1995 | Buhr et al. |
| 5,470,967 A | 11/1995 | Huie et al. |
| 5,474,796 A | 12/1995 | Brennan |
| 5,489,677 A | 2/1996 | Sanghvi et al. |
| 5,491,133 A | 2/1996 | Walder et al. |
| 5,492,806 A | 2/1996 | Drmanac et al. |
| 5,498,545 A | 3/1996 | Vestal |
| 5,503,980 A | 4/1996 | Cantor |
| 5,506,137 A | 4/1996 | Mathur et al. |
| 5,514,785 A | 5/1996 | Van Ness et al. |
| 5,519,134 A | 5/1996 | Acevedo et al. |
| 5,525,464 A | 6/1996 | Drmanac et al. |
| 5,536,649 A | 7/1996 | Fraiser et al. |
| 5,541,307 A | 7/1996 | Cook et al. |
| 5,547,835 A | 8/1996 | Köster |
| 5,561,225 A | 10/1996 | Maddry et al. |
| 5,565,350 A | 10/1996 | Kmiec |
| 5,567,811 A | 10/1996 | Misiura et al. |
| 5,571,676 A | 11/1996 | Shuber |
| 5,576,427 A | 11/1996 | Cook et al. |
| 5,580,732 A | 12/1996 | Grossman et al. |
| 5,591,722 A | 1/1997 | Montgomery et al. |
| 5,593,826 A | 1/1997 | Fung et al. |
| 5,596,086 A | 1/1997 | Matteucci et al. |
| 5,597,909 A | 1/1997 | Urdea et al. |
| 5,602,240 A | 2/1997 | De Mesmaeker et al. |
| 5,604,098 A | 2/1997 | Mead et al. |
| 5,605,798 A | 2/1997 | Köster |
| 5,608,046 A | 3/1997 | Cook et al. |
| 5,610,289 A | 3/1997 | Cook et al. |
| 5,610,300 A | 3/1997 | Altmann et al. |
| 5,618,704 A | 4/1997 | Sanghvi et al. |
| 5,622,824 A | 4/1997 | Köster |
| 5,623,065 A | 4/1997 | Cook et al. |
| 5,623,070 A | 4/1997 | Cook et al. |
| 5,627,053 A | 5/1997 | Usman et al. |
| 5,631,134 A | 5/1997 | Cantor |
| 5,633,360 A | 5/1997 | Bischofberger et al. |
| 5,635,713 A | 6/1997 | Labowsky |
| 5,639,873 A | 6/1997 | Barascut et al. |
| 5,646,265 A | 7/1997 | McGee |
| 5,652,355 A | 7/1997 | Metelev et al. |
| 5,652,356 A | 7/1997 | Agrawal |
| 5,658,873 A | 8/1997 | Bertsch-Frank et al. |
| 5,663,312 A | 9/1997 | Chaturvedula |
| 5,670,633 A | 9/1997 | Cook et al. |
| 5,677,437 A | 10/1997 | Teng et al. |
| 5,677,439 A | 10/1997 | Weis et al. |
| 5,686,656 A | 11/1997 | Amirav et al. |
| 5,691,141 A | 11/1997 | Köster |
| 5,695,940 A | 12/1997 | Drmanac et al. |
| 5,700,672 A | 12/1997 | Mathur et al. |
| 5,700,920 A | 12/1997 | Altmann et al. |
| 5,714,330 A | 2/1998 | Brenner et al. |
| 5,777,324 A | 7/1998 | Hillenkamp |
| 5,786,146 A | 7/1998 | Herman et al. |
| 5,786,464 A | 7/1998 | Seed ..................... 536/23.5 |
| 5,795,714 A | 8/1998 | Cantor et al. |
| 5,807,693 A | 9/1998 | Scott et al. ............... 435/7.21 |
| 5,834,189 A | 11/1998 | Stevens et al. |
| 5,837,832 A | 11/1998 | Chee et al. |
| 5,843,669 A | 12/1998 | Kaiser et al. |
| 5,851,765 A | 12/1998 | Köster |
| 5,853,979 A | 12/1998 | Green et al. |
| 5,856,092 A | 1/1999 | Dale et al. |
| 5,858,659 A | 1/1999 | Sapolsky et al. |
| 5,858,705 A | 1/1999 | Wei et al. |
| 5,869,242 A | 2/1999 | Kamb |
| 5,869,275 A | 2/1999 | Huang ..................... 435/15 |
| 5,871,911 A | 2/1999 | Dahlberg et al. |
| 5,871,945 A | 2/1999 | Lockerbie et al. .......... 435/7.93 |
| 5,872,003 A | 2/1999 | Köster |
| 5,874,283 A | 2/1999 | Harrington et al. |
| 5,876,934 A | 3/1999 | Duthie et al. |
| 5,885,841 A | 3/1999 | Higgs, Jr. et al. |
| 5,888,795 A | 3/1999 | Hamilton |
| 5,900,481 A | 5/1999 | Lough et al. |
| 5,902,723 A | 5/1999 | Dower et al. ................ 435/6 |
| 5,908,755 A | 6/1999 | Kumar et al. |
| 5,912,118 A | 6/1999 | Ansorge et al. |
| 5,925,525 A | 7/1999 | Fodor et al. ................ 435/6 |
| 5,928,870 A | 7/1999 | Lapidus et al. |
| 5,928,906 A | 7/1999 | Köster et al. |
| 5,928,952 A | 7/1999 | Hutchins et al. |
| 5,952,174 A | 9/1999 | Nikiforov et al. |
| 5,952,176 A | 9/1999 | McCarthy et al. |
| 5,975,492 A | 11/1999 | Brenes |
| 5,976,802 A | 11/1999 | Ausorge et al. |
| 5,976,806 A | 11/1999 | Mahajan et al. |
| 5,981,186 A | 11/1999 | Gabe et al. |
| 5,985,214 A | 11/1999 | Stylli et al. |
| 5,998,143 A | 12/1999 | Ellis et al. |
| 6,004,744 A | 12/1999 | Goelet et al. |
| 6,011,013 A | 1/2000 | Carr et al. ................. 514/13 |
| 6,013,431 A | 1/2000 | Söderlund et al. |
| 6,017,693 A | 1/2000 | Yates, III et al. |
| 6,017,702 A | 1/2000 | Lee et al. |
| 6,017,704 A | 1/2000 | Herman et al. |
| 6,018,041 A | 1/2000 | Drmanac et al. |
| 6,020,122 A | 2/2000 | Okasinski et al. .............. 435/5 |
| 6,022,688 A | 2/2000 | Jurinke et al. |
| 6,024,925 A | 2/2000 | Little et al. |
| 6,025,136 A | 2/2000 | Drmanac |
| 6,030,778 A | 2/2000 | Acton et al. |
| 6,043,031 A | 3/2000 | Köster et al. |
| 6,043,136 A | 3/2000 | Jang et al. |
| 6,046,005 A | 4/2000 | Ju et al. |
| 6,054,276 A | 4/2000 | Macevicz |
| 6,059,724 A | 5/2000 | Campbell et al. |
| 6,060,022 A | 5/2000 | Pang et al. |
| 6,074,823 A | 6/2000 | Köster |
| 6,087,095 A | 7/2000 | Rosenthal et al. |
| 6,090,558 A | 7/2000 | Monforte et al. |
| 6,090,606 A | 7/2000 | Kaiser et al. |
| 6,099,553 A | 8/2000 | Hart et al. |
| 6,107,104 A | 8/2000 | Lockerbie et al. ............ 436/578 |
| 6,111,251 A | 8/2000 | Hillenkamp |
| 6,114,148 A | 9/2000 | Seed et al. ............... 435/91.1 |
| 6,117,634 A | 9/2000 | Langmore et al. |
| 6,121,238 A | 9/2000 | Dower et al. ................ 514/13 |
| 6,132,685 A | 10/2000 | Kercso et al. |
| 6,133,436 A | 10/2000 | Köster et al. |
| 6,133,502 A | 10/2000 | Kasuga et al. ............... 800/14 |
| 6,140,053 A | 10/2000 | Köster |
| 6,146,854 A | 11/2000 | Köster et al. |
| 6,147,344 A | 11/2000 | Annis et al. |
| 6,156,501 A | 12/2000 | McGall et al. |
| 6,175,057 B1 | 1/2001 | Mucke et al. ................ 800/12 |
| 6,180,849 B1 | 1/2001 | Streuli et al. ................ 800/18 |
| 6,188,064 B1 | 2/2001 | Koster |
| 6,197,498 B1 | 3/2001 | Köster |
| 6,200,756 B1 | 3/2001 | Herman et al. |
| 6,207,370 B1 | 3/2001 | Little et al. |
| 6,221,601 B1 | 4/2001 | Köster et al. |

| | | | |
|---|---|---|---|
| 6,221,605 B1 | 4/2001 | Köster | |
| 6,225,450 B1 | 5/2001 | Koster | |
| 6,235,478 B1 | 5/2001 | Köster | |
| 6,262,334 B1 | 7/2001 | Endege et al. | |
| 6,265,171 B1 | 7/2001 | Herman et al. | |
| 6,268,131 B1 | 7/2001 | Kang et al. | |
| 6,270,835 B1 | 8/2001 | Hunt et al. | |
| 6,277,573 B1 | 8/2001 | Koster | |
| 6,294,328 B1 | 9/2001 | Fleischmann et al. | |
| 6,300,076 B1 | 10/2001 | Koster | |
| 6,322,970 B1 | 11/2001 | Little et al. | |
| 6,423,966 B2 | 7/2002 | Hillenkamp et al. | |
| 6,428,955 B1 | 8/2002 | Koster et al. | |
| 6,436,635 B1 | 8/2002 | Fu et al. | |
| 6,548,477 B1 | 4/2003 | Olson et al. | 514/2 |
| 6,566,055 B1 | 5/2003 | Monforte et al. | |
| 6,589,485 B2 | 7/2003 | Koster | |
| 6,602,662 B1 | 8/2003 | Koster et al. | |
| 2002/0009394 A1 | 1/2002 | Koster et al. | |
| 2002/0040130 A1 | 4/2002 | Braun | |
| 2002/0042112 A1 | 4/2002 | Koster et al. | |
| 2002/0151493 A1 | 10/2002 | Olson et al. | |
| 2002/0155587 A1 | 10/2002 | Opalsky et al. | |
| 2002/0193298 A1 | 12/2002 | Olson et al. | |
| 2003/0027169 A1 | 2/2003 | Zhang et al. | |
| 2003/0180148 A1 | 9/2003 | Weng | |
| 2003/0180149 A1 | 9/2003 | Koster et al. | |
| 2003/0190644 A1 | 10/2003 | Braun et al. | |
| 2003/0207297 A1 | 11/2003 | Koster et al. | |
| 2003/0232420 A1 | 12/2003 | Braun et al. | |
| 2005/0079521 A1 | 4/2005 | Beaulieu et al. | |

FOREIGN PATENT DOCUMENTS

| | | |
|---|---|---|
| EP | 0299652 | 7/1988 |
| EP | 0395481 | 4/1990 |
| EP | 0596205 | 5/1994 |
| EP | 0613683 | 12/1999 |
| FR | 2650840 A1 | 11/1989 |
| FR | 2749662 | 6/1996 |
| GB | 2329475 | 8/1998 |
| WO | WO 9102087 | 2/1991 |
| WO | WO 9113075 | 9/1991 |
| WO | WO 9116457 | 10/1991 |
| WO | WO 9215712 | 9/1992 |
| WO | WO 9315407 | 8/1993 |
| WO | WO 9321592 | 10/1993 |
| WO | WO 93/25221 | 12/1993 |
| WO | WO 94/17784 | 1/1994 |
| WO | WO 9415219 | 7/1994 |
| WO | WO 9416101 | 7/1994 |
| WO | WO 9421822 | 9/1994 |
| WO | WO 9525281 | 9/1995 |
| WO | WO 95/34326 | 12/1995 |
| WO | WO 9629431 | 9/1996 |
| WO | WO 9632504 | 10/1996 |
| WO | WO 9703210 | 1/1997 |
| WO | WO 9708306 | 3/1997 |
| WO | WO 9737041 | 10/1997 |
| WO | WO 9740462 | 10/1997 |
| WO | WO 9742348 | 11/1997 |
| WO | WO 9743617 | 11/1997 |
| WO | WO 9747974 | 12/1997 |
| WO | WO 9812734 | 3/1998 |
| WO | 98/22122 | 5/1998 |
| WO | WO 9820019 | 5/1998 |
| WO | WO 9820020 | 5/1998 |
| WO | WO 9820166 | 5/1998 |
| WO | WO 9824935 | 6/1998 |
| WO | WO 9830883 | 7/1998 |
| WO | WO 9833808 | 8/1998 |
| WO | WO 9835609 | 8/1998 |
| WO | WO 98/48809 | 11/1998 |
| WO | WO 9856954 | 12/1998 |
| WO | WO 9905323 | 2/1999 |
| WO | WO 9909218 | 2/1999 |
| WO | WO 9912040 | 3/1999 |
| WO | WO 9931278 | 6/1999 |
| WO | WO 9950447 | 10/1999 |
| WO | WO 9954501 | 10/1999 |
| WO | WO 9957318 | 11/1999 |
| WO | WO 0031300 | 6/2000 |
| WO | WO 0051053 | 8/2000 |
| WO | WO 0056446 | 9/2000 |
| WO | WO 0058516 | 10/2000 |
| WO | WO 0058519 | 10/2000 |
| WO | WO 0060361 | 10/2000 |
| WO | 0127857 | 4/2001 |
| WO | 0204489 | 1/2002 |
| WO | 03093296 | 11/2003 |

OTHER PUBLICATIONS

Fayos, et al., "Induction of flexibility through protein-protein interactions," J. Biol. Chem. 278:18581-18587 (2003).

Komives, E. A., NIH Grant 5T32DK007233 "Hemoglobin and Blood Protein chemistry," funding period Jul. 1, 1976-Aug. 31, 2006, pp. 50-179.

Taylor, S. S., NIH Grant 5P01DK54441-03 "PKA and PKC Targeting Mechanisims," funding period Dec. 5, 1998-Jun. 30, 2007, pp. 19-32.

Huang et al., "Identification of a Novel Protein Kinase A Anchoring Protein That Binds Both Type I and Type II Regulatory Subunits", J. Biol. Chem., 272:8057-8064 (1997).

Miki et al., "Single Amino Acids Determine Specificity of Binding of Protein Kinase A Regulatory Subunits by Protein Kinase A Anchoring Proteins", J. Biol. Chem., 274(41):29057-29062 (1999).

Alto N.M., et al., "Bioinformatic design of A-kinase anchoring protein-in silico: A potent and selective peptide antagonist of type II protein kinase A anchoring," PNAS 100:8, Apr. 15, 2003 pp. 4445-4450.

Burns-Hamuro L L, "Designing isoform-specific peptide disruptors of Protein kinase A localization," PNAS 100:7, Apr. 1, 2003, pp. 4072-4077.

Herberg F.W., et al., "Analysis of A-kinase anchoring protein (AKAP) interaction with protein kinase A (PKA) regulatory subunits: PKA isoform specificity in AKAP binding," Journal of Molecular Biology 298:2, Apr. 28, 2000, pp. 329-339.

Huang Lily J-S et al., "D-AKAP2, a novel protein kinase A anchoring protein with a putative RGS domain," PNAS 94:21, Oct. 1997 pp. 11184-11189.

Supplementary European Search Report EP-03-72-6581 (Completed Dec. 4, 2006).

Vijayaraghavan S., et al., "Isolation and Molecular characterization of AKAP110, A Novel, Sperm-Specific Protein Kinase A-Anchoring Protein," Molecular Endocrinology, 13:5, May 1999, pp. 705-717.

Wang Lin et al., "Cloning and mitochondrial localization of full-length D-AKAP2, a protein kinase A anchoring protein" PNAS 98:6, Mar. 13, 2001 pp. 3320-3225.

"Red Tape: It's in You to Give: Last year the Canadian Blood Services' security measures weeded out the 200,000 would-be donors. Doug Fischer looks at the reasons behind the red tape." Ottawa Citizen Saturday Final Edition Oct. 5, 2002.

A Practical Guide To Molecular Cloning, Book: Perbal B., John Wiley & Sons, New York, 1984, Table of contents only.

Aebersold and Mann, Nature 422:198-207 (2003).

Ahern (The Scientist. vol. 9, No. 15, p. 20, Jul. 1995).

Ali et al., "The A kinase anchoring protein is required for mediating the effect of protein kinase A on ROMK1 channels", Proc. Natl. Acad. Sci., 95:10274-10278 (1998).

Altschul et al., "Basic Local Alignment Search Tool", J. Mol. Biol., 215:403-410 (1990).

Amieux et al., "Compensatory Regulation of RI Protein Levels in Protein Kinase A Mutant Mice", J. Biol. Chem., 272(7):3993-3998 (1997).

Angelo et al., "Molecular Characterization of an Anchor Protein (AKAPCE) That Binds the RI Subunit (RCE) of Type I Protein Kinase A from *Caenorhabditis elegans*", J. Biol. Chem., 273(23): 14633-14643 (1998).

Antibodies, Book: A Laboratory Manual, Harlow, E. and Lane D., Cold Spring Harbor Laboratory, 1988, Table of contents only.

Antos et al., Circ. Res., 89:997-1004 (2001).

Araki et al., "Targeted integration of DNA using mutant lox sites in embryonic stem cells", Nucleic Acids Res., 25(4):868-872 (1997).

Amheim et al., Proc. Natl. Acad. Sci. USA, 82:6970-6974 (1985).

Arrand et al., "Different Substrate Specificities of the Two DNA Ligases of Mammalian Cells", J. Biol. Chem., 261(20):9079-9082, (1986).

Badger et al., "New features and enhancements in the X-PLOR computer program", Proteins: Structure, Function, and Genetics, 35(1):25-33, (1999).

Baker et at., "A Scintillation Proximity Assay for UDP-GaINAc:Polypeptide, NAcetylgalactosaminyltransferase," Analytical Biochemistry 239: 20-24 (1996).

Banky et al., "Isoform-specific Difference between the Type I and II Cyclic AMPdependent Protein Kinase Anchoring Domains Revealed by Solution NMR", J. Biol. Chem., 275(45):35146-35152 (2000).

Banky et al., "Dimerizationl Docking Domain of the Type I Regulatory Subunit of cAMP dependent Protein Kinase", J. Biol. Chem., 273(52):35048-35055 (1998).

Bannwarth et al:, "Global Phosphorylation of Peptides Containing Oxidation-Sensitive Amino Acids," Bioorganic & Medicinal Chemistry Letters 6(17): 2141-2146 (1996).

Barradeau et al., "Musle-regulated expression and determinants for neuromuscular junctional localization of the mouse RI regulatory subunit of CAMP-dependent protein kinase", Proc. Natl. Acad. Sci., 98(9):5037-5042 (2001).

Baum et al., "Development of a Scintillation Proximity Assay for Human Cytomegalovirus Protease Using 33Phosphorous," Analytical Biochemistry 237: 129-134 (1996).

Beck et al., "Chemiluminescent detection of DNA: application for DNA sequencing and hybridization", Nucl. Acids Res., 17(13):5115-5123, (1989).

Bertina et al., "Mutation in blood coagulation factor V associated with resistance to activated protein C", Nature, 369:64-67, (1994).

Bessho et al., "Nucleotide excision repair 3' endonuclease XPG stimulates the activity of base excision repair enzyme thymine glycol DNA glycosylase", Nucl. Acids Res., 27(4):79-83, (1999).

Biernat et al., "The construction and cloning of synthetic genes coding for artificial proteins and expression studies to obtain fusion proteins", Protein Engineering, 1(4):345-351, (1997).

Biocomputing, "Informatics and Genome Projects", Smith, W.D. (Ed.), Academic Press, Inc. San Diego, California (1994), Table of contents only.

Biological Techniques Series, Book: "Immunochemical Methods in Cell and Molecular Biology", Mayer, R.J. and Walker, J.H., Academic Press, San Diego, California, 1987, Table of Cont. only.

Bjelland, S. and Seeberg, E., "Purification and characterization of 3-methyladenine DNA glycosylase I from *Escherichia coli*", Nucl. Acids Res., 15(7):2787-2800, (1987).

Bleczinski, C. and Richert, C., "Monitoring the Hybridization of the Components of Oligonucleotide Mixtures to Immobilized DNA via Matrix-assisted Laser Desorption/Ionization Time-of-flight Mass Spectrometry", Rapid Communications in Mass Spectometry, 12:1737-1743, (1998).

Bolin etal., "Peptide and Peptide Mimetic Inhibitors of Antigen Presentation by HLA-DR Class II MHC Molecules. Design, Structure-Activity Relationships, and X-ray Crystal Structures", J. Med. Chem., 43:2135-2148 (2000).

Bosworth et al., "Scintillationproximity assay", Nature, 341:167-168 (1989).

Boudet et al., "UV-treated polystyrene microtitre plates for use in an ELISA to measure antibodies against synthetic peptides", J. Immunolog. Meth., 142:73-82 (1991).

Braun et al., "Detecting CFTR gene mutatiosn by using primer oligo base extension and mass spectrometry", Clin. Chem., 43(7):1151-1158, (1997).

Braun et al., "Improved Analysis of Microsatellites Using Mass Spectrometry", Genomics, 46:18-23, (1997).

Braunwalder et at., "Application of Scintillating Microtiter Plates to Measure Phosphopeptide' Interactions with the GRB2-SH2 Binding Domain," The Journal of Biomolecular Screening 1(1)1:23-26 (1996).

Breen, G., et al., Determining SNP Allele Frequencies in DNA Pools, Biotechniques, (2000). 464-470, 28(3).

Bregman et al., "Molecular Characterization of Bovine Brain P75, a High Affinity Binding Protein for the Regulatory Subunit of CAMP-dependent", J. Biol. Chem., 266(11):7207-7213 (1991).

Brinstar et al., "Expression of a microinjected immunoglobulin gene in the spleen of transgenic mice", Nature, 306:332-336 (1983).

Buetow et al., "High-throughput development and characterization of a genomewide collection of gene-based single nucleotide polymorphism markers by chip-based matrix-assisted laser desorption/ionization time-of-flight mass spectrometry", Proc. Natl. Acad. Sci. USA, 98(2):581-584, (2001).

Burns-Hamuro, L.L., "Using Peptide Arrays to Screen for Isoform-Selective Peptide Disruptors of Protein Kinase A Localization," Meeting Poster presented at the Keystone Symposia on Proteomics: Technologies and Applications (E21, Keystone, Colorado, Mar. 25-30, 2003.

Burton et al., "Type II regulatory subunits are not required for the anchoring-dependent modulation of Ca2+ channel activity by CAMP-dependent protein kinase", Proc. Natl. Acad. Sci. USA 94:11067-11072 (1997).

Cai et al., "Different Discrete Wavelet Transforms Applied to Denoising Analytical Data," J. Chem. Inf. Comput. Sci. 38: 1161-1170 (1998).

Carr et al., "Interaction of the Regulatory Subunit (RII) of CAMP-dependent Protein Kinase with RII-anchoring Proteins occurs through an Amphipathic Helix Binding Motif", J. Biol. Chem., 266(22): 14188-14192 (1991).

Carr et al., "Association of the Type II CAMP-dependent Protein Kinase with a Human Thyroid RII-anchoring Protein", J. Biol. Chem., 267(19):13376-13382 (1992).

Carrillo et al., "The Multiple Sequence Alignment Problem in Biology", SIAM J. App. Math., 48(5): 1073-1082 (1988).

Casey et al., J. Clin. Invest. 106:R31-38 (2000).

Cavalli-Sforza, L.L., "The DNA revolution in population genetics," Trends in Genetics 14(2): 60-65 (1998).

Cech, T.R., "Between the 'RNA World' and the 'Protein World'," Structure 3:969 (1995).

Chaiken et al., "Analysis of Macromolecular Interactions Using Immobilized Ligands," Analytical Biochemistry 201:197-210 (1992).

Chatterji et at., "Cowpea Mosaic Virus: From the Presentation of Antigenic Peptides to the Display of Active Biomaterials", Intervirol., 45:362-370 (2002).

Chen et al., Interaction of Phosphorylated FceRIg Imunoglobulin Receptor Tyrosine Activation Motif-based Peptides with Dual and Single SH2 Domains of p72syk The Journal of Biological Chemistry 271(41):25308-25315 (1996).

Chen et al., "Organelle-specific Targeting of Protein Kinase All (PKAII)", J. Biol. Chem., 272(24):15247-14257 (1997).

Chiu et al., "Mass Spectrometry of Nucleic Acids", Clin. Chem., 45:1578, (1999).

Chiu et al., "Mass Spectrometry of single-stranded restriction fragments captured by an undigested complementary sequence", Nucl. Acids. Res., 28(8):e31 (i-iv), (2000).

Cho-Chung et al., "CAMP-dependent protein kinase: role in normal and malignant growth", Critical Reviews in Oncol./Hematol., 21:33-61 (1995).

Clausen et al., J. Clinical Investigation, 98(5):1195-1209 (1996).

Clegg et al., "Genetic characterization of a brain-specific form of the type I regulatory subunit of CAMP-dependent protein kinase", Proc. Natl. Acad. Sci USA, 85:3703-3707 (1988).

Coghlan et at., "Association of Protein Kinase A and Protein Phosphatase 2B with a Common Anchoring Protein", Science, 267: 108-111 (1995).

Cohen et al., "Emerging Technologies for Sequencing Antisense Oligonucleotides: Capillary Electrophoresis and Mass Spectrometry," Advanced Chromatography, 36:127-162, (1996).
Colledge, M. and Scott, J.D., "AKAPs: from structure to function", Trends in Cell Biology, 9:216-221, (1999).
Collins et al., "A DNA Polymorphism Discovery Resource for Resource for Research on Human Genitic Variation", Genome Research, 8:1229-1231 (1998).
Cong, M. et al., J. Biol. Chem., 276(18):15192-15199 (2001).
Corder et al., "Gene Dose of Apolipoprotein E Type 4 Allele and the Risk of Alzheimer's Disease in Late Onset Families", Science, 261:921-923, (1993).
Costantini, F. and Lacy, E., "Introduction of a rabbit β-globin gene into the mouse germ line", Nature, 294:92-94, (1981).
Cotton et al., "Reactivity of cytosine and thymine in single-base-pair mismatches with hydroxylamine and osmium tetroxide and its application to the study of mutations", Proc. Natl. Acad. Sci. USA, 85:4397-4401, (1988).
Cotton, R.G.H., "Current methods of mutation detection", Mutation Res., 285:125-144, (1993).
Cronin et al., "Cystic fibrosis mutation detection by hybridization to light-generated DNA probe arrays", Hum. Mutat., 7:244-255, (1996).
Culture of Animal Cells, A Manual of Basic Technique, Book: 2nd Edition, Freshney, R.I., Alan R. Liss, Inc., New York, Table of Contents only.
Cummings et al., "Genetically lean mice result from targeted disruption of the RIIb subunit of protein kinase A," Nature 382: 622-626 (1996).
Current Communications in Molecular Biology, Book: Gene Transfer Vectors for Mammalian Cells, Cold Spring Harbor Laboratory, New York, 1987, Table of Contents only.
Cwirla et al., "Peptides on phage: A vast library of peptides for identifying ligands," Proc. Natl. Acad, Sci. USA 87: 6378-6382 (1990).
Dahl, et al., "DNA methylation analysis techniques," Biogerontology, 2003, vol. 4 pp. 233-250; especially pp. 242-245.
Database WPI, Derwent publication # 011635345 citing International Patent Application WO 9747974 of the parent French Patent Application FR 2,749,662.
Devereux et al., "A comprehensive set of sequence analysis programs for the VAX," Nucleic Acids Research 12(1):387-395 (1984).
Diller et al., "Molecular Basis of Regulatory Subunit Diversity in CAMP-Dependent Protein Kinase: Crystal Structure of the Type IIb Regulatory Subunit", Structure, 9:73-82 (2001).
Ding et al., PNAS, 100(6):3059-3064 (2003).
Dittmar, M., "Review of studies of polymorphic blood systems in the Ayrnara indigenous population from Bolivia, Peru, and Chile," Anthropol. Anz. 53(4): 289-315 (1995).
DNA cloning, a practical approach, Book: vol. II, Glover, D.M. (Ed.), IRL Press, Oxford, Washington DC (1985), Table of Contents only.
Dodgson et al., "DNA Marker Technology: A Revolution in Animal Genetics," PoultryScience 76:1108-1114 (1997).
Dostmann et al., "Probing the Cyclic Nucleotide Binding Sites of CAMP-dependent Protein Kinases I and II with Analogs of Adenosine 3',5'-Cyclic Phosphorothioates", J. Biol. Chem., 265(181):10484-10491 (1990).
Dower et al., "Chapter 28. The Search for Molecular Diveristy (11): Recombinant and Synthetic Randomized Peptide Libraries," Annual Reports in Medicinal Chemistry 26:271-280 (1991).
Downes, Kate, et al., SNP allele frequency estimation In DNA pool and variance components analysis, BioTechniques, (2004), 840-846, 36(6). The Wellcome Trust Sanger Institute.
Eck, M.J. and S.R. Sprang, "The Structure of Tumor Necrosis Factor-a at 2.6 A Resolution, Implications for Receptor Binding," The Journal of Biological Chemistry 264(29):17595-17605 (1989).
Edwards et al., "A-kinase anchoring proteins: protein kinase A and beyond", Cur. Opin. Cell Biol., 12:217-221 (2000).
Edwards et al., PCR methods and Applications, 3(4):365-375 (1994).
Eftedal et al., "Consensus sequences for good and poor removal or uracil from double stranded DNA by uracil-DNA glycosylase", Nucl. Acids Res., 21(9):2095-2101, (1993).
Eggertsen et al., Clinical Chemistry 30(10):2125-2129 (1993).

Eichholtz et al., "A Myristoylated Pseudosubstrate Peptide, a Novel Protein Kinase C Inhibitor," J. Biol. Chem., 268:1982-1986 (1993).
Englisch, U. and Gauss, D.H., "Angewandte Chemie", Angew. Chem., 30(6):613-722, (1991).
Evans et al., "Design of Nonpeptidal Ligands for a Peptide Receptor: Cholecystokinin Antagonists," J. Med. Chem. 30:1229-1239 (1987).
Falcioni et al., "Peptidomimetic compounds that inhibit antigen presentation by antoimmune disease-associated class II major histocompatibility molecules", Nature Biotechnol., 17:562-567 (1999).
Fantozzi et al., "Effecf of the Thermostable Protein Kinase Inhibitor on Intracellular Localization of the Catalytic Subunit of CAMP-dependent", J. Biol. Chem., 267(24): 16824-16828 (1992).
Fantozzi et al., "Thermostable Inhibitor of CAMP-dependent Protein Kinase Enhances the Rate of Export of the Kinase Catalytic Subunit from the Nucleus", J. Biol. Chem., 269(4):2676-2686 (1994).
Fauchere, J., "Elements for the Rational Design of Peptide Drugs," Advances in Drug Research 15:29-69 (1986).
Faux, M.C. and Scott, J.D., "More on target with protein phosphorylation: conferring specificity by location", Trends Biochem., 21:312-315, (1996).
Fei et al., Rapid Comm. Mass. Spec., 14(11):950-959 (2000).
Felgner et al., "Lipofection: A highly efficient, lipid-medicated DNA-transfection procedure", Proc. Natl. Acad. Sci. USA, 84:7413-7417 (1987).
Feliciello et al., "The Biological Functions of A-Kinase Anchor Proteins", J. Mol. Biol., 308:99-114 (2001).
Fisher et al., "Surface plasmon resonance based methods for measuring the kinetics and binding affinities of biomolecular interactions", Cur, Opin. Biotechnol., 5:389-395 (1994).
Foster et al., "Naming Names in Human Genetic Variation Research", Genome Research, 8:755-757 (1998).
Frank, R., "Spot-Synthesis: An Easy Technique for the Positionally Addressable, Parallel Chemical Synthesis on a Membrane Support," Tetrahedron, 48(42):9217-9232 (1992).
Fu et al., "A DNA sequencing strategy that requires only five bases of known terminal sequence for priming", Proc. Natl. Acad. Sci. USA, 92:10162-10166, (1995).
Fu et al., "Efficient preparation of short DNA sequence ladders potentially suitable for MALDI-TOF DNA sequencing", Genetic Analysis: Biomolecular Engineering, 12:137-142, (1996).
Fu et al., "Sequencing double-stranded DNA by strand displacement", Nucl. Acids Res., 25(3):677-679, (1997).
Fu et al., "Sequencing Exons 5 to 8 of the p53 Gene by MALDI-TOF Mass Spectrometry", Nature Biotechnol., 16:381-384, (1998).
Gabbita et al., "Decrease in Peptide Methionine Sulfoxide Reductase in Alzheimer's Disease Brain", J. Neurochemistry, 73(4):1660-1666, (1999).
Gante, "Peptidomimetics—Tailored Enzyme Inhibitors," Angew. Chem. Int. Ed. Engl., 33:1699-1720 (1994).
Gasparini et al., "Restriction site generating-polymerase chain reaction (RG-PCR) for the probeless detection of hidden genetic variation: application to the study of some common cystic fibrosis mutations", Mol. Cell. Probes, 6:1-7, (1992).
Genbank Accession AC005730, Oct. 1999.
Genbank Accession AC084019, Oct. 2001.
Genbank Accession AF021833, Sep. 1995.
Genbank Accession AF096289, Mar. 1999.
Genbank Accession AJ242973, Oct. 1999.
Genbank Accession AL646042, Jul. 2007.
Genbank Accession AW195104, Nov. 1999.
Genbank Accession AW874187, May 2000.
Genbank Accession NM007202, Jan. 2003.
Genbank Accession NM-019921, Feb. 2008.
Genbank Accession No. AA331406. Adams et al. "Embryo, 8 week I *Homo sapiens* cDNA." Apr. 21, 1997.
Genbank Accession No. AA349877, Adams et al. "Infant brain *Homo sapiens* cDNA." Apr. 1997.
Genbank Accession No. AF037439, Chatterjee et al. Dec. 1997.
Genbank Accession X86173, Mar. 1996.

Germer, Saren, et al, High-throughput SNP Allele-Frequency Determination In Pooled DNA Samples by Kinetic PCR, Methods, Genome Research, (2000). 258-266, 10, Cold Spring Harbor Laboratory Press.

Gibbs et al., "Detection of single DNA base differences by competitive oligonucleotide priming", Nucl. Acids Res., 17:2437-2448, (1989).

Gilman et al., "A Protein Binding Assay for Adenosine 3':5"-Cyclic Monophosphate", Proc. Natl. Acad. Sci. USA, 67(1):305-312 (1970).

Glantz et al., "Characterization of Distinct Tethering and Intracellular Targeting Domains in AKAP75, a Protein That Links cAMP-dependent Protein Kinase IIβ to the Cytoskeleton", J. Biol. Chem., 268(17):12796-12804, (1993).

Goldmacher et al., Photoactivation of toxin conjugates, Bioconj. Chem. 3:104-107 (1992).

Gonzalez, J.E. and R.Y. Tsien, "Voltage Sensing by Fluorescence Resonance Energy Transfer in Single Cells," Biophysical Journal 69:1272-1280 (1995).

Goueli et al., "A Novel and Simple Method to Assay the Activity of Individual Protein Kinases in a Crude Tissue Extract", Anal. Biochem., 255:10-17 (1995).

Gribskov, M. and Burgess, R.R., "Sigma factors from *E. coli, B. subtilis*, phage SP01, and T4 are homologous proteins", Nucl. Acids Res., 14(16):6745-6763 (1986).

Griffin et al., "Genetic analysis by peptide nucleic acid affinity MALDI-TOF mass spectrometry," Nature Biotechnology, 15:1368-1372, (1997).

Griffin, H.G. and Griffin, A.M., "DNA Sequencing. Recent Innovations and Future Trends", Appl. Biochem. Biotechnol., 38:147-159, (1993).

Guatelli et al., "Isothermal, in vitro amplification of nucleic acids by multienzyme reaction modeled after retroviral replication", Proc. Natl. Acad. Sci. USA, 87:1874-1878, (1990).

Guerrier-Takada et al., "The RNA Moiety of Ribonuclease P Is the Catalytic Subunit of the Enzyme", Cell, 35:849-857, (1983).

Guide To Human Genome Computing Book: Bishop, M.J. (Ed.), Academic Press, San Diego, California (1994), Table of Contents Only.

Hampel et al., "'Hairpin' catalytic RNA model: evidence for helices and sequence requirement for substrate RNA", Nucl. Acids Res., 18(2):299-304, (1990).

Hampel, A. and Tritz, R., "RNA Catalytic Properties of the Minimum (−)s TRSV Sequence", Biochem., 28:4929-4933, (1989).

Hamuro et al., "Domain Organization of D-AKAP2 Revealed by Enhanced Deuterium Exchange-Mass Spectrometry (DXMS)", J. Mol. Biol., 321:703-714 (2002).

Hamuro et al., "Dynamics of cAPK Type II/3 Activation Revealed by Enhanced Amide H/2H Exchange Mass Spectrometry (DXMS)", J. Mol. Biol., 327: 1065-1076 (2003).

Handbook Of Experimental Immunology In Four Volumes, Book: vol. 1, "Immunochemistry", Weir, D.M., (and co-Eds), Fourth Edition, Blackwell Scientific Publications, Osney Mead, Oxford, 1986, Table of contents only.

Harada et al., "Phosphorylation and Inactivation of BAD by Mitochondria-Anchored Protein Kinase A," Molecular Cell 3:413-422 (1999).

Harris et al., Cell Sci., 114:3219-3231 (2001).

Hasan et al., "Base-boronated dinucleotides: synthesis and effect of N7-cyanoborane substitution on the base protons", Nucl. Acids Res., 24(11):2150-2157 (1996).

Hauer et al., "Two well-defined motifs in the CAMP-dependent protein kinase inhibitor (PKIu) correlate with inhibitory and nuclear export function", Protein Sci, 8:545-553 (1999).

Hausken et al., "Mutational Analysis of the A-Kinase Anchoring Protein (AKAP)-binding Site on RII", J. Biol. Chem., 271 (46):29016-29022 (1996).

Hayashi, K., "PCR-SSCP: A Method for Detection of Mutations", Genet. Anal. Tech. Appl. (GATA), 9(3):73-79, (1992).

Hazum et al., "A Photocleavable Protecting Group For The Thiol Function Of Cysteine", Pept., Proc. Eur. Pept. Symp., 16th Brunfeldt, K. (Ed.), pp. 105-110, (1981).

Heaton et al., "Estimation of DNA-sequence diversity in bovine cytokine genes", Mammalian Genome, 12:32-37, (2001).

Herberg et al., "Physiological Inhibitors of the Catalytic Subunit of CAMP-Dependent Protein Kinase: Effect of MgATP on Protein-protein Interactions", Biochem., 32:14015-14022 (1993).

Herman et al., "Methylation-specific PCR: A Novel PCR Assay for Methylation Status of CpG Islands," PNAS 93:9821-9826 (1996).

Herrgard et al., "Domain architecture of a *Caenorhabditis elegans* AKAP suggests a novel AKAP function", FEBS Lett., 486: 107-111 (2000).

Hey, J., "Population genetics and human origins haplotypes are key," Trends in Genetics 14(8): 303-305 (1998) (with reply by L. Cavalli-Sforza).

Higgins et al., "Competitive Oligonucleotide Single-Base Extension Combined with Mass Spectrometric Detection for Mutation Screening", BioTechniques, 23(4):710-714, (1997).

Higgins et al., "DNA-Joining Enzymes: A Review", Methods in Enzymology, 68:50-71, (1979).

Higley, M. and Lloyd, R.S., "Processivity of uracil DNA glycosylase", Mutation Research, DNA Repair, 294:109-116, (1993).

Hinton, Jr. et al., "The application of robotics to fluorometric and isotopic analyses of uranium", Lab. Inf. Manage., 21:223-227, (1993).

Hoogendoorn, Bastiaan, et al, Cheap, accurate and rapid allele frequency estimation of single nucleotide polymorphism by primer extension and DHPLC in DNA pools, Hum Genet (2000) 488-493,107, Pringer-Verlag.

Hruby et al., "Emerging approaches in the molecular design of receptor-selective peptide ligands: conformational, topographical and dynamic considerations," Biochem. J. 268: 249-262 (1990).

Hu, K. and Siddiqui, A., "Regulation of the Hepatitis B Birus Gene Expression by the Enhancer Element I", Virology, 181:721-726, (1991).

Huang et al., "NH2-Terminal Targeting Motifs Direct Dual Specificity A-Kinase anchoring Protein 1 (D-AKAPI) to Either Mitochondria or Endoplasmic Reticulum", J. Cell Biol., 145(5):951-959 (1999).

Hubbard, M.J. and Cohen, P., "On target with a new mechanism for the regulation of protein phosphorylation", Trends Biochem. Sci., 18:172-177, (1993).

Hunenberger et al., "Determinants of Ligand Binding to CAMP-Dependent Protein Kinase", Biochem., 38:2358-2366 (1999).

Ikemoto, S., "Searching for Genetic Markers In the Fields of Forensic Medicine and Human Genetics," N,bpon Hoigaku Zasshi 49(6): 41 9-431 (1 995).

Imaizumi-Scherrer et al., "Type I Protein Kinase A Is Localized to Interphase Microtubules and Strongly Associated with the Mitotic Spindle", Experimental Cell Res., 264:250-265 (2001).

Immobilised cells and enzymes, a practical approach, Woodward, J. (Ed.), IRL Press Limited, Oxford, Washington, DC, 1985, Table of Contents only.

Instrumentation; "Genesis 200/8" (200 cm with including an 8-tip arm) liquid handling systems; Tecan AG of Switzerland ("Tecan"), TECAN Products for Diagnostics and Life Science, located at http://www.tecan.ch/index.htm, Feb. 1999.

Instrumentation; "Model CRS A 255" robot"Digital Servo Gripper""Plate Cube" system."lid parking station""shaker"Robocon Labor-und Indsutrieroboter Ges.m.b.H of Austria ("Robocon"), Sep. 1999.

Instrumentation; "Multimek 96" automated pipettor; Beckman Coulter, Inc. located at http://www.coulter.com, Sep. 8, 1999.

Instrumentation; "Nano-Plotter" from GeSiM, Germany, located at http:/www.gesim.de/np-intro.htm, Sep. 1999.

Instrumentation; Bar code systems, including one and two dimensional bar codes, readable and readable/writable codes and systems; Datalogic S.p.A. of Italy ("Datalogic") located at http://www.datalogic.com, Sep. 1999.

Instrumentation; Dynabeads, streptavidin-coated magnetic beads; from Dynal, Inc. Great Neck, NY and Oslo Norway, 1996.

International Search Report for International Application No. PCT/US00/08111, Date of Mailing Nov. 13, 2000.

IUPAC-IUB Commission on Biochemical Nomenclature: A One-Letter Notation for Amino Acid Sequences, The Journal of Biological Chemistry 243(13):3557-3559 (1968).

Jahnsen et al., "Molecular Cloning, CDNA Structure, and Regulation of the Regulatory Subunit of Type II CAMP-dependent Protein Kinase from Rat Ovarian Granulosa Cells", J. Biol. Chem., 261 (26):12352-12361 (1986).

Jameson, D.M. and W.H. Sawyer, "[12] Fluorescence Anisotropy Applied to Biomolecular Interactions," Methods in Enzymology 246: 283-300 (1995).

Janin, J., "Surface and inside volumes in globular proteins", Nature, 277:491-492 (1979).

Jiang-Baucom et al., "DNA Typing of Human Leukocyte Antigen Sequence Polymorphisms Nucleic Acid Probes and MALDI-TOF Mass Spectometry," Analytical Chemistry, 69:4894-4898, (1997).

Jolley, M.E., "Fluorescence Polarization Assays for the Detection of Proteases and Their Inhibitors," Journal of Biomolecular Screening 1(1):33-38 (1996).

Jurinke et al., "Analysis of Ligase Chain Reaction products via Matrix-Assisted Laser Desorption/Ionization Time-of-Flight-Mass Spectrometry", Anal. Biochem., 237:174-181, (1996).

Jurinke et al., "Application of nested PCR and mass spectrometry for DNA-based virus detection: HBV-DNA detected in the majority of isolated anti-HBc positive sera", Genetic Analysis: Biomolecular Engineering, 14:97-102, (1998).

Jurinke et al., "Detection of hepatitis B virus DNA in serum samples via nested PCR and MALDI-TOF mass spectrometry," Genetic Analysis: Biomolecular Engineering, 13:67-71, (1996).

Jurinke et al., "Detection of RET proto-oncogene codon 634 mutations using mass spectrometry", J. Mol. Med., 75:745-750, (1997).

Jurinke et al., "Recovery of Nucleic Acids from Immobilized Biotin-Streptavidin Complexes Using Ammonium Hydroxide and Applications in MALDI-TOF Mass Spectrometry", Anal. Chem., 69:904-910, (1997).

Kammerer et al., "Amino acid variant in the kinase binding domain of dual-specific A kinase-anchoring protein 2: A disease susceptibility polymorphism", Proc. Natl.Acad.Sci., 100(7):4066-4071(2000).

Kario et al., "Genetic Determinants of Plasma Factor VII Activity in the Japanese", Thromb. Haemost., 73:617-622, (1995).

Kaufman et la., "Evolution of Chromosomal Regions Containing Transfected and Amplified Dihydrofolate Reductase Sequences," Molecular and Cellular Biology 3(4): 699-711 (1983).

Keen et al., "Rapid detection of single base mismatches as heteroduplexes on Hydrolink gels", Trends Genet., 7:5, (1991).

Keown et al., "Methods for Introducing DNA into Mammalian Cells", Meth. Enzynol., 185:527-537 (1990).

Kirk, et al., "Single Mucleotide polymorphism seeking long term association with complex disease," Nucleic Acids Res. 2002, vol. 30, No. 5, pp. 3295-3311.

Kirschner et al., Nat. Genet., 26:89-92 (2000).

Klauck et al., "Coordination of Three Signaling Enzymes by AKAP79, a Mammalian Scaffold Protein", Science, 271:1589-1592 (1996).

Kornher, J.S. and Livak, K.J., "Mutation detection using nucleotide analogs that alter electrophoretic mobility", Nucl. Acids Res., 17:7779-7784, (1989).

Köster et al., "A strategy for rapid and efficient DNA sequencing by mass spectrometry", Nature Biotechnology, 14:1123-1128, (1996).

Köster et al., "Oligonucleotide synthesis and multiple DNA sequencing using chemiluminescent detection", Nucl. Acids Res., Symposium Series No. 24, pp. 318-321, (1991).

Kozal et al., "Extensive polymorphisms observed in HIV-1 clade B protease gene using high-density oligonucleotide arrays", Nature, 2(7):753-759 (1996).

Kramer et al., "Combinatorial Cellulose-Bound Peptide Libraries: Screening Tools for the Identification of Peptides that Bind Ligands with Predefined Specificity," Methods: A Companion' to Methods in Enzymology, 6:388-395 (1994).

Kramer et al., "Spot synthesis: observations and optimizations", J. Peptide Res., 54:319-327 (1999).

Kuppuswamy et al., "Single nucleotide primer extension to detect genetic diseases: Experimental application to hemophilia B (factor IX) and cystic fibrosis genes", Proc. Natl. Acad. Sci. USA, 88:1143-1147, (1991).

Kwoh et al., "Transcription-based amplification system and detection of amplified human immunodeficiency virus type 1 with a bead-based sandwich hybridization format", Proc. Natl. Acad. Sci. USA, 86:1173-1177, (1989).

Kwok (NCBI SNP, ss266958, rs203462, Jun. 30, 2000.

Kyte, J. and Doolittle, R.F., "A Simple Method for Displaying the Hydropathic Character of a Protein", J. Mol. Biol., 157:105-132, (1982).

Lacy et al., "A Foreign β-Globin Gene in Transgenic Mice: Integration at Abnormal Chromosomal Positions and Expression in Inappropriate Tissues", Cell, 34:343-358, (1983).

Laken et al., "Familial colorectal cancer in Ashkenazim due to a hypermutable tract in APC", Nature Genetics, 17:79-83, (1995).

Laken et al., "Genotyping by mass spectrometric analysis of short DNA fragments", Nature Biotechnology, 16:1352-1356 (1998).

Lam et al., "Genetic influence of the R/Q353 genotype on factor VII activity is overwhelmed by environmental factors in Chinese patients with Type II (non-insulin-dependent) dianetes mellitus", Diabetologia, 41:760-766, (1998).

Landegren et al., "A Ligase-Mediated Gene Detection Technique", Science, 241:1077-1080, (1988).

Lasko et al., "Eukaryotic DNA Ligases", Mutation Research, 236:277-287, (1990).

Le Hellard, Stephanie, et al., SNP genotyping on pooled DNA's: comparison of genotyping technologies and a semi automated method for data storage and analysis, Nucleic Acids Research, (2002) 1-10, 30(15), Oxford University Press.

Lee et al., "Isolation of a cDNA clone for the type I regulatory subunit of bovine cAMP-dependent protein kinase", Proc. Natl. Acad. Sci USA, 80:3608-3612 (1983).

Lehman, I.R., "DNA Ligase: Structure, Mechanism, and Function", Science, 186:790-797, (1974).

Leon et al., "A Stable a-Helical Domain at the N Terminus of the RIa Subunits of CAMPdependent Protein Kinase Is a Novel Dimerization/Docking Motif", J. Biol. Chem., 272(45):28431-28437 (1997).

Leon et al., "Probing the Multidomain Structure of the Type I Regulatory Subunit of cAMP-Dependent Protein Kinase Using Mutational Analysis: Role and Environment of Endogenous Tryptophans", Biochem., 39:5662-5672 (2000).

Lerner et al., "High Throughput Screen for Inhibitors of Bacterial DNA Topoisomerase I Using the Scintillation Proximity Assay," Journal of Biomolecular Screening 1(3):135-143 (1996).

Li et al., "Boron-containing oligodeoxyribonucleotide 14mer duplexes: enzymatic synthesis and melting studies", Nucl. Acids Res., 23(21):4495-4501, (1995).

Li et al., "Consequences of CAMP and Catalytic-Subunit Binding on the Flexibility of the A-Kinase Regulatory Subunit", Biochem., 39:15626-15632 (2000).

Li et al., "DNA ligase 1 is associated with the 21 S complex of enzymes for DNA synthesis in HeLa cells", Nucl. Acids Res., 22(4):632-638, (1994).

Li et al., "High-Resolution MALDI Fourier Transform Mass Spectrometry of Oligonucleotides", Anal. Chem., 68(13):2090-2096, (1996).

Li et al., "Identification, Localization, and Function in Steroidogenesis of PAP7: A Peripheral-Type Benzodiazepine Receptor- and PKA (RIa- Associated Protein", Mol. Endocrinol., 15(12):2211-2228 (2001).

Lindahl, T. and Barnes, D.E., "Mammalian DNA Ligases", Annu. Rev. Biochem., 61:251-281, (1992).

Liotta et al., "A Synthetic Tris-Sulfotyrosyl Dodecapeptide analogue of the Insulin Receptor 11 46-Kinase Domain Inhibits Tyrosine Dephosphorylation of the Insulin Receptor in Situ", J. Biol. Chem., 269(37):22996-23001 (1994).

Little et al., "Detection of RET proto-oncogene codon 634 mutations using mass spectrometry," J. Mol. Med., 75:745-750, (1997).

Little et al., "Direct detection of synthetic and biologically generated double-stranded DNA by MALDI-TOF MS," International Journal of Mass Spectrometry and IOn Processes, 169-170:323-330, (1997).

Little et al., "Identification of Apolipoprotein E Polymorphisms Using Temperature Cycled Primer Oligo Base Extension and Mass Spectrometry", Eur. J. Clin. Chem. Clin. Biochem., 35(7):545-548, (1997).

Little et al., "Mass spectrometry from miniaturized arrays for full comparative DNA analysis," Nature Medicine, 3(12):1413-1416, (1997).

Little et al., MALDI on a Chip: Analysis of Arrays of Low-Femtomole to Subfemtomole Quantities of Synthetic Oligonucleotides and DNA Diagnostic Products Dispensed by a Piezoelectric Pipet, Anal. Chem., 69:4540-4546, (1997).

Lizardi et al., "Exponential Amplification of Recombinant-RNA Hybridization Probes", Bio/Technology, 6:1197-1202, (1988).

Luthman, K. and U. Hacksell, "Peptides and Peptidornimetics," Chapter 15 in A Textbook of Drug Design and Development 2nd ed. Krogsgaard-Larsen et al. (Eds.) Australia: Harwood Academic Publishers (1996) pp. 459-485.

Lynch et al., "A Fluorescence Polarization Based Src-Sh2 Binding Assay", Anal. Biochem., 247:77-82 (1997).

Makarova et al., "Generation of Deletion and Point Mutations with One Primer in a Single Clonig Step", Biotech., 29:970-972 (2000).

Manipulating the Mouse Embryo, Book: A Laboratory Manual, Hogan et al., Cold Spring Harbor Laboratory (1986), Table of Contents only.

Marx et al., Science 295:496-499 (2002).

Maxam, A.M. and Gilbert, W., "A new method for sequencing DNA", Proc. Natl. Acad. Sci. USA, 74(2):560-564, (1977).

McCabe et al., Biochem Med. And Metabolic Bio.,44(3):294-295 (1990).

McDonald, T.P., "Thrombopoietin: It's Biology, Clinical Aspects, and Possibilities," The American Journal of Pediatric Hematology/Oncology 14(1):8-21 (1992).

McKnight et al., "Expression of the Chicken Transferrin Gene in Transgenic Mice", Cell, 34:335-341 (1983).

Meinkoth et al., "Signal transduction through the CAMP- dependent protein kinase", Mol. Cell Biochem., 127-1 28:179-186 (1993).

Meinkoth et al., "Dynamics of the distribution of cyclic AMP-dependent protein kinase in living cells", Proc. Natl. Acad. Sci. USA, 87:9595-9599 (1990).

Merrifield et al., "Solid Phase Peptide Synthesis I. The Synthesis of a Tetrapeptide", J. Am. Chem. Soc., 85:2149-2154 (1998).

Methods in Enzymology, "Guide to Protein Purification", Book: vol. 182, Deutscher, M.P. (Ed.), Academic Press, Inc., New York (1990), Table of Contents only.

Methods in Enzymology, "Recombinant DNA", Book: vol. 154, Part E,. Wu, R. and Grossman, L. (Eds.), Academic Press, Inc., New York (1987), Table of Contents only.

Methods in Enzymology, "Recombinant DNA", Book: vol. 155, Part F, Wu, R. (Ed.), Academic Press, Inc., New York (1987), Table of Contents only.

Methods in Molecular Biology. 24, "Computer Analysis of Sequence Data", Book: Part I, Griffin, A.M. and Griffin, H.G. (Eds.), Humana Press, Totowa, New Jersey (1994), Table Contents only.

Mochly-Rosen et al., "Localization of Protein Kinases by Anchoring Proteins: A Theme in Signal Transduction", Science, 268:247-251 (1 995).

Molecular Biology Of The Gene, Book: "General Principles", vol. 1, Fourth Edition, Watson et al., The Benjamin/Cummings Publishing Company, Inc., 1987, Table of Contents only.

Molecular Cloning, a Laboratory Manual, Book: Second Edition, Sambrook, J. and Russell, D.W., Cold Spring Harbor Laboratory Press (1989), Table of Contents only.

Monfardini et al., "A Branched Monomethoxypoly(ethylene glycol) for Protein Modification," Bioconjugate Chemistry 6:62-69 (1995).

Monforte et al., "High-throughput DNA analysis by time-of-flight mass spectrometry," Nature Medicine, 3(3):36-42, (1997).

Moore et al., "Structural Basis for Peptide Binding in Protein Kinase A", J. Biol. Chem., 278(12):10613-10618 (2003).

Morgan et al., "Chapter 26. Approaches to the Discovery of Non-Peptide Ligands for Peptide Receptors and Peptidases", Annual Reports in Medicinal Chemistry, 24:243-252 (1989).

Moskovitz et al., "Overexpression of peptide-methionine sulfoxide reductase in *Saccharomyces cerevisiae* and human T cells provides them with high resistance to oxidative stress", Proc. Natl. Acad. Sci. USA, 95:14071-14075, (1998).

Myers et al., "Detection of Single Base Substitutions by Ribonuclease Cleavage at Mismatches in RNA:DNA Duplexes", Science, 230:1242-1246, (1985).

Myers et al., "Detection of single base substitutions in total genomic DNA", Nature, 313:495-498, (1985).

Myszka et al., "Finetic analysis of macromolecular interations using surface plasmon resonance biosensors," Current Opinion in Biotechnology 8:50-57 (1997).

Naeve et al., "Accuracy of Automated DNA Sequencing: A Multi-Laboratory Comparison of Sequencing Results", Biotechniques, 19(3):448-453, (1995).

Nagamura et al., "Rice molecular genetic map using RFLPs and its applications," Plant Molecular Biology 35: 79-87 (1997).

Nakamaye et al., "Direct sequencing of polymerase chain reaction amplified DNA fragments through the incorporation of deoxynucleoside a-thiothriphosphates", Nucl. Acids Res., 16:9947-9959, (1888).

Narayana et al., "A binary complex of the catalytic subunit of CAMP-dependent protein kinase and adenosine further defines conformational flexibility", Structure, 5(7):921-935 (1997).

Narayana et al., "Crystal Structure of a Polyhistdine-Tagged Recombinant Catalytic Subunit of CAMP-Dependent protein Kinase Complexed with the Petide Inhibitor PKI(5-24) and Adenosine", Biochem., 36(15):4438-4448 (1997).

Needleman et al, "A General Method Applicable to the Search for Similarities in the Amino Acid Sequence of Two Proteins", J. Mol. Biol., 48:443-453 (1970).

Nelson et al., "The Accuracy of Quantification from 1D NMR Spectra Using the PIQABLE Algorithm," Journal of Magnetic Resonance 84: 95-109 (1989).

Newlon et al., "The molecular basis for protein kinase A anchoring revealed by solution NMR," Nature Structural Biology 6(3):222-227 (1999).

Newlon et al., "A novel mechanism of PKA anchoring revealed by solution structures of anchoring complexes," The EMBO Journal 20(7):1651-1662 (2001).

Newton et al., "Analysis of any point mutation in DNA. The amplification refractory mutation system (ARMS)", Nucl. Acids Res., 17:2503-2516, (1989).

Ngai et al., "Protein A antibody-capture ELISA (PACE): and ELISA format to avoid denaturation of surface-adsorbed antigens," Journal of Immunological Methods 158:267-276 (1993).

Nickerson et al., "Automated DNA diagnostics using an ELISA-based oligonucleotide ligation assay", Proc. Natl. Acad. Sci. USA, 87:8923-8927, (1990).

Nilges et al., "Automated NOESY interpretation with ambiguous distance restraints: the refined NMR solution of the pleckstrin homology domain from β-spectrin", J. Mol. Biol., 269:408-422, (1997).

Nollau et al. Clinical Chemistry, vol. 43, No. 7, pp. 1114-1128, 1997.

Nordhoff et al., "Matrix-assisted Laser Desorption/Ionization Mass Spectrometry of Nucleic Acids with Wavelengths in the Ultraviolet and Infrared", Rapid Comm. Mass Spectrom., 6:771-776, (1992).

Nucleases, Book: 2nd Edition, Linn, S.M, et al. (Eds.), Cold Spring Harbor Laboratory Press (1993), Table of Contents only.

Nucleic acid hybridisation, a practical approach, Book: Hames, B.D. and Higgins, S.J. (Eds.), IRL Press, Oxford, Washington DC (1985), Chapter 2, pp. 17-34.

Nyréet al., "Solid phase DNA minisequencing by an enzymatic luminometric inorganic pyrophosphate detection assay", Anal. Biochem., 208:171-175, (1993).

O'Brian et al., "N-MYRISTYL-Lys-Arg-Thr-Leu-Arg: A novel protein kinase C inhibitor", Biochem. Pharmacol., 39(1):49-57 (1990).

Oligonucleotides and Analogues, a practical appraoch, Book: Protocol 8. "Synthesis of 3',5'-O-(tetraisopropyldisiloxane-1,3-diyl)-N4-isobutyryl-2'-O-methylcytidine (compound 8); mol. wt 569.85", Eckstein, F. (Ed.), Oxford University Press, New York, pp. 56-57; Chapter 6, "Synthesis of oligo-2'-deoxyribonucleoside methylphosphonates", pp. 137-139; and pp. 256-259, (1991).

Oligonucleotides synthesis, a practical approach, Book: Gait, M.J. (Ed.), IRL Press, Oxford, Washington DC (1984), Table of Contents only.

Olson et al., "Concepts and Progress in the Development of Peptide Mimetics", J, Med. Chem., 36(21):3039-3049 (1993).

Olson et al., "Peptide Mimetics of Thyrotropin-Releasing Hormone Based on a Cyclohexane Framework: Design, Synthesis, and Cognition-Enhancing Properties", J. Med. Chem., 3:2866-2879 (1995).

Orita et al., "Detection of polymorphisms of human DNA by gel electrophoresis as single-strand conformation polymorphisms", Proc. Natl. Acad Sci. USA, 86:2766-2770, (1989).

O'Shannessy et al., "Determination of kinetic rate and equilibrium binding constants for macromolecular interactions: a critique of the surface plasmon resonance literature," Current Opinion in Biotechnology 5:65-71 (1994).

Palmiter et al., "Differential Regulation of Metallothionein-Thymidine Kinase Fusion Genes in Transgenic Mice and Their Offspring", Cell, 29:701-710 (1982).

Palmiter et al., "Dramatic growth of mice that develop from eggs microinjected with metallothionein-growth hormone fusion genes", Nature 300:611-615 (1982).

Palmiter et al., "Matallothionein-human GH fusion genes stimulate growth of mice", Science, 222:809-814, (1983).

Paterson, A.H., "Molecular Dissection of Quantitative Traits: Progress and Prospects," Genome Research 321-333 (1995).

Pearson, R.B. and Kemp, B.E., "Protein Kinase Phosphorylation Site Sequences and Consensus Specificity Motifs: Tabulations", Meth. Enzymol., 200:62-81, (1991).

Pearson, W.R. and Lipman, D.J., "Improved toos for biological sequence comparison", Proc. Natl. Acad. Sci. USA, 85:2444-2448,(1988).

Pena et al., "DNA diagnosis of human genetic individuality," J. Mol. Med. 73: 555-564 (1995).

Perkins et al., "PKA, PKC, and AKAP localization in and around the neuromuscular junction", BMC Neurosci., 2:17 (2001).

Perrotta, A.T. and Been, M.D., "Cleavage of Oligoribonucleotides by a Ribozyme Derived from the Hepatitis d Virus RNA Sequence", Biochem., 31:16-21, (1992).

Podhajska, A.J. and Szybalski, W., "Conversion of the FokI endonuclease to a universal restriction enzyme: cleavage of phage M13mp7 DNA at predetermined sites", Gene, 40:175-182, (1985).

Polettini et al., "Fully-automated systematic toxicological analysis of drugs, poisons, and metabolites in whole blood, urine, and plasma by gas chromatography—full scan mass spectrometry," Journal of Chromatography B 713:265-279 (1998).

Porter et al., "N1-Cyanoborane_2'-Triphosphate Is a Good Substrate for DNA Polymerase", Biochem., 34:11963-11969, (1995).

Prezant, T.R. and Fischel-Ghodsian, N., "Trapped-Oligonucleotide Nucleotide Incorporation (TONI) Assay, a Simple Method for Screening Point Mutations", Human Mutation, 1:159-164, (1992).

Prosser, J., "Detecting single-base mutations", TIBTECH, 11:238-246, (1993).

Pruslin et al., "Caveats and suggestoins for the ELISA," Journal of Immunological Methods 137:27-35 (1991).

Reinitz et al., Arch. Biochem. Biophys., 348:391-402 (1997).

Reymer et al., "A lipoprotein lipase mutation (Asn291Ser) is associated with reduced HDL cholesterol levels in premature atherosclerosis", Nature Genetics, 10:28-34, (1995).

Risch, Neil, et al., The Relative Power of Family-Based and Case Control Design of Linkage Disequilibrium Studies of Complex Human Diseases I. DNA Pooling. Genome Research, (1998), 1273-1288, 8, Cold Spring Harbor Laboratory Press.

Rizo, J and L.M. Gierasch, "Constrained Peptides: Models of Bioactive Peptides and Protein Substructures," Annu. Rev. Biochem. 61: 387-418 (1992).

Roberts, D.C. and F. Vallaccio, "Unusual Amino Acids in Peptide Synthesis," in The Peptides, 5(6):341-449 (1983).

Robinson et al., Arch. Biochem. Biophys., 330:181-187 (1996).

Roemer etal., "Knock-In And Knock-Out", New Biol., 3:331-335 (1991).

Rose et al., "Hydrophobicity of Amino Acid Residues in Globular Proteins", Science, 229:834-838 (1985).

Rosenbaum, V. and Riesner, D., "Temperature-gradient gel electrophoresis. Thermodynamic analysis of nucleic acids and proteins in purified form and in cellular extracts", Biophy. Chem., 26:235-246, (1987).

Roses (Annals of the New York Academy of Sciences (1998) vol. 855, pp. 738-743.

Ross et al., "Analysis of Short Tandem Repeat Polymorphisms in Human DNA by Matrix-Assisted Laser Desorption/IOnization Mass Spectrometry," Analytical Chemistry, 69:3966-3972, (1997).

Ross et al., "Discrimination of Single-Nucleotide Polymorphisms in Human DNA Using Peptide Nucleic Acid Probes Detected by MALDI-TOF Mass Spectrometry," Analytical Chemistry, 69:4197-4202, (1997).

Ross, Phillp, et al., Quantitative Approach to Single Nucleotide Polymorphism Analysis Using MALDI-TOF Mass Spectrometry, BioTechniques, (2000) 620-629, 29(3).

Rossi et al., "Ribozymes as Anti-HIV-1 Therapeutic Agents: Principles, Applications, and Problems", Aids Res. and Human Retroviruses, 8(2):183-189, (1992).

Ruppert et al., "A Filtration Method for Plasmid Isolation Using Microtiter Filter Plates", Anal. Biochem., 230:130-134, (1995).

Saiki et al., "Analysis of enzymatically amplified β-globin and HLA-DQa DNA with allele-specific oligonucleotide probes", Nature, 324:163-166, (1986).

Saleeba, J.A. and Cotton, R.G.H., "Chemical Cleavage of Mismatch to Detect Mutations", Meth. Enzymol., 217:286-295, (1993).

Samson et al., "Resistance to HIV-1 infection in caucasian individuals bearing mutant alleles of the CCR-5 chemokine receptor gene", Nature, 382:722-725, (1996).

Sanger et al., "DNA sequencing with chain-terminating inhibitors", Proc. Natl. Acad. Sci. USA, 74(12):5463-5467, (1977).

Sanghvi, Y.S., Book: Antisense Research and Applications, Chapter 15, "Heterocyclic Base Modifications In Nucleic Acids and Their Applications In Antisense Oligonucleotides", S.T. Crooke et al. (Eds. ), CRC Press, Inc., Florida, 1993, pp. 273-288.

Saparbaev et al., "*Escherichia coli, Saccharomyces cerevisiae*, rat and human 3-methyladenine DNA glycosylases repair 1, N6-ethenoadenine when present in DNA", Nucl. Acids Res., 23(18):3750-3755, (1995).

Sarabu et al., "Oxazole- and Imidazole- Based Ser-Lau Dipeptide Mimetics in Potent Inhibitors of Antigen Presentation by MHC Class II DR Molecules," Drug Design and Discovery, 18(1):3-7 (2002).

Sarin et al., "Inhibition of acquired immunodeficiency syndrome virus by oligodeoxy-nucleoside methylphosphonates", Proc. Natl. Acad. Sci. USA, 85:7448-7451, (1988).

Sasaki, Tomonari, et al., Precise Estimation of Allele Frequencies of Single Nucleotide Polymorphisms by a Quantitative SSCP Analysis of Pooled DNA, Am. J. Hum, Genet (2001), 214-218, 68, The American Society of Human Genetics.

Schächter et al., "Genetic associations with human longevity at the APOE and ACE loci", Nature Genetics, 6:29-32, (1994).

Schillace et al., "Organization of kinases, phosphatases, and receptor signaling complexes", J. Clin. Invest., 103(61):761-765 (1999).

Schwartz, R.M. and M.O. Dayhoff, "23:Matrices for Detecting Distant Relationships," Atlas of Protein Science and Structure National Biomedical Research Foundation, pp. 353-358 (1979).

Scopes, R.K., Book: Protein Purification, Principles and Practice, Springer-Verlag, New York, (1982), Table of Contents only.

Scott et al., "Cyclic Nucleotide-Dependent Protein Kinases," Pharmac. Ther. 50:123-145 (1991).

Scott et al., "Type II Regulatory Subunit Dimerization Determines the Subcellular Localization of the CAMP-dependent Protein Kinases," The Journal of Biological Chemistry 265:21561-21566 (1990).

Senko et al., "Automated Assignment of Charge States from Resolved Isotopic Peaks for Multiply Charged Ions", J. Am. Soc. Mass Spectrom, 6:52-56, (1995).

Senter et al., "Novel photocleavable protein crosslinking reagents and their use in the preparation of antibody-toxin conjugates", Photochem. Photobiol., 42:231-237, (1985).

Sequence Analysis in Molecular Biology, Book: Treasure Trove or Trivial Pursuit, von Heijne, G., Academic Press, Inc., New York, 1987, Table of Contents only.

Sequence Analysis Primer, Book: Gribskov M, and Devereux, J. (Eds.), W.H. Freeman and Company, New York, 1992, Table of Contents only.

Sequenom Advances the Industrial Genomics Revolution with the Launch of Its DNA MassArrayÒAutomated Process Line, Press Release: Sep. 28, 1998, http://www.sequenom.com/pressrelease.htm.

Sequenom and Gemini Identify Genes Linked to Cardiovascular Disease, Press Release: Nov. 28, 2000, http://www/sequenom.com/ir/ir_prs.asp.

Sequenom Announces Publication of Results From Large-Scale SNP Study With the National Cancer Institute, Press Release: Jan. 16, 2001, http://www/sequenom.com/ir/ir_prs.asp.

Sequenom Completes Design of More Than 400,000 SNP Assays; Mass EXTENDTM Assay Portfolio Covers Majority of SNPs in the Public Domain, Press Release; Oct. 10, 2000, http://www/sequenom.com/ir/ir_prs.asp.

Sequenom: Technologies and Tools, located at http://www.sequenom-san.com/tech/tools.html, dated Aug. 29, 1999.

Shih, M. et al., J. Biol. Chem., 274(3):1588-1595 (1999).

Zhou, Guo-Hua et al., Quantitative detection of single nucleotide polymorphisms for a pooled sample by a bioluminometric assay coupled with modified primer extension reaction (BAMPER), Nucleic Acids Research, (2001) 1-11, 29(19 e93), Oxford University Press.

Shriver et al., "Ethnic-Affiliation Estimation by Use of Population-Specific DNA Markers", Am. J. Hum. Genet., 60:957-964 (1997).

Siegert et al., "Matrix-Assisted Laser desorption/Ionization Time-of-Flight Mass Spectrometry for the detection of Polymerase Chain Reaction Containing 7-Deazapurine Moieties", Anal. Biochem., 243:55-65, (1996).

Silverman et al., "New assay technologies for high-throughput screening," Current Opinion in Chemical Biology 2:397-403 (1998).

Siow et al., "Effects of Vasoactive Intestinal Peptide on Human Sperm Motility", Archives of Andrology, 43(1):67-71 (1999).

Sittampalam et al., "High-throughput screening: advances in assay technologies," Current Opinion in Chemical Biology 1:384-391 (1997).

Skalhegg et al., "Location of CAMP-Dependent Protein Kinase Type I with the TCR-CD3 Complex," Science 263:84-87 (1994).

Smith et al., "Comparison of Biosequences," Advances in Applied Mathematics 2:482-489 (1981).

Smith, D.B. and Johnson, K.S., "Single-step purification of polypeptides expressed in *Escherichia coli* as fusions with glutathione S-transferase", Gene, 67:31-40, (1988).

Smith, L.M., "Sequence from spectrometry: A realistic prospect", Nature Biotechnology, 14:1084-1085, (1996).

Snapir, A. et al., Clin.Sci., 104:509-520 (2003).

Sokolov, B.P., "Primer extension technique for the detection of single nucleotide in genomic DNA", Nucl. Acids Res., 18(12):3671, (1989).

Sonatore et al., "The Utility of FK506-Binding Protein as a Fusion Partner in Scintillation Proximity Assays: Application to SH2 Domains," Analytical Biochemistry 240:289-297 (1996).

Srinivasan et al., "Matrix-assisted Laser Desorption/Ionization Time-of-flight Mass Spectrometry as a Rapid Screening Method to Detect Mutations Causing Tay-Sachs Disease," Rapid Communications in Mass Spectrometry, 11:1144-1150, (1997).

Stein et al., "Physicochemical properties of phosphorothioate oligodeoxynucleotides", Nucl. Acads Res., 16:3209-3221, (1988).

Steward et al., "Human β-Globin Gene Sequence Injected into Mouse Eggs, Retained in Adults, and Transmitted to Progeny", Science, 217:1046-1048, (1982).

Stillman, B.W. and Gluzman, Y., "Replication and Supercoiling of Simian Virus 40 DNA in Cell Extracts from Human Cells", Mol. Cell. Biol., 5(8):2051-2060, (1985).

Storm, Methods Mol. Biol., 212:241-262 (2003).

Sugisaki, H. and Kanazawa, S., "New restriction endonucleases from *Flavobacterium okeanokoites* (FokI) and *Micrococcus luteus* (Mlu1)", Gene, 16:73-78, (1981).

Sullivan et al., "Development of a Scintillation Proximity Assay for Calcineurin Phosphate Activity," Journal of Biomolecular Screening 2(1):19-23 (1997).

Surface Plasmon Resonance-BIAcore, http://www.med.unc.edu/wrkunits/2depts/biochem/MACINFAC/biacore.html (accessed on Nov. 26, 2003).

Syvänen et al., "A Primer-Guided Nucleotide Incorporation Assay in the Genotyping of Apolipoprotein E", Genomics, 8:684-692, (1990).

Syvänen et al., "Identification of Individuals by analysis of Biallelic DNA markers, using PCR and Solid-Phase Minisequencing", Am. J. Hum. Genet., 52:46-59, (1993).

Szabo et al., "Surface plasmon resonance and its use in biomolecular interaction analysis," Current Opinion in Structural Biology, 5(5):699-705 (1995).

Szybalski et al., "Class-IIS restriction enzymes—a review", Gene, 100:13-26, (1991).

Takio et al., "Primary structure of the regulatory subunit of type II CAMP-dependent protein kinase from bovine cardiac muscle," Proc. Natl. Acad. Sci. USA 79: 2544-25489 (1982).

Tammen et al., "Proteolytic cleavage of glucagon-like peptide-1 by pancreatic β cells and by fetal calf serum analyzed by mass spectrometry", J. Chromatogr. A, 852:285-295, (1999).

Tang et al., "Chip-based genotyping by mass spectrometry", Proc. Natl. Acad. Sci. USA, 96:10016-10020, (1999).

Tang et al., "Matrix-assisted laser desorption/ionization mass spectrometry of immobilized duplex DNA probes", Nucl. Acids Res., 23(16):3126-3131, (1995).

Tang et al., Int J. Mass Spec., 226(1):37-54 (2003).

Taranenko et al., "Laser desorption mass spectrometry for point mutation detection," Genetic Analysis: Biomolecular Engineering, 13:87-94, (1996).

Taylor, S.S., "Dynamics and Integration of Signaling by PKA," slides presented at at the 3rd Annual WyethlDouglas College Lectureship held at Rutger's University on Mar. 4, 2003.

Thiele et al., "High Ethanol Consumption and Low Sensitivity to Ethanol-Induced Sedation in Protein Kinase A-Mutant Mice," The Journal of Neuroscience 20:RC75:1-6 (2000).

Thompson, J.N., "Fitting robots with white coats", Laboratory Automation and Information Management, 31:173-193, (1996).

Tilley et al., "Structure activity of C-terminal modified analogs of AcCCK-7", Int. J. Pept. Protein Res., 3:322-336 (1992).

Tobe et al., "Single-well genotyping of diallelic sequence variations by a two-color ELISA-based oligonucleotide ligation assay", Nucl. Acids Res., 24:3728-3732, (1996).

Transscription and translation, a practical approach, Book: Hames, B.D. and Higgins, S.J. (Eds.), IRL Press Limited, Oxford, England (1984), Table of Contents only.

Udenfriend et al., "Scintillation Proximity Assay: A Sensitive and Continuous Isotopic Method for Monitoring Ligand/Receptor and Antigen/Antibody Interactions", Anal. Biochem., 161:494-500, (1987).

Udenfried et al., "Scintillation proximity radioimmunassay utilizing 125I-labeled ligands", Proc. Natl. Acad. Sci. USA, 82:8672-8676 (1985).

Ugozzoli, et al., "Detection of Specific Alleles by Using Allele-Specific Primer Extension Followed by a Capture on Solid Support", Genet. Anal. Tech. Appl.(GATA), 9(4):107-112, (1992).

Uracil-DNA Glycosylase (UDG), product description. New England Biolabs. http://circuit.neb.com/neb/products/mod_enzymes/280.html, (Dec. 21, 2000).

Uracil-DNA Glycosylase, product description. Roche Molecular Biochemicals Catalog Version 3, Nov. 1999 http:/biochem.roche.com/pack-insert/1269062a.pdf, (Dec. 21, 2000).

Urlaub, G. and Chasin, L.A., "Isolation of Chinese hamster cell mutants deficient in dihydrofolate reductase actvitity", Proc. Natl. Acad. Sci. USA, 77(7):4216-4220, (1980).

van den Boom et al., "Combined amplification and sequencing in a single reaction using two DNA polymerase with differential incorporation rates for dideoxynucleotides", J. Biochem. Biophys. Methods, 35:69-79, (1997).

van den Boom et al., "Forward and Reverse DNA Sequencing in a Single Reaction", Anal. Biochem., 256:127-129, (1998).

Vaughan et al., "Glycosylase mediated polymorphism detection (GMPD)—a novel process for genetic analysis", Genetic Analysis: Biomolecular Engineering, 14:169-175, (1999).

Veber et al., "The design of metabolically-stable peptide analogs," Trends in Neurosciences 8:392-396 (1985).

Vijayaraghavan et al., "Protein Kinase A-anchoring Inhibitor Peptides Arrest Mammalian Sperm Motility", J. Biol, Chem., 272:4747-4752 (1997).

Wada et al., "Detection of Single-nucleotide Mutations Including Substitutions and Deletions by Matrix-assisted Laser Desorption/Ionization Time-of-flight Mass Spectrometry," Rapid Communications in Mass Spectrometry, 11:1657-1660, (1997).

Waga et al., "Reconstruction of Complete SV40 DNA Replication with Purified Replication Factors", J. Biol. Chem., 269(14):10923-10934, (1994).

Wagner et al., "The human β-globin gene and a functional viral thymidine kinase gene in developing mice", Proc. Natl. Acad. Sci. USA, 78:5016-5020, (1981).

Wallace et al., "Hybridization of synthetic oligodeoxyribonucleotides to phi chi 174 DNA: the effect of single base pair mismatch", Nucl. Acids Res., 6:3543-3557, (1979).

Wang et al., 'Allene Y9 and Y10: low-temperature measurements of line intensity', J. Mol. Spectrosc., 194(20):256-268, (1999).

Weaner et al., "Tritium Labeling of N-Protected Amino Acids and Peptides Containing O-Alkyl-Tyrosyl residues," in Synthesis and Applications of Istopically Labelled Compounds J. Allen (Ed.) Chichester, New York: John Wiley & Sons Ltd, pp. 137-140 (1995).

Weiler et al., "Hybridisation based DNA screening on peptide nucleic acid (PNA) oligomer arrays", Nucl. Acids Res., 25:2792-2799, (1997).

Wen et al., "High Affinity Binding of the Heat-stable Protein Kinase Inhibitor to the Catalytic Subunit of cAMPA-dependent Protein Kinase Is Selectively Abolished by Mutation of Arg", J. Biol. Chem., 269(11):8423-8430 (1994).

Wenschuh et al., "Coherent Membrane Supports for Parallel Microsynthesis and Screening of Bioactive Peptides", Biopolymers, 55:188-206 (2000).

Westphal et al., "Transposon-generated 'knock-out' and 'knock-in' gene-targeting constructs for use in mice", Curr. Biol., 7:530-533 (1997).

Wigler et al., "DNA-mediated transfer of the adenine phosophoribosyltransferase locus into mammalian cells", Proc. Natl. Acad. Sci. USA, 76(3):1373-1376 (1979).

Wilson, G.G. and Murray, N.E., "Restriction and Modification Systems", Annu. Rev. Genet., 25:585-627, (1991).

Wolfenden et al., "Affinities of Amino Acid Side Chains for Solvent Water," Biochemistry 20: 849-855 (1981).

Xu et al., J. Clin. Microbiol., 38(11):4114-4120.

Yasuda et al., "Genetic Polymorphisms Detectable in Human Urine: Their Application to Forensic Individualization." Japanese Journal of Legal Medicine 91. 407-41 6 (1997).

Yates, J. Mass Spec. 33:1-19.

Yen et al., Optically controlled ligand delivery, 1, "Synthesis if water-soluble copolymers containing photocleavable bonds", Makromol. Chem., 190:69-82, (1989).

Zalipsky et al., "Functionalized Poly(ethylene glycol) for Preparation of Biologically Relevant Conjugate," Bioconjugate Chemistry 6:150-165 (1995).

Zangenberg et al., PCR Applications: Protocols for Functional Genomics. Innis et al Eds. p. 73-94 (1999). Academic Press.

Zhang et al., "Long-Distance PCR-Based Strategy for Preparing Knock-In Vectors Directly from ES Cell Genomic DNA", Biotechniques, 25:784-786, 788 (1998).

SEQUENCE LISTING

<160> NUMBER OF SEQ ID NOS: 112

<210> SEQ ID NO 1
<211> LENGTH: 27
<212> TYPE: PRT
<213> ORGANISM: Homo sapiens

<400> SEQUENCE: 1

Val Gln Gly Asn Thr Asp Glu Ala Gln Glu Glu Leu Ala Trp Lys Ile
1               5                   10                  15

Ala Lys Met Ile Val Ser Asp Ile Met Gln Gln
            20                  25

<210> SEQ ID NO 2
<211> LENGTH: 27
<212> TYPE: PRT
<213> ORGANISM: Homo sapiens

<400> SEQUENCE: 2

Val Gln Gly Asn Thr Asp Glu Ala Gln Glu Glu Leu Ala Trp Lys Ile
1               5                   10                  15

Ala Lys Met Ile Val Ser Asp Val Met Gln Gln
            20                  25

<210> SEQ ID NO 3
<211> LENGTH: 21
<212> TYPE: PRT
<213> ORGANISM: Homo sapiens

<400> SEQUENCE: 3

Asn Thr Asp Glu Ala Gln Glu Glu Leu Ala Trp Lys Ile Ala Lys Met
1               5                   10                  15

Ile Val Ser Asp Ile
            20

<210> SEQ ID NO 4
<211> LENGTH: 15
<212> TYPE: PRT
<213> ORGANISM: Homo sapiens

<400> SEQUENCE: 4

Glu Ala Gln Glu Glu Leu Ala Trp Lys Ile Ala Lys Met Ile Val
1               5                   10                  15

<210> SEQ ID NO 5
<211> LENGTH: 25
<212> TYPE: PRT
<213> ORGANISM: Homo sapiens

<400> SEQUENCE: 5

Gln Gly Asn Thr Asp Glu Ala Gln Glu Glu Leu Ala Trp Lys Ile Ala
1               5                   10                  15

Lys Met Ile Val Ser Asp Ile Met Gln
            20                  25

<210> SEQ ID NO 6
<211> LENGTH: 23
<212> TYPE: PRT
<213> ORGANISM: Homo sapiens

<400> SEQUENCE: 6

```
Gly Asn Thr Asp Glu Ala Gln Glu Glu Leu Ala Trp Lys Ile Ala Lys
1               5                   10                  15

Met Ile Val Ser Asp Ile Met
            20
```

<210> SEQ ID NO 7
<211> LENGTH: 21
<212> TYPE: PRT
<213> ORGANISM: Homo sapiens

<400> SEQUENCE: 7

```
Asn Thr Asp Glu Ala Gln Glu Glu Leu Ala Trp Lys Ile Ala Lys Met
1               5                   10                  15

Ile Val Ser Asp Ile
            20
```

<210> SEQ ID NO 8
<211> LENGTH: 19
<212> TYPE: PRT
<213> ORGANISM: Homo sapiens

<400> SEQUENCE: 8

```
Thr Asp Glu Ala Gln Glu Glu Leu Ala Trp Lys Ile Ala Lys Met Ile
1               5                   10                  15

Val Ser Asp
```

<210> SEQ ID NO 9
<211> LENGTH: 17
<212> TYPE: PRT
<213> ORGANISM: Homo sapiens

<400> SEQUENCE: 9

```
Asp Glu Ala Gln Glu Glu Leu Ala Trp Lys Ile Ala Lys Met Ile Val
1               5                   10                  15

Ser
```

<210> SEQ ID NO 10
<211> LENGTH: 13
<212> TYPE: PRT
<213> ORGANISM: Homo sapiens

<400> SEQUENCE: 10

```
Ala Gln Glu Glu Leu Ala Trp Lys Ile Ala Lys Met Ile
1               5                   10
```

<210> SEQ ID NO 11
<211> LENGTH: 11
<212> TYPE: PRT
<213> ORGANISM: Homo sapiens

<400> SEQUENCE: 11

```
Gln Glu Glu Leu Ala Trp Lys Ile Ala Lys Met
1               5                   10
```

<210> SEQ ID NO 12
<211> LENGTH: 9
<212> TYPE: PRT
<213> ORGANISM: Homo sapiens

<400> SEQUENCE: 12

```
Glu Glu Leu Ala Trp Lys Ile Ala Lys
1               5
```

```
<210> SEQ ID NO 13
<211> LENGTH: 7
<212> TYPE: PRT
<213> ORGANISM: Homo sapiens

<400> SEQUENCE: 13

Glu Leu Ala Trp Lys Ile Ala
1               5

<210> SEQ ID NO 14
<211> LENGTH: 30
<212> TYPE: PRT
<213> ORGANISM: Homo sapiens
<220> FEATURE:
<221> NAME/KEY: MOD_RES
<222> LOCATION: 1
<223> OTHER INFORMATION: Xaa is biotin
<220> FEATURE:
<221> NAME/KEY: MOD_RES
<222> LOCATION: 2,3
<223> OTHER INFORMATION: bAla

<400> SEQUENCE: 14

Xaa Xaa Xaa Val Gln Gly Asn Thr Asp Glu Ala Gln Glu Leu Ala
1               5                   10                  15

Trp Lys Ile Ala Lys Met Ile Val Ser Asp Ile Met Gln Gln
            20                  25                  30

<210> SEQ ID NO 15
<211> LENGTH: 28
<212> TYPE: PRT
<213> ORGANISM: Homo sapiens
<220> FEATURE:
<221> NAME/KEY: ACETYLATION
<222> LOCATION: 28
<223> OTHER INFORMATION: Xaa is c-terminal acetylation

<400> SEQUENCE: 15

Gln Gln Met Val Asp Ser Val Ile Met Lys Ala Ile Lys Trp Ala Leu
1               5                   10                  15

Glu Glu Gln Ala Glu Asp Thr Asn Gly Gln Val Xaa
            20                  25

<210> SEQ ID NO 16
<211> LENGTH: 28
<212> TYPE: PRT
<213> ORGANISM: Homo sapiens
<220> FEATURE:
<221> NAME/KEY: ACETYLATION
<222> LOCATION: 28
<223> OTHER INFORMATION: Xaa is C-terminal acetylation

<400> SEQUENCE: 16

Gln Gln Met Ile Asp Ser Val Ile Met Lys Ala Ile Lys Trp Ala Leu
1               5                   10                  15

Glu Glu Gln Ala Glu Asp Thr Asn Gly Gln Val Xaa
            20                  25

<210> SEQ ID NO 17
<211> LENGTH: 27
<212> TYPE: PRT
<213> ORGANISM: Homo sapiens
<220> FEATURE:
<221> NAME/KEY: MOD_RES
<222> LOCATION: 6
<223> OTHER INFORMATION: Xaa is D-Threonine
<220> FEATURE:
<221> NAME/KEY: VARIANT
```

```
<222> LOCATION: 24
<223> OTHER INFORMATION: Xaa is Ile or Val

<400> SEQUENCE: 17

Val Gln Gly Asn Thr Xaa Glu Ala Gln Glu Glu Leu Ala Trp Lys Ile
 1               5                  10                  15

Ala Lys Met Ile Val Ser Asp Xaa Met Gln Gln
            20                  25

<210> SEQ ID NO 18
<211> LENGTH: 27
<212> TYPE: PRT
<213> ORGANISM: Homo sapiens
<220> FEATURE:
<221> NAME/KEY: MOD_RES
<222> LOCATION: 9
<223> OTHER INFORMATION: Xaa is D-Phenylalanine
<220> FEATURE:
<221> NAME/KEY: VARIANT
<222> LOCATION: 24
<223> OTHER INFORMATION: Xaa is Ile or Val

<400> SEQUENCE: 18

Val Gln Gly Asn Thr Asp Glu Ala Xaa Glu Glu Leu Ala Trp Lys Ile Ala
 1               5                  10                  15

Lys Met Ile Val Ser Asp Xaa Met Gln Gln
        20                  25

<210> SEQ ID NO 19
<211> LENGTH: 27
<212> TYPE: PRT
<213> ORGANISM: Homo sapiens
<220> FEATURE:
<221> NAME/KEY: MOD_RES
<222> LOCATION: 9
<223> OTHER INFORMATION: Xaa is D-Ile
<220> FEATURE:
<221> NAME/KEY: VARIANT
<222> LOCATION: 24
<223> OTHER INFORMATION: Xaa is Ile or Val

<400> SEQUENCE: 19

Val Gln Gly Asn Thr Asp Glu Ala Xaa Glu Glu Leu Ala Trp Lys Ile
 1               5                  10                  15

Ala Lys Met Ile Val Ser Asp Xaa Met Gln Gln
            20                  25

<210> SEQ ID NO 20
<211> LENGTH: 27
<212> TYPE: PRT
<213> ORGANISM: Homo sapiens
<220> FEATURE:
<221> NAME/KEY: MOD_RES
<222> LOCATION: 9
<223> OTHER INFORMATION: Xaa is D-Leucine
<220> FEATURE:
<221> NAME/KEY: VARIANT
<222> LOCATION: 24
<223> OTHER INFORMATION: Xaa is Ile or Val

<400> SEQUENCE: 20

Val Gln Gly Asn Thr Asp Glu Ala Xaa Glu Glu Leu Ala Trp Lys Ile
 1               5                  10                  15

Ala Lys Met Ile Val Ser Asp Xaa Met Gln Gln
            20                  25

<210> SEQ ID NO 21
```

```
<211> LENGTH: 27
<212> TYPE: PRT
<213> ORGANISM: Homo sapiens
<220> FEATURE:
<221> NAME/KEY: MOD_RES
<222> LOCATION: 9
<223> OTHER INFORMATION: Xaa is D-Valine
<220> FEATURE:
<221> NAME/KEY: VARIANT
<222> LOCATION: 24
<223> OTHER INFORMATION: Xaa is Ile or Val

<400> SEQUENCE: 21

Val Gln Gly Asn Thr Asp Glu Ala Xaa Glu Glu Leu Ala Trp Lys Ile
 1               5                  10                  15

Ala Lys Met Ile Val Ser Asp Xaa Met Gln Gln
            20                  25

<210> SEQ ID NO 22
<211> LENGTH: 27
<212> TYPE: PRT
<213> ORGANISM: Homo sapiens
<220> FEATURE:
<221> NAME/KEY: MOD_RES
<222> LOCATION: 9
<223> OTHER INFORMATION: Xaa is D-Tryptophan
<220> FEATURE:
<221> NAME/KEY: VARIANT
<222> LOCATION: 24
<223> OTHER INFORMATION: Xaa is Ile or Val

<400> SEQUENCE: 22

Val Gln Gly Asn Thr Asp Glu Ala Xaa Glu Glu Leu Ala Trp Lys Ile
 1               5                  10                  15

Ala Lys Met Ile Val Ser Asp Xaa Met Gln Gln
            20                  25

<210> SEQ ID NO 23
<211> LENGTH: 27
<212> TYPE: PRT
<213> ORGANISM: Homo sapiens
<220> FEATURE:
<221> NAME/KEY: MOD_RES
<222> LOCATION: 9
<223> OTHER INFORMATION: Xaa is D-Tyrosine
<220> FEATURE:
<221> NAME/KEY: VARIANT
<222> LOCATION: 24
<223> OTHER INFORMATION: Xaa is Ile or Val

<400> SEQUENCE: 23

Val Gln Gly Asn Thr Asp Glu Ala Xaa Glu Glu Leu Ala Trp Lys Ile
 1               5                  10                  15

Ala Lys Met Ile Val Ser Asp Xaa Met Gln Gln
            20                  25

<210> SEQ ID NO 24
<211> LENGTH: 27
<212> TYPE: PRT
<213> ORGANISM: Homo sapiens
<220> FEATURE:
<221> NAME/KEY: MOD_RES
<222> LOCATION: 21
<223> OTHER INFORMATION: Xaa is D-Leucine
<220> FEATURE:
<221> NAME/KEY: VARIANT
<222> LOCATION: 24
<223> OTHER INFORMATION: Xaa is Ile or Val

<400> SEQUENCE: 24
```

```
Val Gln Gly Asn Thr Asp Glu Ala Gln Glu Glu Leu Ala Trp Lys Ile
1               5                   10                  15

Ala Lys Met Ile Xaa Ser Asp Xaa Met Gln Gln
            20              25
```

<210> SEQ ID NO 25
<211> LENGTH: 27
<212> TYPE: PRT
<213> ORGANISM: Homo sapiens
<220> FEATURE:
<221> NAME/KEY: MOD_RES
<222> LOCATION: 21
<223> OTHER INFORMATION: Xaa is D-Leucine
<220> FEATURE:
<221> NAME/KEY: VARIANT
<222> LOCATION: 24
<223> OTHER INFORMATION: Xaa is Ile or Val

<400> SEQUENCE: 25

```
Val Gln Gly Asn Thr Asp Glu Ala Gln Glu Glu Leu Ala Trp Lys Ile
1               5                   10                  15

Ala Lys Met Ile Val Xaa Asp Xaa Met Gln Gln
            20              25
```

<210> SEQ ID NO 26
<211> LENGTH: 27
<212> TYPE: PRT
<213> ORGANISM: Homo sapiens
<220> FEATURE:
<221> NAME/KEY: VARIANT
<222> LOCATION: 24
<223> OTHER INFORMATION: Xaa is Ile or Val
<220> FEATURE:
<221> NAME/KEY: MOD_RES
<222> LOCATION: 25
<223> OTHER INFORMATION: Xaa is D-Phenylalanine

<400> SEQUENCE: 26

```
Val Gln Gly Asn Thr Asp Glu Ala Gln Glu Glu Leu Ala Trp Lys Ile
1               5                   10                  15

Ala Lys Met Ile Val Ser Asp Xaa Xaa Gln Gln
            20              25
```

<210> SEQ ID NO 27
<211> LENGTH: 27
<212> TYPE: PRT
<213> ORGANISM: Homo sapiens
<220> FEATURE:
<221> NAME/KEY: VARIANT
<222> LOCATION: 24
<223> OTHER INFORMATION: Xaa is Ile or Val

<400> SEQUENCE: 27

```
Val Gln Gly Asn Thr Asp Glu Ala Gln Glu Glu Leu Phe Trp Lys Ile
1               5                   10                  15

Ala Lys Met Ile Val Ser Asp Xaa Met Gln Gln
            20              25
```

<210> SEQ ID NO 28
<211> LENGTH: 27
<212> TYPE: PRT
<213> ORGANISM: Homo sapiens
<220> FEATURE:
<221> NAME/KEY: VARIANT
<222> LOCATION: 24
<223> OTHER INFORMATION: Xaa is Ile or Val

<400> SEQUENCE: 28

Val Gln Gly Asn Thr Asp Glu Ala Gln Glu Glu Leu Ile Trp Lys Ile
1               5                   10                  15

Ala Lys Met Ile Val Ser Asp Xaa Met Gln Gln
            20                  25

<210> SEQ ID NO 29
<211> LENGTH: 27
<212> TYPE: PRT
<213> ORGANISM: Homo sapiens
<220> FEATURE:
<221> NAME/KEY: VARIANT
<222> LOCATION: 24
<223> OTHER INFORMATION: Xaa is Ile or Val

<400> SEQUENCE: 29

Val Gln Gly Asn Thr Asp Glu Ala Gln Glu Glu Leu Leu Trp Lys Ile
1               5                   10                  15

Ala Lys Met Ile Val Ser Asp Xaa Met Gln Gln
            20                  25

<210> SEQ ID NO 30
<211> LENGTH: 27
<212> TYPE: PRT
<213> ORGANISM: Homo sapiens
<220> FEATURE:
<221> NAME/KEY: VARIANT
<222> LOCATION: 24
<223> OTHER INFORMATION: Xaa is Ile or Val

<400> SEQUENCE: 30

Val Gln Gly Asn Thr Asp Glu Ala Gln Glu Glu Leu Ala Trp Cys Ile
1               5                   10                  15

Ala Lys Met Ile Val Ser Asp Xaa Met Gln Gln
            20                  25

<210> SEQ ID NO 31
<211> LENGTH: 27
<212> TYPE: PRT
<213> ORGANISM: Homo sapiens
<220> FEATURE:
<221> NAME/KEY: VARIANT
<222> LOCATION: 24
<223> OTHER INFORMATION: Xaa is Ile or Val

<400> SEQUENCE: 31

Val Gln Gly Asn Thr Asp Glu Ala Gln Glu Glu Leu Ala Trp Lys Ile
1               5                   10                  15

Ala Cys Met Ile Val Ser Asp Xaa Met Gln Gln
            20                  25

<210> SEQ ID NO 32
<211> LENGTH: 27
<212> TYPE: PRT
<213> ORGANISM: Homo sapiens
<220> FEATURE:
<221> NAME/KEY: VARIANT
<222> LOCATION: 24
<223> OTHER INFORMATION: Xaa is Ile or Val

<400> SEQUENCE: 32

Val Gln Gly Asn Thr Asp Glu Ala Gln Glu Glu Leu Ala Trp Lys Ile
1               5                   10                  15

Ala Lys Cys Ile Val Ser Asp Xaa Met Gln Gln
            20                  25

```
<210> SEQ ID NO 33
<211> LENGTH: 27
<212> TYPE: PRT
<213> ORGANISM: Homo sapiens
<220> FEATURE:
<221> NAME/KEY: VARIANT
<222> LOCATION: 24
<223> OTHER INFORMATION: Xaa is Ile or Val

<400> SEQUENCE: 33

Val Gln Gly Asn Thr Asp Glu Ala Gln Glu Glu Leu Ala Trp Lys Ile
1               5                   10                  15

Ala Lys Met Ile Val Cys Asp Xaa Met Gln Gln
            20                  25

<210> SEQ ID NO 34
<211> LENGTH: 27
<212> TYPE: PRT
<213> ORGANISM: Homo sapiens
<220> FEATURE:
<221> NAME/KEY: VARIANT
<222> LOCATION: 24
<223> OTHER INFORMATION: Xaa is Ile or Val

<400> SEQUENCE: 34

Val Gln Gly Asn Thr Asp Glu Ala Gln Glu Glu Cys Ala Trp Lys Ile
1               5                   10                  15

Ala Lys Met Ile Val Ser Asp Xaa Met Gln Gln
            20                  25

<210> SEQ ID NO 35
<211> LENGTH: 27
<212> TYPE: PRT
<213> ORGANISM: Homo sapiens
<220> FEATURE:
<221> NAME/KEY: VARIANT
<222> LOCATION: 24
<223> OTHER INFORMATION: Xaa is Ile or Val

<400> SEQUENCE: 35

Val Gln Gly Asn Thr Asp Glu Ala Gln Glu Glu Lys Ala Trp Lys Ile
1               5                   10                  15

Ala Lys Met Ile Val Ser Asp Xaa Met Gln Gln
            20                  25

<210> SEQ ID NO 36
<211> LENGTH: 27
<212> TYPE: PRT
<213> ORGANISM: Homo sapiens
<220> FEATURE:
<221> NAME/KEY: VARIANT
<222> LOCATION: 24
<223> OTHER INFORMATION: Xaa is Ile or Val

<400> SEQUENCE: 36

Val Gln Gly Asn Thr Asp Glu Ala Gln Glu Glu Leu His Trp Lys Ile
1               5                   10                  15

Ala Lys Met Ile Val Ser Asp Xaa Met Gln Gln
            20                  25

<210> SEQ ID NO 37
<211> LENGTH: 27
<212> TYPE: PRT
<213> ORGANISM: Homo sapiens
<220> FEATURE:
<221> NAME/KEY: VARIANT
<222> LOCATION: 24
```

<223> OTHER INFORMATION: Xaa is Ile or Val

<400> SEQUENCE: 37

Val Gln Gly Asn Thr Asp Glu Ala Gln Glu Glu Leu Lys Trp Lys Ile
1               5                   10                  15

Ala Lys Met Ile Val Ser Asp Xaa Met Gln Gln
            20                  25

<210> SEQ ID NO 38
<211> LENGTH: 27
<212> TYPE: PRT
<213> ORGANISM: Homo sapiens
<220> FEATURE:
<221> NAME/KEY: VARIANT
<222> LOCATION: 24
<223> OTHER INFORMATION: Xaa is Ile or Val

<400> SEQUENCE: 38

Val Gln Gly Asn Thr Asp Glu Ala Gln Glu Glu Leu Met Trp Lys Ile
1               5                   10                  15

Ala Lys Met Ile Val Ser Asp Xaa Met Gln Gln
            20                  25

<210> SEQ ID NO 39
<211> LENGTH: 27
<212> TYPE: PRT
<213> ORGANISM: Homo sapiens
<220> FEATURE:
<221> NAME/KEY: VARIANT
<222> LOCATION: 24
<223> OTHER INFORMATION: Xaa is Ile or Val

<400> SEQUENCE: 39

Val Gln Gly Asn Thr Asp Glu Ala Gln Glu Glu Leu Asn Trp Lys Ile
1               5                   10                  15

Ala Lys Met Ile Val Ser Asp Xaa Met Gln Gln
            20                  25

<210> SEQ ID NO 40
<211> LENGTH: 27
<212> TYPE: PRT
<213> ORGANISM: Homo sapiens
<220> FEATURE:
<221> NAME/KEY: VARIANT
<222> LOCATION: 24
<223> OTHER INFORMATION: Xaa is Ile or Val

<400> SEQUENCE: 40

Val Gln Gly Asn Thr Asp Glu Ala Gln Glu Glu Leu Val Trp Lys Ile
1               5                   10                  15

Ala Lys Met Ile Val Ser Asp Xaa Met Gln Gln
            20                  25

<210> SEQ ID NO 41
<211> LENGTH: 27
<212> TYPE: PRT
<213> ORGANISM: Homo sapiens
<220> FEATURE:
<221> NAME/KEY: VARIANT
<222> LOCATION: 24
<223> OTHER INFORMATION: Xaa is Ile or Val

<400> SEQUENCE: 41

Val Gln Gly Asn Thr Asp Glu Ala Gln Glu Glu Leu Trp Trp Lys Ile
1               5                   10                  15

Ala Lys Met Ile Val Ser Asp Xaa Met Gln Gln
            20                  25

<210> SEQ ID NO 42
<211> LENGTH: 27
<212> TYPE: PRT
<213> ORGANISM: Homo sapiens
<220> FEATURE:
<221> NAME/KEY: VARIANT
<222> LOCATION: 24
<223> OTHER INFORMATION: Xaa is Ile or Val

<400> SEQUENCE: 42

Val Gln Gly Asn Thr Asp Glu Ala Gln Glu Glu Leu Tyr Trp Lys Ile
1               5                   10                  15

Ala Lys Met Ile Val Ser Asp Xaa Met Gln Gln
            20                  25

<210> SEQ ID NO 43
<211> LENGTH: 27
<212> TYPE: PRT
<213> ORGANISM: Homo sapiens
<220> FEATURE:
<221> NAME/KEY: VARIANT
<222> LOCATION: 24
<223> OTHER INFORMATION: Xaa is Ile or Val

<400> SEQUENCE: 43

Val Gln Gly Asn Thr Asp Glu Ala Gln Glu Glu Leu Ala Trp Lys Ile
1               5                   10                  15

Ala Lys Met Ile Val Ser Cys Xaa Met Gln Gln
            20                  25

<210> SEQ ID NO 44
<211> LENGTH: 27
<212> TYPE: PRT
<213> ORGANISM: Homo sapiens
<220> FEATURE:
<221> NAME/KEY: VARIANT
<222> LOCATION: 24
<223> OTHER INFORMATION: Xaa is Ile or Val

<400> SEQUENCE: 44

Val Gln Gly Asn Thr Asp Glu Ala Phe Glu Glu Leu Ala Trp Lys Ile
1               5                   10                  15

Ala Lys Met Ile Val Ser Asp Xaa Met Gln Gln
            20                  25

<210> SEQ ID NO 45
<211> LENGTH: 27
<212> TYPE: PRT
<213> ORGANISM: Homo sapiens
<220> FEATURE:
<221> NAME/KEY: VARIANT
<222> LOCATION: 24
<223> OTHER INFORMATION: Xaa is Ile or Val

<400> SEQUENCE: 45

Val Gln Gly Asn Thr Asp Glu Ala Ile Glu Glu Leu Ala Trp Lys Ile
1               5                   10                  15

Ala Lys Met Ile Val Ser Asp Xaa Met Gln Gln
            20                  25

<210> SEQ ID NO 46
<211> LENGTH: 27
<212> TYPE: PRT

```
<213> ORGANISM: Homo sapiens
<220> FEATURE:
<221> NAME/KEY: VARIANT
<222> LOCATION: 24
<223> OTHER INFORMATION: Xaa is Ile or Val

<400> SEQUENCE: 46

Val Gln Gly Asn Thr Asp Glu Ala Leu Glu Glu Leu Ala Trp Lys Ile
 1               5                  10                  15

Ala Lys Met Ile Val Ser Asp Xaa Met Gln Gln
            20                  25

<210> SEQ ID NO 47
<211> LENGTH: 27
<212> TYPE: PRT
<213> ORGANISM: Homo sapiens
<220> FEATURE:
<221> NAME/KEY: VARIANT
<222> LOCATION: 24
<223> OTHER INFORMATION: Xaa is Ile or Val

<400> SEQUENCE: 47

Val Gln Gly Asn Thr Asp Glu Ala Val Glu Glu Leu Ala Trp Lys Ile
 1               5                  10                  15

Ala Lys Met Ile Val Ser Asp Xaa Met Gln Gln
            20                  25

<210> SEQ ID NO 48
<211> LENGTH: 27
<212> TYPE: PRT
<213> ORGANISM: Homo sapiens
<220> FEATURE:
<221> NAME/KEY: VARIANT
<222> LOCATION: 24
<223> OTHER INFORMATION: Xaa is Ile or Val

<400> SEQUENCE: 48

Val Gln Gly Asn Thr Asp Glu Ala Gln Glu Glu Leu Ala Trp Lys Ile
 1               5                  10                  15

Ala Lys Met Ile Val Ser Asp Xaa Phe Gln Gln
            20                  25

<210> SEQ ID NO 49
<211> LENGTH: 27
<212> TYPE: PRT
<213> ORGANISM: Homo sapiens
<220> FEATURE:
<221> NAME/KEY: VARIANT
<222> LOCATION: 24
<223> OTHER INFORMATION: Xaa is Ile or Val

<400> SEQUENCE: 49

Val Gln Gly Asn Thr Asp Glu Ala Gln Glu Glu Leu Ala Trp Lys Ile
 1               5                  10                  15

Ala Lys Met Ile Val Ser Asp Xaa Ile Gln Gln
            20                  25

<210> SEQ ID NO 50
<211> LENGTH: 27
<212> TYPE: PRT
<213> ORGANISM: Homo sapiens
<220> FEATURE:
<221> NAME/KEY: VARIANT
<222> LOCATION: 24
<223> OTHER INFORMATION: Xaa is Ile or Val

<400> SEQUENCE: 50
```

Val Gln Gly Asn Thr Asp Glu Ala Gln Glu Leu Ala Trp Lys Ile
1               5                   10                  15

Ala Lys Met Ile Val Ser Asp Xaa Leu Gln Gln
            20                  25

<210> SEQ ID NO 51
<211> LENGTH: 27
<212> TYPE: PRT
<213> ORGANISM: Homo sapiens
<220> FEATURE:
<221> NAME/KEY: VARIANT
<222> LOCATION: 24
<223> OTHER INFORMATION: Xaa is Ile or Val

<400> SEQUENCE: 51

Val Gln Gly Asn Thr Asp Glu Ala Gln Glu Phe Ala Trp Lys Ile
1               5                   10                  15

Ala Lys Met Ile Val Ser Asp Xaa Met Gln Gln
            20                  25

<210> SEQ ID NO 52
<211> LENGTH: 27
<212> TYPE: PRT
<213> ORGANISM: Homo sapiens
<220> FEATURE:
<221> NAME/KEY: VARIANT
<222> LOCATION: 24
<223> OTHER INFORMATION: Xaa is Ile or Val

<400> SEQUENCE: 52

Val Gln Gly Asn Thr Asp Glu Ala Gln Glu Leu Ala Trp Lys Ile
1               5                   10                  15

Ala Lys Met Ile Ile Ser Asp Xaa Met Gln Gln
            20                  25

<210> SEQ ID NO 53
<211> LENGTH: 27
<212> TYPE: PRT
<213> ORGANISM: Homo sapiens
<220> FEATURE:
<221> NAME/KEY: VARIANT
<222> LOCATION: 24
<223> OTHER INFORMATION: Xaa is Ile or Val

<400> SEQUENCE: 53

Val Gln Gly Asn Thr Asp Glu Ala Gln Glu Leu Ala Trp Lys Ile
1               5                   10                  15

Ala Lys Met Ile Leu Ser Asp Xaa Met Gln Gln
            20                  25

<210> SEQ ID NO 54
<211> LENGTH: 27
<212> TYPE: PRT
<213> ORGANISM: Homo sapiens
<220> FEATURE:
<221> NAME/KEY: VARIANT
<222> LOCATION: 24
<223> OTHER INFORMATION: Xaa is Ile or Val

<400> SEQUENCE: 54

Val Gln Gly Asn Thr Asp Glu Ala Gln Glu Leu Ala Trp Lys Ile
1               5                   10                  15

Ala Lys Met Ile Trp Ser Asp Xaa Met Gln Gln
            20                  25

<210> SEQ ID NO 55
<211> LENGTH: 1119
<212> TYPE: DNA
<213> ORGANISM: Mus musculus
<220> FEATURE:
<221> NAME/KEY: CDS
<222> LOCATION: (1)...(1119)
<223> OTHER INFORMATION: cDNA: truncated version of mouse D-AKAP2

<400> SEQUENCE: 55

| | | | | | | | | | | | | | | | |
|---|---|---|---|---|---|---|---|---|---|---|---|---|---|---|---|
| atg | aaa | agt | ata | gaa | caa | gat | gca | gtg | aat | act | ttt | acc | aaa | tat | ata | 48 |
| Met | Lys | Ser | Ile | Glu | Gln | Asp | Ala | Val | Asn | Thr | Phe | Thr | Lys | Tyr | Ile | |
| 1 | | | | 5 | | | | | 10 | | | | | 15 | | |

| tct | cca | gat | gct | gct | aag | cca | ata | cca | att | aca | gaa | gcc | atg | aga | aac | 96 |
| Ser | Pro | Asp | Ala | Ala | Lys | Pro | Ile | Pro | Ile | Thr | Glu | Ala | Met | Arg | Asn | |
| | | | 20 | | | | | 25 | | | | | 30 | | | |

| gac | atc | atc | gca | aag | att | tgt | gga | gaa | gat | gga | cag | gtg | gat | ccc | aac | 144 |
| Asp | Ile | Ile | Ala | Lys | Ile | Cys | Gly | Glu | Asp | Gly | Gln | Val | Asp | Pro | Asn | |
| | | 35 | | | | | 40 | | | | | 45 | | | | |

| tgt | ttc | gtt | ctg | gac | acg | gct | gta | gtc | ttt | agt | gca | atg | gag | caa | gag | 192 |
| Cys | Phe | Val | Leu | Asp | Thr | Ala | Val | Val | Phe | Ser | Ala | Met | Glu | Gln | Glu | |
| | 50 | | | | | 55 | | | | | 60 | | | | | |

| cac | ttt | agt | gag | ttt | ctg | cga | agt | cac | cat | ttc | tgt | aaa | tac | cag | att | 240 |
| His | Phe | Ser | Glu | Phe | Leu | Arg | Ser | His | His | Phe | Cys | Lys | Tyr | Gln | Ile | |
| 65 | | | | | 70 | | | | | 75 | | | | | 80 | |

| gaa | gtg | ctg | acc | agt | ggg | act | gtt | tac | ctg | gct | gat | atc | ctc | ttc | tgt | 288 |
| Glu | Val | Leu | Thr | Ser | Gly | Thr | Val | Tyr | Leu | Ala | Asp | Ile | Leu | Phe | Cys | |
| | | | | 85 | | | | | 90 | | | | | 95 | | |

| gag | tca | gcc | ctc | ttt | tat | ttt | tct | gag | tac | atg | gaa | aaa | gaa | gat | gca | 336 |
| Glu | Ser | Ala | Leu | Phe | Tyr | Phe | Ser | Glu | Tyr | Met | Glu | Lys | Glu | Asp | Ala | |
| | | | 100 | | | | | 105 | | | | | 110 | | | |

| gtg | aat | atc | tta | caa | ttc | tgg | tta | gca | gcg | gat | aat | ttc | cag | tct | cag | 384 |
| Val | Asn | Ile | Leu | Gln | Phe | Trp | Leu | Ala | Ala | Asp | Asn | Phe | Gln | Ser | Gln | |
| | | 115 | | | | | 120 | | | | | 125 | | | | |

| ctt | gct | gcc | aaa | aag | ggc | cag | tat | gat | gga | cag | gag | gcc | cag | aat | gat | 432 |
| Leu | Ala | Ala | Lys | Lys | Gly | Gln | Tyr | Asp | Gly | Gln | Glu | Ala | Gln | Asn | Asp | |
| | 130 | | | | | 135 | | | | | 140 | | | | | |

| gcc | atg | att | tta | tat | gac | aag | tac | ttt | tcc | ctc | caa | gcc | aca | cac | ccc | 480 |
| Ala | Met | Ile | Leu | Tyr | Asp | Lys | Tyr | Phe | Ser | Leu | Gln | Ala | Thr | His | Pro | |
| 145 | | | | | 150 | | | | | 155 | | | | | 160 | |

| ctt | gga | ttt | gat | gat | gtt | gta | cga | tta | gaa | att | gaa | tct | aat | atc | tgc | 528 |
| Leu | Gly | Phe | Asp | Asp | Val | Val | Arg | Leu | Glu | Ile | Glu | Ser | Asn | Ile | Cys | |
| | | | | 165 | | | | | 170 | | | | | 175 | | |

| agg | gaa | ggt | gga | cca | ctt | cct | aat | tgt | ttc | aca | act | cca | tta | cgt | cag | 576 |
| Arg | Glu | Gly | Gly | Pro | Leu | Pro | Asn | Cys | Phe | Thr | Thr | Pro | Leu | Arg | Gln | |
| | | | 180 | | | | | 185 | | | | | 190 | | | |

| gcc | tgg | aca | acc | atg | gag | aag | gtc | ttt | ttg | cct | ggt | ttt | ctg | tcc | agc | 624 |
| Ala | Trp | Thr | Thr | Met | Glu | Lys | Val | Phe | Leu | Pro | Gly | Phe | Leu | Ser | Ser | |
| | | 195 | | | | | 200 | | | | | 205 | | | | |

| aat | ctt | tat | tac | aaa | tat | ttg | aat | gat | ctc | atc | cat | tca | gtt | cga | gga | 672 |
| Asn | Leu | Tyr | Tyr | Lys | Tyr | Leu | Asn | Asp | Leu | Ile | His | Ser | Val | Arg | Gly | |
| | 210 | | | | | 215 | | | | | 220 | | | | | |

| gat | gaa | ttt | ctt | gga | ggg | aat | gtt | tcc | ctg | gct | gct | cac | ggc | tct | gtc | 720 |
| Asp | Glu | Phe | Leu | Gly | Gly | Asn | Val | Ser | Leu | Ala | Ala | His | Gly | Ser | Val | |
| 225 | | | | | 230 | | | | | 235 | | | | | 240 | |

| tgc | ctt | cct | gag | gag | tct | cac | tca | ggt | ggt | tcc | gat | ggc | tcc | act | gct | 768 |
| Cys | Leu | Pro | Glu | Glu | Ser | His | Ser | Gly | Gly | Ser | Asp | Gly | Ser | Thr | Ala | |
| | | | | 245 | | | | | 250 | | | | | 255 | | |

| cag | tct | agt | gtg | aaa | aaa | gcc | agt | att | aaa | att | ctg | aaa | aat | ttt | gat | 816 |
| Gln | Ser | Ser | Val | Lys | Lys | Ala | Ser | Ile | Lys | Ile | Leu | Lys | Asn | Phe | Asp | |
| | | | 260 | | | | | 265 | | | | | 270 | | | |

```
gaa gca ata att gtg gat gct gca agt ctg gac cca gaa tct tta tat       864
Glu Ala Ile Ile Val Asp Ala Ala Ser Leu Asp Pro Glu Ser Leu Tyr
        275                 280                 285 caa cgg aca tat gca ggg aag atg tcc ttt ggg aga gtt agt gat ttg       912
Gln Arg Thr Tyr Ala Gly Lys Met Ser Phe Gly Arg Val Ser Asp Leu
    290                 295                 300 ggg cag ttc atc cga gag tct gag cct gaa cct gat gtg aag aaa tca       960
Gly Gln Phe Ile Arg Glu Ser Glu Pro Glu Pro Asp Val Lys Lys Ser
305                 310                 315                 320 aaa gga ttc atg ttc tca caa gct atg aag aag tgg gtg caa gga aat      1008
Lys Gly Phe Met Phe Ser Gln Ala Met Lys Lys Trp Val Gln Gly Asn
                325                 330                 335 act gac gag gcc caa gaa gag cta gct tgg aag att gca aaa atg ata      1056
Thr Asp Glu Ala Gln Glu Glu Leu Ala Trp Lys Ile Ala Lys Met Ile
            340                 345                 350 gtg agt gat gtt atg cag cag gca cac cat gat caa cca cta gag aag      1104
Val Ser Asp Val Met Gln Gln Ala His His Asp Gln Pro Leu Glu Lys
        355                 360                 365 tct aca aag cta tga                                                   1119
Ser Thr Lys Leu *
    370

<210> SEQ ID NO 56
<211> LENGTH: 372
<212> TYPE: PRT
<213> ORGANISM: Mus musculus

<400> SEQUENCE: 56

Met Lys Ser Ile Glu Gln Asp Ala Val Asn Thr Phe Thr Lys Tyr Ile
1               5                   10                  15

Ser Pro Asp Ala Ala Lys Pro Ile Pro Ile Thr Glu Ala Met Arg Asn
            20                  25                  30

Asp Ile Ile Ala Lys Ile Cys Gly Glu Asp Gly Gln Val Asp Pro Asn
        35                  40                  45

Cys Phe Val Leu Asp Thr Ala Val Val Phe Ser Ala Met Glu Gln Glu
    50                  55                  60

His Phe Ser Glu Phe Leu Arg Ser His His Phe Cys Lys Tyr Gln Ile
65                  70                  75                  80

Glu Val Leu Thr Ser Gly Thr Val Tyr Leu Ala Asp Ile Leu Phe Cys
                85                  90                  95

Glu Ser Ala Leu Phe Tyr Phe Ser Glu Tyr Met Glu Lys Glu Asp Ala
            100                 105                 110

Val Asn Ile Leu Gln Phe Trp Leu Ala Ala Asp Asn Phe Gln Ser Gln
        115                 120                 125

Leu Ala Ala Lys Lys Gly Gln Tyr Asp Gly Gln Glu Ala Gln Asn Asp
    130                 135                 140

Ala Met Ile Leu Tyr Asp Lys Tyr Phe Ser Leu Gln Ala Thr His Pro
145                 150                 155                 160

Leu Gly Phe Asp Asp Val Val Arg Leu Glu Ile Glu Ser Asn Ile Cys
                165                 170                 175

Arg Glu Gly Gly Pro Leu Pro Asn Cys Phe Thr Thr Pro Leu Arg Gln
            180                 185                 190

Ala Trp Thr Thr Met Glu Lys Val Phe Leu Pro Gly Phe Leu Ser Ser
        195                 200                 205

Asn Leu Tyr Tyr Lys Tyr Leu Asn Asp Leu Ile His Ser Val Arg Gly
    210                 215                 220

Asp Glu Phe Leu Gly Gly Asn Val Ser Leu Ala Ala His Gly Ser Val
```

```
                225                 230                 235                 240
Cys Leu Pro Glu Glu Ser His Ser Gly Gly Ser Asp Gly Ser Thr Ala
                245                 250                 255

Gln Ser Ser Val Lys Lys Ala Ser Ile Lys Ile Leu Lys Asn Phe Asp
            260                 265                 270

Glu Ala Ile Ile Val Asp Ala Ala Ser Leu Asp Pro Glu Ser Leu Tyr
            275                 280                 285

Gln Arg Thr Tyr Ala Gly Lys Met Ser Phe Gly Arg Val Ser Asp Leu
        290                 295                 300

Gly Gln Phe Ile Arg Glu Ser Glu Pro Glu Pro Asp Val Lys Lys Ser
305                 310                 315                 320

Lys Gly Phe Met Phe Ser Gln Ala Met Lys Lys Trp Val Gln Gly Asn
                325                 330                 335

Thr Asp Glu Ala Gln Glu Glu Leu Ala Trp Lys Ile Ala Lys Met Ile
            340                 345                 350

Val Ser Asp Val Met Gln Gln Ala His His Asp Gln Pro Leu Glu Lys
            355                 360                 365

Ser Thr Lys Leu
    370

<210> SEQ ID NO 57
<211> LENGTH: 159
<212> TYPE: DNA
<213> ORGANISM: Artificial Sequence
<220> FEATURE:
<223> OTHER INFORMATION: Construct
<220> FEATURE:
<221> NAME/KEY: CDS
<222> LOCATION: (37)...(159)
<223> OTHER INFORMATION: cDNA construct

<400> SEQUENCE: 57
aaaggattca tgttctcaca agctatgaag aagtgg gtg caa gga aat act gac      54
                                       Val Gln Gly Asn Thr Asp
                                        1               5 gag gcc aty gaa gag cta gct tgg aag att gca aaa atg ata gtg agt    102
Glu Ala Xaa Glu Glu Leu Ala Trp Lys Ile Ala Lys Met Ile Val Ser
             10                  15                  20 gat gtt atg cag cag gca cac cat gat caa cca cta gag aag tct aca    150
Asp Val Met Gln Gln Ala His His Asp Gln Pro Leu Glu Lys Ser Thr
         25                  30                  35 aag cta tga                                                         159
Lys Leu  *
    40

<210> SEQ ID NO 58
<211> LENGTH: 40
<212> TYPE: PRT
<213> ORGANISM: Artificial Sequence
<220> FEATURE:
<221> NAME/KEY: VARIANT
<222> LOCATION: 9
<223> OTHER INFORMATION: Xaa is Ile

<400> SEQUENCE: 58

Val Gln Gly Asn Thr Asp Glu Ala Xaa Glu Glu Leu Ala Trp Lys Ile
 1               5                  10                  15

Ala Lys Met Ile Val Ser Asp Val Met Gln Gln Ala His His Asp Gln
             20                  25                  30

Pro Leu Glu Lys Ser Thr Lys Leu
             35                  40
```

```
<210> SEQ ID NO 59
<211> LENGTH: 159
<212> TYPE: DNA
<213> ORGANISM: Artificial Sequence
<220> FEATURE:
<223> OTHER INFORMATION: Construct
<220> FEATURE:
<221> NAME/KEY: CDS
<222> LOCATION: (37)...(159)
<223> OTHER INFORMATION: cDNA construct
<220> FEATURE:
<221> NAME/KEY: mutation
<222> LOCATION: 75
<223> OTHER INFORMATION: n is a or g or c or t

<400> SEQUENCE: 59
aaaggattca tgttctcaca agctatgaag aagtgg gtg caa gga aat act gac         54
                                        Val Gln Gly Asn Thr Asp
                                         1               5 gag gcc caa gaa gag cta ttn tgg aag att gca aaa atg ata gtg agt        102
Glu Ala Gln Glu Glu Leu Xaa Trp Lys Ile Ala Lys Met Ile Val Ser
            10                  15                  20 gat gtt atg cag cag gca cac cat gat caa cca cta gag aag tct aca        150
Asp Val Met Gln Gln Ala His His Asp Gln Pro Leu Glu Lys Ser Thr
        25                  30                  35 aag cta tga                                                            159
Lys Leu  *
    40

<210> SEQ ID NO 60
<211> LENGTH: 40
<212> TYPE: PRT
<213> ORGANISM: Artificial Sequence
<220> FEATURE:
<221> NAME/KEY: VARIANT
<222> LOCATION: 13
<223> OTHER INFORMATION: Xaa is Leucine

<400> SEQUENCE: 60

Val Gln Gly Asn Thr Asp Glu Ala Gln Glu Glu Leu Xaa Trp Lys Ile
 1               5                  10                  15

Ala Lys Met Ile Val Ser Asp Val Met Gln Gln Ala His His Asp Gln
            20                  25                  30

Pro Leu Glu Lys Ser Thr Lys Leu
        35                  40

<210> SEQ ID NO 61
<211> LENGTH: 159
<212> TYPE: DNA
<213> ORGANISM: Artificial Sequence
<220> FEATURE:
<223> OTHER INFORMATION: Construct
<220> FEATURE:
<221> NAME/KEY: CDS
<222> LOCATION: (37)...(159)
<223> OTHER INFORMATION: cDNA construct

<400> SEQUENCE: 61
aaaggattca tgttctcaca agctatgaag aagtgg gtg caa gga aat act gac         54
                                        Val Gln Gly Asn Thr Asp
                                         1               5 gag gcc caa gaa gag cta gct tgg aag att gca aaa atg ata tgr agt        102
Glu Ala Gln Glu Glu Leu Ala Trp Lys Ile Ala Lys Met Ile Xaa Ser
            10                  15                  20 gat gtt atg cag cag gca cac cat gat caa cca cta gag aag tct aca        150
Asp Val Met Gln Gln Ala His His Asp Gln Pro Leu Glu Lys Ser Thr
        25                  30                  35
```

```
aag cta tga                                                       159
Lys Leu  *
     40

<210> SEQ ID NO 62
<211> LENGTH: 40
<212> TYPE: PRT
<213> ORGANISM: Artificial Sequence
<220> FEATURE:
<221> NAME/KEY: VARIANT
<222> LOCATION: 21
<223> OTHER INFORMATION: Xaa is Tryptophan

<400> SEQUENCE: 62

Val Gln Gly Asn Thr Asp Glu Ala Gln Glu Leu Ala Trp Lys Ile
 1               5                  10                  15

Ala Lys Met Ile Xaa Ser Asp Val Met Gln Gln Ala His His Asp Gln
             20                  25                  30

Pro Leu Glu Lys Ser Thr Lys Leu
         35                  40

<210> SEQ ID NO 63
<211> LENGTH: 2363
<212> TYPE: DNA
<213> ORGANISM: Homo sapiens
<220> FEATURE:
<221> NAME/KEY: CDS
<222> LOCATION: (138)...(2126)
<223> OTHER INFORMATION: Wild Type AKAP-10
<300> PUBLICATION INFORMATION:
<308> DATABASE ACCESSION NUMBER: GenBank AF037439
<309> DATABASE ENTRY DATE: 1997-12-21

<400> SEQUENCE: 63
gcggcttgtt gataatatgg cggctggagc tgcctgggca tcccgaggag gcggtggggc     60
ccactcccgg aagaagggtc ccttttcgcg ctagtgcagc ggcccctctg gacccggaag    120
tccgggccgg ttgctga atg agg gga gcc ggg ccc tcc ccg cgc cag tcc      170
                Met Arg Gly Ala Gly Pro Ser Pro Arg Gln Ser
                 1               5                  10 ccc cgc acc ctc cgt ccc gac ccg ggc ccc gcc atg tcc ttc ttc cgg     218
Pro Arg Thr Leu Arg Pro Asp Pro Gly Pro Ala Met Ser Phe Phe Arg
             15                  20                  25 cgg aaa gtg aaa ggc aaa gaa caa gag aag acc tca gat gtg aag tcc     266
Arg Lys Val Lys Gly Lys Glu Gln Glu Lys Thr Ser Asp Val Lys Ser
         30                  35                  40 att aaa gct tca ata tcc gta cat tcc cca caa aaa agc act aaa aat     314
Ile Lys Ala Ser Ile Ser Val His Ser Pro Gln Lys Ser Thr Lys Asn
     45                  50                  55 cat gcc ttg ctg gag gct gca gga cca agt cat gtt gca atc aat gcc     362
His Ala Leu Leu Glu Ala Ala Gly Pro Ser His Val Ala Ile Asn Ala
 60                  65                  70                  75 att tct gcc aac atg gac tcc ttt tca agt agc agg aca gcc aca ctt     410
Ile Ser Ala Asn Met Asp Ser Phe Ser Ser Ser Arg Thr Ala Thr Leu
                 80                  85                  90 aag aag cag cca agc cac atg gag gct gct cat ttt ggt gac ctg ggc     458
Lys Lys Gln Pro Ser His Met Glu Ala Ala His Phe Gly Asp Leu Gly
             95                 100                 105 aga tct tgt ctg gac tac cag act caa gag acc aaa tca agc ctt tct     506
Arg Ser Cys Leu Asp Tyr Gln Thr Gln Glu Thr Lys Ser Ser Leu Ser
        110                 115                 120 aag acc ctt gaa caa gtc ttg cac gac act att gtc ctc cct tac ttc     554
Lys Thr Leu Glu Gln Val Leu His Asp Thr Ile Val Leu Pro Tyr Phe
```

-continued

```
                  125                 130                 135
att caa ttc atg gaa ctt cgg cga atg gag cat ttg gtg aaa ttt tgg     602
Ile Gln Phe Met Glu Leu Arg Arg Met Glu His Leu Val Lys Phe Trp
140             145                 150                 155 tta gag gct gaa agt ttt cat tca act act tgg tcg cga ata aga gca     650
Leu Glu Ala Glu Ser Phe His Ser Thr Thr Trp Ser Arg Ile Arg Ala
                160                 165                 170 cac agt cta aac aca atg aag cag agc tca ctg gct gag cct gtc tct     698
His Ser Leu Asn Thr Met Lys Gln Ser Ser Leu Ala Glu Pro Val Ser
                    175                 180                 185 cca tct aaa aag cat gaa act aca gcg tct ttt tta act gat tct ctt     746
Pro Ser Lys Lys His Glu Thr Thr Ala Ser Phe Leu Thr Asp Ser Leu
                190                 195                 200 gat aag aga ttg gag gat tct ggc tca gca cag ttg ttt atg act cat     794
Asp Lys Arg Leu Glu Asp Ser Gly Ser Ala Gln Leu Phe Met Thr His
            205                 210                 215 tca gaa gga att gac ctg aat aat aga act aac agc act cag aat cac     842
Ser Glu Gly Ile Asp Leu Asn Asn Arg Thr Asn Ser Thr Gln Asn His
220                 225                 230                 235 ttg ctg ctt tcc cag gaa tgt gac agt gcc cat tct ctc cgt ctt gaa     890
Leu Leu Leu Ser Gln Glu Cys Asp Ser Ala His Ser Leu Arg Leu Glu
                240                 245                 250 atg gcc aga gca gga act cac caa gtt tcc atg gaa acc caa gaa tct     938
Met Ala Arg Ala Gly Thr His Gln Val Ser Met Glu Thr Gln Glu Ser
                255                 260                 265 tcc tct aca ctt aca gta gcc agt aga aat agt ccc gct tct cca cta     986
Ser Ser Thr Leu Thr Val Ala Ser Arg Asn Ser Pro Ala Ser Pro Leu
            270                 275                 280 aaa gaa ttg tca gga aaa cta atg aaa agt ata gaa caa gat gca gtg    1034
Lys Glu Leu Ser Gly Lys Leu Met Lys Ser Ile Glu Gln Asp Ala Val
285                 290                 295 aat act ttt acc aaa tat ata tct cca gat gct gct aaa cca ata cca    1082
Asn Thr Phe Thr Lys Tyr Ile Ser Pro Asp Ala Ala Lys Pro Ile Pro
300                 305                 310                 315 att aca gaa gca atg aga aat gac atc ata gca agg att tgt gga gaa    1130
Ile Thr Glu Ala Met Arg Asn Asp Ile Ile Ala Arg Ile Cys Gly Glu
                320                 325                 330 gat gga cag gtg gat ccc aac tgt ttc gtt ttg gca cag tcc ata gtc    1178
Asp Gly Gln Val Asp Pro Asn Cys Phe Val Leu Ala Gln Ser Ile Val
            335                 340                 345 ttt agt gca atg gag caa gag cac ttt agt gag ttt ctg cga agt cac    1226
Phe Ser Ala Met Glu Gln Glu His Phe Ser Glu Phe Leu Arg Ser His
            350                 355                 360 cat ttc tgt aaa tac cag att gaa gtg ctg acc agt gga act gtt tac    1274
His Phe Cys Lys Tyr Gln Ile Glu Val Leu Thr Ser Gly Thr Val Tyr
365                 370                 375 ctg gct gac att ctc ttc tgt gag tca gcc ctc ttt tat ttc tct gag    1322
Leu Ala Asp Ile Leu Phe Cys Glu Ser Ala Leu Phe Tyr Phe Ser Glu
380             385                 390                 395 tac atg gaa aaa gag gat gca gtg aat atc tta caa ttc tgg ttg gca    1370
Tyr Met Glu Lys Glu Asp Ala Val Asn Ile Leu Gln Phe Trp Leu Ala
                400                 405                 410 gca gat aac ttc cag tct cag ctt gct gcc aaa aag ggg caa tat gat    1418
Ala Asp Asn Phe Gln Ser Gln Leu Ala Ala Lys Lys Gly Gln Tyr Asp
                415                 420                 425 gga cag gag gca cag aat gat gcc atg att tta tat gac aag tac ttc    1466
Gly Gln Glu Ala Gln Asn Asp Ala Met Ile Leu Tyr Asp Lys Tyr Phe
            430                 435                 440 tcc ctc caa gcc aca cat cct ctt gga ttt gat gat gtt gta cga tta    1514
```

```
Ser Leu Gln Ala Thr His Pro Leu Gly Phe Asp Asp Val Val Arg Leu
    445                 450                 455
```

| | | | | | | | | | | | | | | | | |
|---|---|---|---|---|---|---|---|---|---|---|---|---|---|---|---|---|
| gaa | att | gaa | tcc | aat | atc | tgc | agg | gaa | ggt | ggg | cca | ctc | ccc | aac | tgt | 1562 |
| Glu | Ile | Glu | Ser | Asn | Ile | Cys | Arg | Glu | Gly | Gly | Pro | Leu | Pro | Asn | Cys | |
| 460 | | | | | 465 | | | | | 470 | | | | | 475 | |
| ttc | aca | act | cca | tta | cgt | cag | gcc | tgg | aca | acc | atg | gag | aag | gtc | ttt | 1610 |
| Phe | Thr | Thr | Pro | Leu | Arg | Gln | Ala | Trp | Thr | Thr | Met | Glu | Lys | Val | Phe | |
| | | | | 480 | | | | | 485 | | | | | 490 | | |
| ttg | cct | ggc | ttt | ctg | tcc | agc | aat | ctt | tat | tat | aaa | tat | ttg | aat | gat | 1658 |
| Leu | Pro | Gly | Phe | Leu | Ser | Ser | Asn | Leu | Tyr | Tyr | Lys | Tyr | Leu | Asn | Asp | |
| | | | 495 | | | | | 500 | | | | | 505 | | | |
| ctc | atc | cat | tcg | gtt | cga | gga | gat | gaa | ttt | ctg | ggc | ggg | aac | gtg | tcg | 1706 |
| Leu | Ile | His | Ser | Val | Arg | Gly | Asp | Glu | Phe | Leu | Gly | Gly | Asn | Val | Ser | |
| | | 510 | | | | | 515 | | | | | 520 | | | | |
| ccg | act | gct | cct | ggc | tct | gtt | ggc | cct | cct | gat | gag | tct | cac | cca | ggg | 1754 |
| Pro | Thr | Ala | Pro | Gly | Ser | Val | Gly | Pro | Pro | Asp | Glu | Ser | His | Pro | Gly | |
| | 525 | | | | | 530 | | | | | 535 | | | | | |
| agt | tct | gac | agc | tct | gcg | tct | cag | tcc | agt | gtg | aaa | aaa | gcc | agt | att | 1802 |
| Ser | Ser | Asp | Ser | Ser | Ala | Ser | Gln | Ser | Ser | Val | Lys | Lys | Ala | Ser | Ile | |
| 540 | | | | | 545 | | | | | 550 | | | | | 555 | |
| aaa | ata | ctg | aaa | aat | ttt | gat | gaa | gcg | ata | att | gtg | gat | gcg | gca | agt | 1850 |
| Lys | Ile | Leu | Lys | Asn | Phe | Asp | Glu | Ala | Ile | Ile | Val | Asp | Ala | Ala | Ser | |
| | | | | 560 | | | | | 565 | | | | | 570 | | |
| ctg | gat | cca | gaa | tct | tta | tat | caa | cgg | aca | tat | gcc | ggg | aag | atg | aca | 1898 |
| Leu | Asp | Pro | Glu | Ser | Leu | Tyr | Gln | Arg | Thr | Tyr | Ala | Gly | Lys | Met | Thr | |
| | | | 575 | | | | | 580 | | | | | 585 | | | |
| ttt | gga | aga | gtg | agt | gac | ttg | ggg | caa | ttc | atc | cgg | gaa | tct | gag | cct | 1946 |
| Phe | Gly | Arg | Val | Ser | Asp | Leu | Gly | Gln | Phe | Ile | Arg | Glu | Ser | Glu | Pro | |
| | | 590 | | | | | 595 | | | | | 600 | | | | |
| gaa | cct | gat | gta | agg | aaa | tca | aaa | gga | tcc | atg | ttc | tca | caa | gct | atg | 1994 |
| Glu | Pro | Asp | Val | Arg | Lys | Ser | Lys | Gly | Ser | Met | Phe | Ser | Gln | Ala | Met | |
| | 605 | | | | | 610 | | | | | 615 | | | | | |
| aag | aaa | tgg | gtg | caa | gga | aat | act | gat | gag | gcc | cag | gaa | gag | cta | gct | 2042 |
| Lys | Lys | Trp | Val | Gln | Gly | Asn | Thr | Asp | Glu | Ala | Gln | Glu | Glu | Leu | Ala | |
| 620 | | | | | 625 | | | | | 630 | | | | | 635 | |
| tgg | aag | att | gct | aaa | atg | ata | gtc | agt | gac | att | atg | cag | cag | gct | cag | 2090 |
| Trp | Lys | Ile | Ala | Lys | Met | Ile | Val | Ser | Asp | Ile | Met | Gln | Gln | Ala | Gln | |
| | | | | 640 | | | | | 645 | | | | | 650 | | |
| tat | gat | caa | ccg | tta | gag | aaa | tct | aca | aag | tta | tga | ctcaaaactt | | | | 2136 |
| Tyr | Asp | Gln | Pro | Leu | Glu | Lys | Ser | Thr | Lys | Leu | * | | | | | |
| | | | 655 | | | | | 660 | | | | | | | | |

```
gagataaagg aaatctgctt gtgaaaaata agagaacttt tttcccttgg ttggattctt     2196
caacacagcc aatgaaaaca gcactatatt tctgatctgt cactgttgtt tccagggaga     2256
gaatggggag acaatcctag gacttccacc ctaatgcagt tacctgtagg gcataattgg     2316
atggcacatg atgtttcaca cagtgaggag tctttaaagg ttaccaa                   2363

<210> SEQ ID NO 64
<211> LENGTH: 662
<212> TYPE: PRT
<213> ORGANISM: Homo sapiens

<400> SEQUENCE: 64

Met Arg Gly Ala Gly Pro Ser Pro Arg Gln Ser Pro Arg Thr Leu Arg
 1               5                  10                  15

Pro Asp Pro Gly Pro Ala Met Ser Phe Phe Arg Arg Lys Val Lys Gly
                20                  25                  30

Lys Glu Gln Glu Lys Thr Ser Asp Val Lys Ser Ile Lys Ala Ser Ile
            35                  40                  45
```

```
Ser Val His Ser Pro Gln Lys Ser Thr Lys Asn His Ala Leu Leu Glu
    50                  55                  60

Ala Ala Gly Pro Ser His Val Ala Ile Asn Ala Ile Ser Ala Asn Met
65                  70                  75                  80

Asp Ser Phe Ser Ser Arg Thr Ala Thr Leu Lys Lys Gln Pro Ser
                85                  90                  95

His Met Glu Ala Ala His Phe Gly Asp Leu Gly Arg Ser Cys Leu Asp
            100                 105                 110

Tyr Gln Thr Gln Glu Thr Lys Ser Ser Leu Ser Lys Thr Leu Glu Gln
                115                 120                 125

Val Leu His Asp Thr Ile Val Leu Pro Tyr Phe Ile Gln Phe Met Glu
    130                 135                 140

Leu Arg Arg Met Glu His Leu Val Lys Phe Trp Leu Glu Ala Glu Ser
145                 150                 155                 160

Phe His Ser Thr Thr Trp Ser Arg Ile Arg Ala His Ser Leu Asn Thr
                165                 170                 175

Met Lys Gln Ser Ser Leu Ala Glu Pro Val Ser Pro Ser Lys Lys His
            180                 185                 190

Glu Thr Thr Ala Ser Phe Leu Thr Asp Ser Leu Asp Lys Arg Leu Glu
        195                 200                 205

Asp Ser Gly Ser Ala Gln Leu Phe Met Thr His Ser Glu Gly Ile Asp
    210                 215                 220

Leu Asn Asn Arg Thr Asn Ser Thr Gln Asn His Leu Leu Leu Ser Gln
225                 230                 235                 240

Glu Cys Asp Ser Ala His Ser Leu Arg Leu Glu Met Ala Arg Ala Gly
                245                 250                 255

Thr His Gln Val Ser Met Glu Thr Gln Glu Ser Ser Ser Thr Leu Thr
            260                 265                 270

Val Ala Ser Arg Asn Ser Pro Ala Ser Pro Leu Lys Glu Leu Ser Gly
        275                 280                 285

Lys Leu Met Lys Ser Ile Glu Gln Asp Ala Val Asn Thr Phe Thr Lys
290                 295                 300

Tyr Ile Ser Pro Asp Ala Ala Lys Pro Ile Pro Ile Thr Glu Ala Met
305                 310                 315                 320

Arg Asn Asp Ile Ile Ala Arg Ile Cys Gly Glu Asp Gly Gln Val Asp
                325                 330                 335

Pro Asn Cys Phe Val Leu Ala Gln Ser Ile Val Phe Ser Ala Met Glu
            340                 345                 350

Gln Glu His Phe Ser Glu Phe Leu Arg Ser His His Phe Cys Lys Tyr
                355                 360                 365

Gln Ile Glu Val Leu Thr Ser Gly Thr Val Tyr Leu Ala Asp Ile Leu
    370                 375                 380

Phe Cys Glu Ser Ala Leu Phe Tyr Phe Ser Glu Tyr Met Glu Lys Glu
385                 390                 395                 400

Asp Ala Val Asn Ile Leu Gln Phe Trp Leu Ala Ala Asp Asn Phe Gln
                405                 410                 415

Ser Gln Leu Ala Ala Lys Lys Gly Gln Tyr Asp Gly Gln Glu Ala Gln
            420                 425                 430

Asn Asp Ala Met Ile Leu Tyr Asp Lys Tyr Phe Ser Leu Gln Ala Thr
        435                 440                 445

His Pro Leu Gly Phe Asp Asp Val Val Arg Leu Glu Ile Glu Ser Asn
    450                 455                 460
```

```
Ile Cys Arg Glu Gly Gly Pro Leu Pro Asn Cys Phe Thr Thr Pro Leu
465                 470                 475                 480

Arg Gln Ala Trp Thr Thr Met Glu Lys Val Phe Leu Pro Gly Phe Leu
                485                 490                 495

Ser Ser Asn Leu Tyr Tyr Lys Tyr Leu Asn Asp Leu Ile His Ser Val
            500                 505                 510

Arg Gly Asp Glu Phe Leu Gly Gly Asn Val Ser Pro Thr Ala Pro Gly
        515                 520                 525

Ser Val Gly Pro Pro Asp Glu Ser His Pro Gly Ser Ser Asp Ser Ser
    530                 535                 540

Ala Ser Gln Ser Ser Val Lys Lys Ala Ser Ile Lys Ile Leu Lys Asn
545                 550                 555                 560

Phe Asp Glu Ala Ile Ile Val Asp Ala Ala Ser Leu Asp Pro Glu Ser
                565                 570                 575

Leu Tyr Gln Arg Thr Tyr Ala Gly Lys Met Thr Phe Gly Arg Val Ser
            580                 585                 590

Asp Leu Gly Gln Phe Ile Arg Glu Ser Glu Pro Glu Pro Asp Val Arg
        595                 600                 605

Lys Ser Lys Gly Ser Met Phe Ser Gln Ala Met Lys Lys Trp Val Gln
        610                 615                 620

Gly Asn Thr Asp Glu Ala Gln Glu Glu Leu Ala Trp Lys Ile Ala Lys
625                 630                 635                 640

Met Ile Val Ser Asp Ile Met Gln Gln Ala Gln Tyr Asp Gln Pro Leu
                645                 650                 655

Glu Lys Ser Thr Lys Leu
                660

<210> SEQ ID NO 65
<211> LENGTH: 662
<212> TYPE: PRT
<213> ORGANISM: Homo sapiens

<400> SEQUENCE: 65

Met Arg Gly Ala Gly Pro Ser Pro Arg Gln Ser Pro Arg Thr Leu Arg
1               5                   10                  15

Pro Asp Pro Gly Pro Ala Met Ser Phe Phe Arg Arg Lys Val Lys Gly
            20                  25                  30

Lys Glu Gln Glu Lys Thr Ser Asp Val Lys Ser Ile Lys Ala Ser Ile
        35                  40                  45

Ser Val His Ser Pro Gln Lys Ser Thr Lys Asn His Ala Leu Leu Glu
    50                  55                  60

Ala Ala Gly Pro Ser His Val Ala Ile Asn Ala Ile Ser Ala Asn Met
65                  70                  75                  80

Asp Ser Phe Ser Ser Ser Arg Thr Ala Thr Leu Lys Lys Gln Pro Ser
                85                  90                  95

His Met Glu Ala Ala His Phe Gly Asp Leu Gly Arg Ser Cys Leu Asp
            100                 105                 110

Tyr Gln Thr Gln Glu Thr Lys Ser Ser Leu Ser Lys Thr Leu Glu Gln
        115                 120                 125

Val Leu His Asp Thr Ile Val Leu Pro Tyr Phe Ile Gln Phe Met Glu
    130                 135                 140

Leu Arg Arg Met Glu His Leu Val Lys Phe Trp Leu Glu Ala Glu Ser
145                 150                 155                 160

Phe His Ser Thr Thr Trp Ser Arg Ile Arg Ala His Ser Leu Asn Thr
                165                 170                 175
```

```
Met Lys Gln Ser Ser Leu Ala Glu Pro Val Ser Pro Ser Lys Lys His
            180                 185                 190

Glu Thr Thr Ala Ser Phe Leu Thr Asp Ser Leu Asp Lys Arg Leu Glu
            195                 200                 205

Asp Ser Gly Ser Ala Gln Leu Phe Met Thr His Ser Glu Gly Ile Asp
    210                 215                 220

Leu Asn Asn Arg Thr Asn Ser Thr Gln Asn His Leu Leu Leu Ser Gln
225                 230                 235                 240

Glu Cys Asp Ser Ala His Ser Leu Arg Leu Glu Met Ala Arg Ala Gly
                245                 250                 255

Thr His Gln Val Ser Met Glu Thr Gln Glu Ser Ser Thr Leu Thr
            260                 265                 270

Val Ala Ser Arg Asn Ser Pro Ala Ser Pro Leu Lys Glu Leu Ser Gly
            275                 280                 285

Lys Leu Met Lys Ser Ile Glu Gln Asp Ala Val Asn Thr Phe Thr Lys
    290                 295                 300

Tyr Ile Ser Pro Asp Ala Ala Lys Pro Ile Pro Ile Thr Glu Ala Met
305                 310                 315                 320

Arg Asn Asp Ile Ile Ala Arg Ile Cys Gly Glu Asp Gly Gln Val Asp
                325                 330                 335

Pro Asn Cys Phe Val Leu Ala Gln Ser Ile Val Phe Ser Ala Met Glu
            340                 345                 350

Gln Glu His Phe Ser Glu Phe Leu Arg Ser His His Phe Cys Lys Tyr
            355                 360                 365

Gln Ile Glu Val Leu Thr Ser Gly Thr Val Tyr Leu Ala Asp Ile Leu
    370                 375                 380

Phe Cys Glu Ser Ala Leu Phe Tyr Phe Ser Glu Tyr Met Glu Lys Glu
385                 390                 395                 400

Asp Ala Val Asn Ile Leu Gln Phe Trp Leu Ala Ala Asp Asn Phe Gln
                405                 410                 415

Ser Gln Leu Ala Ala Lys Lys Gly Gln Tyr Asp Gly Gln Glu Ala Gln
            420                 425                 430

Asn Asp Ala Met Ile Leu Tyr Asp Lys Tyr Phe Ser Leu Gln Ala Thr
            435                 440                 445

His Pro Leu Gly Phe Asp Asp Val Val Arg Leu Glu Ile Glu Ser Asn
    450                 455                 460

Ile Cys Arg Glu Gly Gly Pro Leu Pro Asn Cys Phe Thr Thr Pro Leu
465                 470                 475                 480

Arg Gln Ala Trp Thr Thr Met Glu Lys Val Phe Leu Pro Gly Phe Leu
                485                 490                 495

Ser Ser Asn Leu Tyr Tyr Lys Tyr Leu Asn Asp Leu Ile His Ser Val
            500                 505                 510

Arg Gly Asp Glu Phe Leu Gly Gly Asn Val Ser Pro Thr Ala Pro Gly
            515                 520                 525

Ser Val Gly Pro Pro Asp Glu Ser His Pro Gly Ser Ser Asp Ser Ser
    530                 535                 540

Ala Ser Gln Ser Ser Val Lys Lys Ala Ser Ile Lys Ile Leu Lys Asn
545                 550                 555                 560

Phe Asp Glu Ala Ile Ile Val Asp Ala Ala Ser Leu Asp Pro Glu Ser
                565                 570                 575

Leu Tyr Gln Arg Thr Tyr Ala Gly Lys Met Thr Phe Gly Arg Val Ser
            580                 585                 590
```

```
Asp Leu Gly Gln Phe Ile Arg Glu Ser Glu Pro Glu Pro Asp Val Arg
        595                 600                 605

Lys Ser Lys Gly Ser Met Phe Ser Gln Ala Met Lys Lys Trp Val Gln
    610                 615                 620

Gly Asn Thr Asp Glu Ala Gln Glu Glu Leu Ala Trp Lys Ile Ala Lys
625                 630                 635                 640

Met Ile Val Ser Asp Val Met Gln Gln Ala Gln Tyr Asp Gln Pro Leu
                645                 650                 655

Glu Lys Ser Thr Lys Leu
            660

<210> SEQ ID NO 66
<211> LENGTH: 26
<212> TYPE: PRT
<213> ORGANISM: Homo sapiens

<400> SEQUENCE: 66

Gln Gly Asn Thr Asp Glu Ala Gln Glu Glu Leu Ala Trp Lys Ile Ala
1               5                   10                  15

Lys Met Ile Val Ser Asp Ile Met Gln Gln
            20                  25

<210> SEQ ID NO 67
<211> LENGTH: 25
<212> TYPE: PRT
<213> ORGANISM: Homo sapiens

<400> SEQUENCE: 67

Gly Asn Thr Asp Glu Ala Gln Glu Glu Leu Ala Trp Lys Ile Ala Lys
1               5                   10                  15

Met Ile Val Ser Asp Ile Met Gln Gln
            20                  25

<210> SEQ ID NO 68
<211> LENGTH: 24
<212> TYPE: PRT
<213> ORGANISM: Homo sapiens

<400> SEQUENCE: 68

Asn Thr Asp Glu Ala Gln Glu Glu Leu Ala Trp Lys Ile Ala Lys Met
1               5                   10                  15

Ile Val Ser Asp Ile Met Gln Gln
            20

<210> SEQ ID NO 69
<211> LENGTH: 23
<212> TYPE: PRT
<213> ORGANISM: Homo sapiens

<400> SEQUENCE: 69

Thr Asp Glu Ala Gln Glu Glu Leu Ala Trp Lys Ile Ala Lys Met Ile
1               5                   10                  15

Val Ser Asp Ile Met Gln Gln
            20

<210> SEQ ID NO 70
<211> LENGTH: 22
<212> TYPE: PRT
<213> ORGANISM: Homo sapiens

<400> SEQUENCE: 70
```

Asp Glu Ala Gln Glu Glu Leu Ala Trp Lys Ile Ala Lys Met Ile Val
1               5                   10                  15

Ser Asp Ile Met Gln Gln
            20

<210> SEQ ID NO 71
<211> LENGTH: 21
<212> TYPE: PRT
<213> ORGANISM: Homo sapiens

<400> SEQUENCE: 71

Glu Ala Gln Glu Glu Leu Ala Trp Lys Ile Ala Lys Met Ile Val Ser
1               5                   10                  15

Asp Ile Met Gln Gln
            20

<210> SEQ ID NO 72
<211> LENGTH: 20
<212> TYPE: PRT
<213> ORGANISM: Homo sapiens

<400> SEQUENCE: 72

Ala Gln Glu Glu Leu Ala Trp Lys Ile Ala Lys Met Ile Val Ser Asp
1               5                   10                  15

Ile Met Gln Gln
            20

<210> SEQ ID NO 73
<211> LENGTH: 19
<212> TYPE: PRT
<213> ORGANISM: Homo sapiens

<400> SEQUENCE: 73

Gln Glu Glu Leu Ala Trp Lys Ile Ala Lys Met Ile Val Ser Asp Ile
1               5                   10                  15

Met Gln Gln
20

<210> SEQ ID NO 74
<211> LENGTH: 18
<212> TYPE: PRT
<213> ORGANISM: Homo sapiens

<400> SEQUENCE: 74

Glu Glu Leu Ala Trp Lys Ile Ala Lys Met Ile Val Ser Asp Ile Met
1               5                   10                  15

Gln Gln
20

<210> SEQ ID NO 75
<211> LENGTH: 17
<212> TYPE: PRT
<213> ORGANISM: Homo sapiens

<400> SEQUENCE: 75

Glu Leu Ala Trp Lys Ile Ala Lys Met Ile Val Ser Asp Ile Met Gln
1               5                   10                  15

Gln

<210> SEQ ID NO 76
<211> LENGTH: 16
<212> TYPE: PRT
<213> ORGANISM: Homo sapiens

<400> SEQUENCE: 76

Leu Ala Trp Lys Ile Ala Lys Met Ile Val Ser Asp Ile Met Gln Gln
 1               5                  10                  15

<210> SEQ ID NO 77
<211> LENGTH: 15
<212> TYPE: PRT
<213> ORGANISM: Homo sapiens

<400> SEQUENCE: 77

Ala Trp Lys Ile Ala Lys Met Ile Val Ser Asp Ile Met Gln Gln
 1               5                  10                  15

<210> SEQ ID NO 78
<211> LENGTH: 14
<212> TYPE: PRT
<213> ORGANISM: Homo sapiens

<400> SEQUENCE: 78

Trp Lys Ile Ala Lys Met Ile Val Ser Asp Ile Met Gln Gln
 1               5                  10

<210> SEQ ID NO 79
<211> LENGTH: 13
<212> TYPE: PRT
<213> ORGANISM: Homo sapiens

<400> SEQUENCE: 79

Lys Ile Ala Lys Met Ile Val Ser Asp Ile Met Gln Gln
 1               5                  10

<210> SEQ ID NO 80
<211> LENGTH: 12
<212> TYPE: PRT
<213> ORGANISM: Homo sapiens

<400> SEQUENCE: 80

Ile Ala Lys Met Ile Val Ser Asp Ile Met Gln Gln
 1               5                  10

<210> SEQ ID NO 81
<211> LENGTH: 11
<212> TYPE: PRT
<213> ORGANISM: Homo sapiens

<400> SEQUENCE: 81

Ala Lys Met Ile Val Ser Asp Ile Met Gln Gln
 1               5                  10

<210> SEQ ID NO 82
<211> LENGTH: 10
<212> TYPE: PRT
<213> ORGANISM: Homo sapiens

<400> SEQUENCE: 82

Lys Met Ile Val Ser Asp Ile Met Gln Gln
 1               5                  10

<210> SEQ ID NO 83
<211> LENGTH: 26
<212> TYPE: PRT
<213> ORGANISM: Homo sapiens

<400> SEQUENCE: 83

-continued

Val Gln Gly Asn Thr Asp Glu Ala Gln Glu Glu Leu Ala Trp Lys Ile
1               5                   10                  15

Ala Lys Met Ile Val Ser Asp Ile Met Gln
            20                  25

<210> SEQ ID NO 84
<211> LENGTH: 25
<212> TYPE: PRT
<213> ORGANISM: Homo sapiens

<400> SEQUENCE: 84

Val Gln Gly Asn Thr Asp Glu Ala Gln Glu Glu Leu Ala Trp Lys Ile
1               5                   10                  15

Ala Lys Met Ile Val Ser Asp Ile Met
            20                  25

<210> SEQ ID NO 85
<211> LENGTH: 24
<212> TYPE: PRT
<213> ORGANISM: Homo sapiens

<400> SEQUENCE: 85

Val Gln Gly Asn Thr Asp Glu Ala Gln Glu Glu Leu Ala Trp Lys Ile
1               5                   10                  15

Ala Lys Met Ile Val Ser Asp Ile
            20

<210> SEQ ID NO 86
<211> LENGTH: 23
<212> TYPE: PRT
<213> ORGANISM: Homo sapiens

<400> SEQUENCE: 86

Val Gln Gly Asn Thr Asp Glu Ala Gln Glu Glu Leu Ala Trp Lys Ile
1               5                   10                  15

Ala Lys Met Ile Val Ser Asp
            20

<210> SEQ ID NO 87
<211> LENGTH: 22
<212> TYPE: PRT
<213> ORGANISM: Homo sapiens

<400> SEQUENCE: 87

Val Gln Gly Asn Thr Asp Glu Ala Gln Glu Glu Leu Ala Trp Lys Ile
1               5                   10                  15

Ala Lys Met Ile Val Ser
            20

<210> SEQ ID NO 88
<211> LENGTH: 21
<212> TYPE: PRT
<213> ORGANISM: Homo sapiens

<400> SEQUENCE: 88

Val Gln Gly Asn Thr Asp Glu Ala Gln Glu Glu Leu Ala Trp Lys Ile
1               5                   10                  15

Ala Lys Met Ile Val
            20

<210> SEQ ID NO 89

```
<211> LENGTH: 20
<212> TYPE: PRT
<213> ORGANISM: Homo sapiens

<400> SEQUENCE: 89

Val Gln Gly Asn Thr Asp Glu Ala Gln Glu Glu Leu Ala Trp Lys Ile
1               5                   10                  15
Ala Lys Met Ile
            20

<210> SEQ ID NO 90
<211> LENGTH: 19
<212> TYPE: PRT
<213> ORGANISM: Homo sapiens

<400> SEQUENCE: 90

Val Gln Gly Asn Thr Asp Glu Ala Gln Glu Glu Leu Ala Trp Lys Ile
1               5                   10                  15
Ala Lys Met

<210> SEQ ID NO 91
<211> LENGTH: 18
<212> TYPE: PRT
<213> ORGANISM: Homo sapiens

<400> SEQUENCE: 91

Val Gln Gly Asn Thr Asp Glu Ala Gln Glu Glu Leu Ala Trp Lys Ile
1               5                   10                  15
Ala Lys

<210> SEQ ID NO 92
<211> LENGTH: 17
<212> TYPE: PRT
<213> ORGANISM: Homo sapiens

<400> SEQUENCE: 92

Val Gln Gly Asn Thr Asp Glu Ala Gln Glu Glu Leu Ala Trp Lys Ile
1               5                   10                  15
Ala

<210> SEQ ID NO 93
<211> LENGTH: 16
<212> TYPE: PRT
<213> ORGANISM: Homo sapiens

<400> SEQUENCE: 93

Val Gln Gly Asn Thr Asp Glu Ala Gln Glu Glu Leu Ala Trp Lys Ile
1               5                   10                  15

<210> SEQ ID NO 94
<211> LENGTH: 15
<212> TYPE: PRT
<213> ORGANISM: Homo sapiens

<400> SEQUENCE: 94

Val Gln Gly Asn Thr Asp Glu Ala Gln Glu Glu Leu Ala Trp Lys
1               5                   10                  15

<210> SEQ ID NO 95
<211> LENGTH: 14
<212> TYPE: PRT
<213> ORGANISM: Homo sapiens
```

```
<400> SEQUENCE: 95

Val Gln Gly Asn Thr Asp Glu Ala Gln Glu Leu Ala Trp
1               5                   10

<210> SEQ ID NO 96
<211> LENGTH: 13
<212> TYPE: PRT
<213> ORGANISM: Homo sapiens

<400> SEQUENCE: 96

Val Gln Gly Asn Thr Asp Glu Ala Gln Glu Leu Ala
1               5                   10

<210> SEQ ID NO 97
<211> LENGTH: 12
<212> TYPE: PRT
<213> ORGANISM: Homo sapiens

<400> SEQUENCE: 97

Val Gln Gly Asn Thr Asp Glu Ala Gln Glu Leu
1               5                   10

<210> SEQ ID NO 98
<211> LENGTH: 11
<212> TYPE: PRT
<213> ORGANISM: Homo sapiens

<400> SEQUENCE: 98

Val Gln Gly Asn Thr Asp Glu Ala Gln Glu
1               5                   10

<210> SEQ ID NO 99
<211> LENGTH: 10
<212> TYPE: PRT
<213> ORGANISM: Homo sapiens

<400> SEQUENCE: 99

Val Gln Gly Asn Thr Asp Glu Ala Gln Glu
1               5                   10

<210> SEQ ID NO 100
<211> LENGTH: 27
<212> TYPE: PRT
<213> ORGANISM: Homo sapiens

<400> SEQUENCE: 100

Val Gln Gly Asn Thr Asp Glu Ala Gln Glu Leu Ala Trp Lys Ile
1               5                   10                  15

Glu Lys Met Ile Trp Ser Asp Val Met Gln Gln
            20                  25

<210> SEQ ID NO 101
<211> LENGTH: 27
<212> TYPE: PRT
<213> ORGANISM: Homo sapiens

<400> SEQUENCE: 101

Val Gln Gly Asn Thr Asp Glu Ala Gln Glu Leu Ala Trp Lys Ile
1               5                   10                  15

Ala Lys Met Ile Trp Ser Asp Val Met Gln Gln
            20                  25

<210> SEQ ID NO 102
```

```
<211> LENGTH: 17
<212> TYPE: PRT
<213> ORGANISM: Homo sapiens
<220> FEATURE:
<221> NAME/KEY: ACETYLATION
<222> LOCATION: (1)...(1)

<400> SEQUENCE: 102

Asp Leu Ala Trp Lys Ile Ala Lys Met Ile Val Ser Asp Val Met Gln
1               5                   10                  15

Gln

<210> SEQ ID NO 103
<211> LENGTH: 20
<212> TYPE: PRT
<213> ORGANISM: Homo sapiens

<400> SEQUENCE: 103

Phe Glu Glu Leu Ala Trp Lys Ile Ala Lys Met Ile Trp Ser Asp Val
1               5                   10                  15

Phe Gln Gln Cys
            20

<210> SEQ ID NO 104
<211> LENGTH: 20
<212> TYPE: PRT
<213> ORGANISM: Homo sapiens

<400> SEQUENCE: 104

Phe Glu Glu Leu Ala Trp Lys Ile Ala Lys Met Ile Trp Ser Asp Val
1               5                   10                  15

Met Gln Gln Cys
            20

<210> SEQ ID NO 105
<211> LENGTH: 20
<212> TYPE: PRT
<213> ORGANISM: Homo sapiens

<400> SEQUENCE: 105

Gln Glu Glu Phe Ala Trp Lys Ile Ala Lys Met Ile Val Ser Asp Val
1               5                   10                  15

Phe Gln Gln Cys
            20

<210> SEQ ID NO 106
<211> LENGTH: 20
<212> TYPE: PRT
<213> ORGANISM: Homo sapiens

<400> SEQUENCE: 106

Gln Glu Glu Phe Ala Trp Lys Ile Ala Lys Met Ile Ile Ser Asp Val
1               5                   10                  15

Phe Gln Gln Cys
            20

<210> SEQ ID NO 107
<211> LENGTH: 20
<212> TYPE: PRT
<213> ORGANISM: Homo sapiens

<400> SEQUENCE: 107
```

-continued

```
Phe Glu Glu Leu Ala Trp Lys Ile Ala Lys Met Ile Ile Ser Asp Val
1               5                   10                  15

Phe Gln Gln Cys
            20

<210> SEQ ID NO 108
<211> LENGTH: 28
<212> TYPE: PRT
<213> ORGANISM: Homo sapiens

<400> SEQUENCE: 108

Val Gln Gly Asn Thr Asp Glu Ala Gln Glu Leu Ala Trp Lys Ile
1               5                   10                  15

Ala Lys Met Ile Val Ser Asp Val Met Gln Gln Cys
            20                  25

<210> SEQ ID NO 109
<211> LENGTH: 28
<212> TYPE: PRT
<213> ORGANISM: Homo sapiens

<400> SEQUENCE: 109

Val Gln Gly Asn Thr Asp Glu Ala Gln Glu Glu Leu Leu Trp Lys Ile
1               5                   10                  15

Ala Lys Met Ile Val Ser Asp Val Met Gln Gln Cys
            20                  25

<210> SEQ ID NO 110
<211> LENGTH: 28
<212> TYPE: PRT
<213> ORGANISM: Homo sapiens

<400> SEQUENCE: 110

Val Gln Gly Asn Thr Asp Glu Ala Gln Glu Glu Leu Ala Trp Lys Ile
1               5                   10                  15

Glu Lys Met Ile Trp Ser Asp Val Met Gln Gln Cys
            20                  25

<210> SEQ ID NO 111
<211> LENGTH: 28
<212> TYPE: PRT
<213> ORGANISM: Homo sapiens

<400> SEQUENCE: 111

Val Gln Gly Asn Thr Asp Glu Ala Gln Glu Leu Ala Trp Lys Ile
1               5                   10                  15

Ala Lys Met Ile Trp Ser Asp Val Met Gln Gln Cys
            20                  25

<210> SEQ ID NO 112
<211> LENGTH: 18
<212> TYPE: PRT
<213> ORGANISM: Homo sapiens
<220> FEATURE:
<221> NAME/KEY: ACETYLATION
<222> LOCATION: (1)...(1)

<400> SEQUENCE: 112

Asp Leu Ala Trp Lys Ile Ala Lys Met Ile Val Ser Asp Val Met Gln
1               5                   10                  15

Gln Cys
```

KINASE ANCHOR PROTEIN MUTEINS, PEPTIDES THEREOF AND RELATED DOCUMENTS

RELATED APPLICATIONS

Benefit of priority under § 119(e) is claimed to U.S. Provisional Application Ser. No. 60/377,852, entitled "Kinase Anchor Protein Muteins, Peptides Thereof, and Related Methods", filed May 3, 2002, and to U.S. Provisional Application Ser. No. 60/453,408, entitled "Kinase Anchor Protein Muteins, Peptides Thereof, and Related Methods", filed Mar. 7, 2003. The subject matter of each of these provisional applications is incorporated in its entirety by reference thereto.

This application is also related to International PCT application No. PCT/US03/13698, filed on the same day herewith, entitled "Kinase Anchor Protein Muteins, Peptides Thereof, and Related Methods." The disclosure of the PCT application is herein incorporated by reference in its entirety.

Work described herein was supported by NIH grants DK-54441 and 5T32 DK-07233. The government may have certain rights in subject matter provided herein.

FIELD OF THE INVENTION

A-kinase anchor protein (AKAPs) muteins, peptides thereof, and nucleic acids encoding the peptides are provided herein.

BACKGROUND OF THE INVENTION

Protein phosphorylation is an important mechanism for enzyme regulation and the transduction of extracellular signals across the cell membrane in eukaryotic cells. A wide variety of cellular substrates, including enzymes, membrane receptors, ion channels and transcription factors, can be phosphorylated in response to extracellular signals that interact with cells. A key enzyme in the phosphorylation of cellular proteins in response to hormones and neurotransmitters is cyclic AMP (cAMP)-dependent protein kinase (PKA). Upon activation by cAMP, PKA thus mediates a variety of cellular responses to such extracellular signals.

An array of PKA isozymes are expressed in mammalian cells. The PKA holoenzymes usually exist as inactive tetramers containing a regulatory (R) subunit dimer and two catalytic (C) subunits. Genes encoding three C subunits (Cα, Cβ and Cγ) and four R subunits (RIα, RIβ, RIIα and RIIβ) have been identified (see Takio et al. (1982) *Proc. Natl. Acad. Sci. USA*, 79:2544-2548; Lee et al. (1983) *Proc. Natl. Acad. Sci. USA*, 80:3608-3612; Jahnsen et al. (1996) *J. Biol. Chem.*, 261:12352-12361; Clegg et al. (1988) *Proc. Natl. Acad. Sci. USA*, 85:3703-3707; and Scott (1991) *Pharmacol. Ther.*, 50:123-145). The type I (RI) α and type II (RII) α subunits are distributed ubiquitously, whereas RIβ and RIIβ are present mainly in brain (see. e.g., Miki and Eddy (1999) *J. Biol. Chem.*, 274:29057-29062). The type I PKA holoenzyme (RIα and RIβ) is predominantly cytoplasmic, whereas the majority of type II PKA (RIIα and RIIβ) associates with cellular structures and organelles (Scott (1991) *Pharmacol. Ther.*, 50:123-145). Many hormones and other signals act through receptors to generate cAMP which binds to the R subunits of PKA and releases and activates the C subunits to phosphorylate proteins.

Because protein kinases and their substrates are widely distributed throughout cells, there are mechanisms in place in cells to localize protein kinase-mediated responses to different signals. One such mechanism involves subcellular targeting of PKAs through association with anchoring proteins, referred to as A-kinase anchoring proteins (AKAPs), that place PKAs in close proximity to specific organelles or cytoskeletal components and particular substrates, thereby providing for more specific PKA interactions and localized responses (see, e.g., Scott et al. (1990) *J. Biol. Chem.*, 265: 21561-21566; Bregman et al. (1991) *J. Biol. Chem.*, 266: 7207-7213; and Miki and Eddy (1999) *J. Biol. Chem.*, 274: 29057-29062). Anchoring not only places the kinase close to preferred substrates, but also positions the PKA holoenzyme at sites where it can optimally respond to fluctuations in the second messenger cAMP (Mochly-Rosen (1995) *Science*, 268:247-251; Faux and Scott (1996) *Trends Biochem. Sci.*, 21:312-315; Hubbard and Cohen (1993) *Trends Biochem. Sci.*, 18:172-177).

Up to 75% of type II PKA is localized to various intracellular sites through association of the regulatory subunit (RII) with AKAPs (see, e.g., Hausken et al. (1996) *J. Biol. Chem.*, 271:29016-29022). RII subunits of PKA bind to AKAPs with nanomolar affinity (Carr et al. (1992) *J. Biol. Chem.*, 267: 13376-13382), and many AKAP-RII complexes have been isolated from cell extracts. RI subunits of PKA bind to AKAPs with only micromolar affinity (Burton et al. (1997) *Proc. Natl. Acad. Sci. USA* 94:11067-11072). Evidence of binding of a PKA RI subunit to an AKAP has been reported (Miki and Eddy (1998) *J. Biol. Chem.*, 273:34384-34390) in which RIα-specific and RIα/RIIα dual specificity PKA anchoring domains were identified on FSC1/AKAP82. Additional dual specific AKAPs, referred to as D-AKAP1 and D-AKAP2, which interact with the type I and type II regulatory subunits of PKA have also been reported (Huang et al. (1997) *J. Biol. Chem.*, 272:8057-8064; Huang et al. (1997) *Proc. Natl. Acad. Sci. USA*, 94:11184-11189).

More than 20 AKAPs have been reported in different tissues and species. Complementary DNAs (cDNAs) encoding AKAPs have been isolated from diverse species, ranging from *Caenorhabditis elegans* and *Drosophilia* to human (see, e.g., Colledge and Scott (1999) *Trends Cell Biol.*, 9:216-221). Regions within AKAPs that mediate association with RII subunits of PKA have been identified. These regions of approximately 10-18 amino acid residues vary substantially in primary sequence, but secondary structure predictions indicate that they are likely to form an amphipathic helix with hydrophobic residues aligned along one face of the helix and charged residues along the other (Carr et al. (1991) *J. Biol. Chem.*, 266:14188-14192; Carr et al. (1992) *J. Biol. Chem.*, 267:13376-13382). Hydrophobic amino acids with a long aliphatic side chain, e.g., valine, leucine or isoleucine, may participate in binding to RII subunits (Glantz et al. (1993) *J. Biol. Chem.*, 268:12796-12804).

Many AKAPs also have the ability to bind to multiple proteins, including other signalling enzymes. For example, AKAP79 binds to PKA, protein kinase C (PKC) and the protein phosphatase calcineurin (PP2B) (Coghlan et al. (1995) *Science*, 267:108-112 and Klauck et al. (1996) *Science*, 271:1589-1592). Therefore, the targeting of AKAP79 to neuronal postsynaptic membranes brings together enzymes with opposite catalytic activities in a single complex.

AKAPs thus serve as potential regulatory mechanisms that increase the selectivity and intensity of a cAMP-mediated response. There is a need, therefore, to identify and elucidate the structural and functional properties of AKAPs in order to gain a complete understanding of the important role these proteins play in the basic functioning of cells.

SUMMARY OF THE INVENTION

Provided herein are D-AKAP2 peptide muteins that exhibit modified binding to a regulatory subunit of PKA compared to native D-AKAP2. Also provided herein are transgenic animals and cells comprising the peptides provided herein. In one embodiment, the peptides exhibit a preferred or exclusive binding to PKA-RIα subunits relative to PKA-RIIα subunits; or enhanced binding to both RIα and RIIα subunits. In another embodiment, the peptides exhibit a preferred or exclusive binding to PKA-RIIα subunits relative to PKA-RIα subunits.

The peptides provided herein are useful to disrupt, e.g., in vitro, the binding of particular isoforms of PKA, e.g., PKA-RIα or PKA-RIIα, to D-AKAP2. For example, peptides provided herein having enhanced ability to bind to either one of PKA-RIα or PKA-RIIα isoforms are useful to competitively bind to their target PKA isoform and so prevent binding of the particular PKA isoform to its target protein D-AKAP2. In a particular embodiment, the enhanced binder for one PKA isoform that binds weakly to the other isoform (e.g., VQGNT-DEAQEELAWKIAKMIWSD[I/V]MQQ; SEQ ID NOs:54 and 101, which binds tightly to PKA-RIα and weakly to PKA-RIIα; see Table 8) is employed to specifically knock out a specific function of one particular isoform mediated by D-AKAP2.

The peptides provided herein that have a combination of one, two or more specific amino acid changes relative to unmodified native protein sequences can also be used to specifically design peptide mimetics (peptidomimetics) or other small molecules to modulate the D-AKAP2-mediated biological function within cells or organisms. This change of function is contemplated herein to treat medical conditions like heart failure, arrhythmias, or prevent sudden death syndrome. In addition, the binding properties of the peptides provided herein are useful to design and establish high-throughput assay systems to screen large chemical compound libraries for the purpose of drug discovery. Such assay systems are also useful to characterize chemically modified lead compounds after the initial high-throughput screening.

The RIα specific binding differences for the D-AKAP2 Ile/Val 27-mer peptide variants elucidated herein are contemplated as translating into one or more health risks. AKAPs in general coordinate signaling through PKA by bringing together effector molecules at specific sub-cellular locations (Edwards et al. (2000) *Current Opinion in Cell Biology*, 12:217-221). The Ile(646) variant (SEQ ID NO:64), which is selected for in the healthy population, is contemplated herein to result in a reduction in signaling through the PKA RIα isoform. This signal reduction could have a beneficial effect on the cell. The narrow affinity differences observed for the binding of the variants to RIα suggest that local concentrations of RIα are tightly regulated. While AKAP specific anchoring of PKA through RIIα has been well documented, little was previously known about anchoring PKA through RIα. As provided herein, however, anchoring PKA through the RIα subunit appears to be more dynamic. RIα is found diffuse in the cytoplasm of most cells, however several examples of RIα localization have been reported. RIα is recruited to the plasma membrane upon antigen-mediated lymphocyte activation (Skalhegg et al. (1994) *Science*, 263:84-87), localized to the neuromuscular junction of skeletal muscle (Barradeau et al. (2001) *Proc. Natl. Acad. Sci. USA*, 264:250-265), and associated with microtubules during certain stages of the cell cycle (Imaizumi et al. (2001) *Experimental Cell Research*, 264:250-265). Therefore, dynamic regulation between intracellular compartments seems to be key for RIα mediated signaling and might be different depending on the D-AKAP2 variants present in the cell. Accordingly, methods of modulating D-AKAP2-mediated intracellular compartmentalization of PKA are provided herein.

In addition to altering the dynamic nature of the RIα signaling pathway, the Ile/Val(646) variant of D-AKAP2 is contemplated herein to alter the PKA isoform distribution and change the signaling specificity of PKA. D-AKAP2 can bind both RI and RII isoforms of PKA, potentially recruiting two different responses to cAMP signaling. The affinity of cAMP for RIα is higher than RIIα and requires lower concentrations of cAMP for PKA activation (Dostmann et al. (1990) *J. Biol. Chem.*, 265:10484-10491). Therefore, an RIα anchored PKA isoform would be activated by a lower, transient concentration of cAMP as opposed to a higher, persistent concentration for RIIα (Feliciello et al. (2001) *J. Mol. Biol.*, 308:99-114). The tighter binding D-AKAP2 Val(646) variant could potentially more effectively recruit RIα at the expense of the RIIα isoform, altering the isoform distribution and changing the cAMP mediated signaling response.

Increasing evidence indicates that the RI and RII isoforms of PKA have distinct functions. The RIα isoform is predominant in growing cells while the RIIα isoform is predominant in differentiated cells (Cho et al. (1995) *Critical Reviews in Oncology/Hematology*, 21:33-61). The importance of RIα regulation for the cell is indicated by the fact that RIα knockout mice are embryonically lethal (Amieux et al. (1997) *J. Biol. Chem.*, 272:3993). In RIIα and RIIβ knockout mice, RIα is up-regulated and seems to compensate for loss of these isoforms (Amieux et al. (1997) *J. Biol. Chem.*, 272:3993-3998). However, novel phenotypes result since the mice are lean and have an increased tolerance to alcohol (Cummings et al. (1996) *Nature*, 382:622-626); Thiele et al. (2000) *J. Neuroscience*, 20:RC75:1-6). These observations suggest an implication for dynamic PKA isoform regulation in lipid metabolism, which is contemplated herein as being modulated by D-AKAP2.

Also provided herein are methods of disrupting the binding of an Ile/Val(646) isoform of D-AKAP2 corresponding to SEQ ID NOs:64 and 65 to the RIα subunit of PKA comprising contacting the RIα subunit with a peptide provided herein, such as set forth in Examples 5-9 or in the claims. Also provided is a method for modulating the amount of PKA-RIα bound to D-AKAP2 in a cell comprising changing the effective intracellular concentration of the Val(646) isoform of D-AKAP2 (corresponding to SEQ ID NO:65) in the cell. The change can be where the intracellular concentration of the Val(646) isoform is increased, thereby increasing the amount of PKA-RIα bound to D-AKAP2; or where the intracellular concentration of the Val(646) isoform is decreased, thereby decreasing the amount of PKA-RIα bound to D-AKAP2.

Also provided herein is a method for altering the intracellular location of PKA in a cell comprising changing the effective intracellular concentration of the Val(646) isoform of D-AKAP2 (corresponding to SEQ ID NO:65) in the cell. The change can be where the intracellular concentration of the Val(646) isoform is increased, thereby increasing the amount of PKA localized to the mitochondria; or where the intracellular concentration of the Val(646) isoform is decreased, thereby decreasing the amount of PKA localized to the mitochondria. Also provided is a method of treating a subject manifesting a disease or disorder of signal transduction wherein there is an increased mitochondrial localization of PKA, said method comprising administering a peptide provided herein, such as disclosed in Example 5-9 and in the claims, or peptidomimetic thereof.

Also provided is a method of increasing the longevity of a subject in need thereof, comprising identifying a subject having the Val(646) isoform of D-AKAP2 therein, and treating said subject with an agent that disrupts the binding the Val (646) isoform of D-AKAP2 to RIα subunit of PKA. The agent can be any peptide disclosed herein, such as in Examples 5-9 or any of the claims, or peptidomimetic thereof. Also provided are methods for altering the ratio of PKA-RIα/ PKA-RIIα bound to D-AKAP2 in a cell comprising increasing the concentration of a Val(646) variant of D-AKAP2, corresponding to SEQ ID NO:65, in a cell, thereby increasing the ratio of PKA-RIα PKA/PKA-RIIα bound to D-AKAP2 in a cell. Also provided is a method of decreasing the concentration of cAMP required to stimulate a cAMP mediated signalling pathway, comprising increasing the concentration of a Val(646) variant of D-AKAP2, corresponding to SEQ ID NO:65, in a cell.

Also provided are methods of screening for agents that decrease or disrupt the binding of a Val(646) variant of D-AKAP2 with RIα PKA, comprising combining a candidate agent with a cell comprising a nucleotide sequence which encodes a Val(646) variant D-AKAP protein corresponding to SEQ ID NO:65 or the complement thereof, operably linked to a promoter such that the nucleotide sequence is expressed as a D-AKAP2 protein in the cell; and determining the effect of the agent upon the localization of PKA to the mitochondria, wherein a decrease in localization to the mitochondria identifies an agent that decreases the binding of a Val(646) variant of D-AKAP2 with RIα PKA.

Provided herein are methods of screening for agents that decrease or disrupt the binding of a Val(646) variant of D-AKAP2 to an RIα subunit of PKA, comprising combining a candidate agent with an admixture comprising RIα and a D-AKAP2 peptide sequence that binds to RIα; and determining the effect of the agent upon the binding of the peptide to RIα and/or the localization of PKA to the mitochondria. The candidate agent is combined with the admixture in a cell-free system or intracellularly. The peptide sequence can be obtained from any one of the Examples or claims provided herein.

Also provided are methods for identifying a molecule that modulates the biological activity of a D-AKAP2 protein, comprising combining the candidate molecule with a cell comprising a nucleotide sequence encoding a D-AKAP2 mutein or portion thereof that retains a biological activity exhibited by a full length variant protein, operably linked to a promoter such that the nucleotide sequence is expressed as an D-AKAP2 mutein or portion thereof in the cell; and determining the effect of the molecule upon a biological activity of the D-AKAP2 mutein or portion thereof. The biological activity of the D-AKAP2 mutein or portion thereof can be determined by examining signal transduction in the cell. The biological activity can be the binding of D-AKAP2 protein or portion thereof to protein kinase A. Also, the biological activity of the D-AKAP2 protein or portion thereof can be determined by examining protein phosphorylation in the cell. The screening methods provided herein can be high-throughput.

DETAILED DESCRIPTION

A. Definitions

Figure 1:
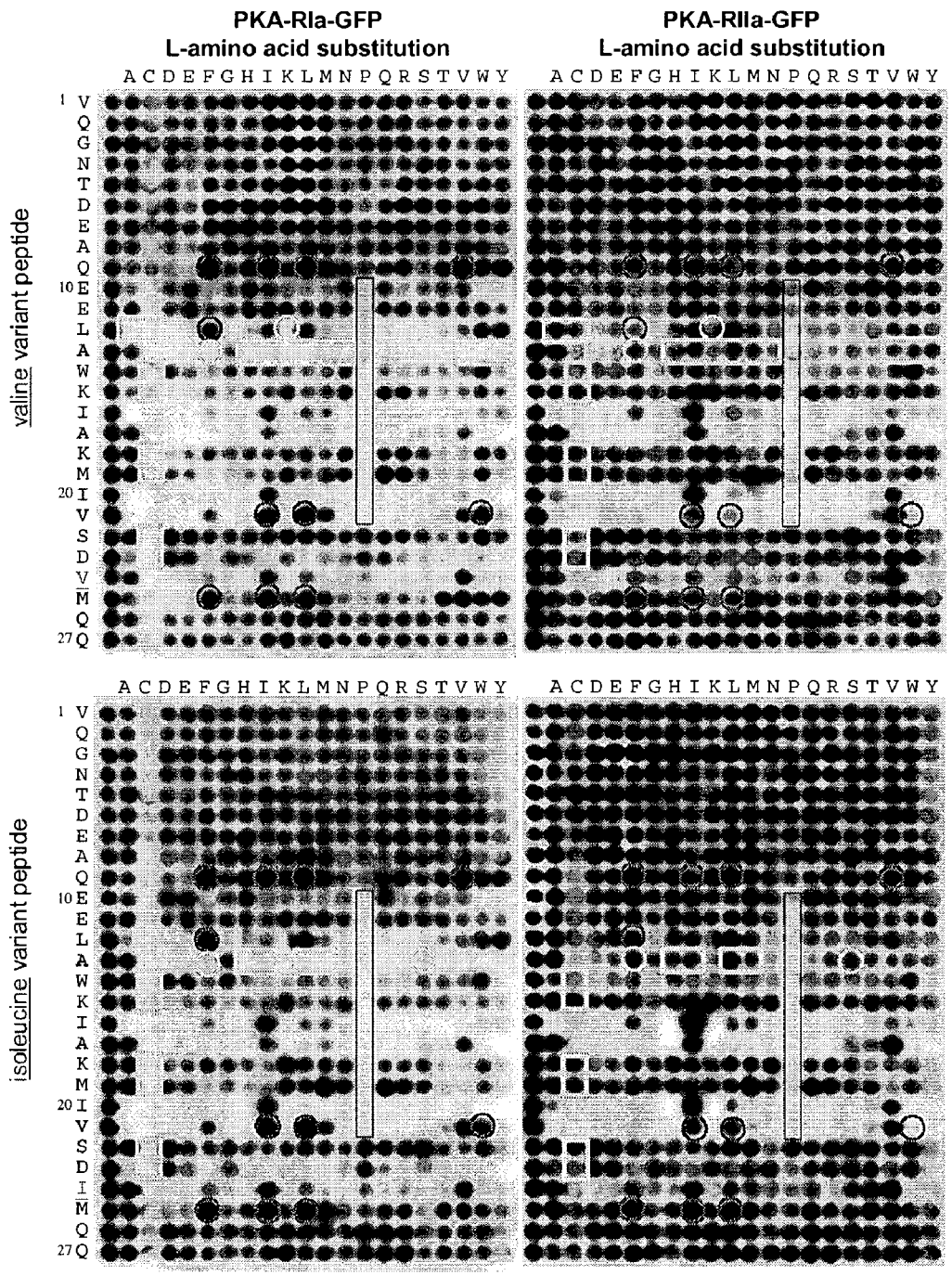
FIG. 1 shows the results of incubating membranes containing the peptide array of the single amino acid substitutions using L-amino acids set forth in Example 7.

Unless defined otherwise, all technical and scientific terms used herein have the same meaning as is commonly understood by one of skill in the art to which the invention(s) belong. All patents, patent applications, published applications and publications, Genbank sequences, websites and other published materials referred to throughout the entire disclosure herein, unless noted otherwise, are incorporated by reference in their entirety. Where reference is made to a URL or other such identifier or address, it understood that such identifiers can change and particular information on the internet can come and go, but equivalent information can be found by searching the internet. Reference thereto evidences the availability and public dissemination of such information.

As used herein, the term "mutein" refers to a peptide variant having one, two or more amino acid residue substitutions compared to a reference polypeptide, which can be a naturally occurring peptide sequence. The phrase "one, two, or more" in the context of amino acid residue substitutions encompasses peptide variants provided herein having one or more amino acid substitutions, e.g., in SEQ ID NOs:1, 2, 55, 63, 64 or 65, including peptides having any combination of 2, 3, 4, 5, 6, 7, 8, 9, 10 or more of the amino acid residue substitutions set forth herein, such as those described above and in Examples 5-9. In addition to these combinations of variants, conservative substitutions can be added at residues that have not yet been modified or at already modified residues within the peptides.

As used herein, the phrase "modified binding" refers to either an increase or decrease in binding affinity to the respective control peptide. Control peptides used herein can be either one or both of the naturally occurring full length Ile/ Val646 isoforms of D-AKAP2. Control peptides used herein can also be either one or both of the Ile/Val 27-mer isoforms set forth in SEQ ID NOs:1 or 2; or full length proteins, such as SEQ ID NOs:55, 64 or 65.

As used herein, the phrase "normal binding" refers to a substantially equivalent binding affinity of a mutein compared to the respective control peptide.

As used herein, the term "segment" refers to a contiguous portion of the reference polypeptide or nucleic acid. For example, a segment of amino acids 12-23 of SEQ ID NO:1 refers to the contiguous stretch of amino acids 12-23 of SEQ ID NO:1. The phrase "at least amino acids 12-23 of SEQ ID NOs:1 or 2 up to amino acids 1-27 of SEQ ID NOs:1 or 2" refers to multiple segments of different sizes ranging from amino acids 12-23 of SEQ ID NOs:1 or 2; amino acids 12-24 of SEQ ID NOs:1 or 2; amino acids 11-23 of SEQ ID NOs:1 or 2; amino acids 10-25 of SEQ ID NOs:1 or 2; up to amino acids 1-27 of SEQ ID NOs:1 or 2.

As used herein, the phrase "a regulatory subunit of PKA" refers to one of the subunits of a PKA holoenzyme. Exemplary PKA subunits include RIα and RIIα subunits.

As used herein, the phrase "peptide exhibits a preferred or exclusive binding to PKA-RIα subunits relative to PKA-RIIα subunits", or grammatical variations thereof, refers to a peptide that either has a higher binding affinity for PKA-RIα subunits than for PKA-RIIα or has the ability to bind to PKA-RIα and substantially no ability to bind PKA-RIIα.

As used herein, the phrase "peptide exhibits enhanced binding to both RIα and RIIα subunits" refers to a peptide that has a higher binding affinity for both PKA-RIα and PKA-RIIα subunits compared to the binding affinity of the peptide of SEQ ID NOs:1 or 2 for both PKA-RIα and PKA-RIIα subunits.

As used herein, the phrase "peptide exhibits a preferred or exclusive binding to PKA-RIIα subunits relative to PKA-RIα subunits", or grammatical variations thereof, refers to a peptide that either has a higher binding affinity for PKA-RIIα subunits than for PKA-RIα or has the ability to bind to PKA-RIIα and substantially no ability to bind PKA-RIα.

As used herein, "polymorphism" refers to the coexistence of more than one form of a gene or portion thereof. A portion of a gene of which there are at least two different forms, i.e., two different nucleotide sequences, is referred to as a "polymorphic region of a gene". A polymorphic region can be a single nucleotide, the identity of which differs in different alleles. A polymorphic region can also be several nucleotides in length.

As used herein, "polymorphic gene" refers to a gene having at least one polymorphic region.

As used herein, "allele", which is used interchangeably herein with "allelic variant", refers to alternative forms of a gene or portions thereof. Alleles occupy the same locus or position on homologous chromosomes. When a subject has two identical alleles of a gene, the subject is said to be homozygous for the gene or allele. When a subject has two different alleles of a gene, the subject is said to be heterozygous for the gene. Alleles of a specific gene can differ from each other in a single nucleotide, or several nucleotides, and can include substitutions, deletions, and insertions of nucleotides. An allele of a gene can also be a form of a gene containing a mutation.

As used herein, "predominant allele" refers to an allele that is represented in the greatest frequency for a given population. The allele or alleles that are present in lesser frequency are referred to as allelic variants.

As used herein, "associated" refers to coincidence with the development or manifestation of a disease, condition or phenotype. Association may be due to, but is not limited to, genes responsible for housekeeping functions whose alteration can provide the foundation for a variety of diseases and conditions, those that are part of a pathway that is involved in a specific disease, condition or phenotype and those that indirectly contribute to the manifestation of a disease, condition or phenotype.

As used herein, the term "subject" refers to mammals and in particular human beings.

As used herein, the term "gene" or "recombinant gene" refers to a nucleic acid molecule comprising an open reading frame and including at least one exon and (optionally) an intron sequence. A gene can be either RNA or DNA. Genes may include regions preceding and following the coding region (leader and trailer).

As used herein, "intron" refers to a DNA sequence present in a given gene which is spliced out during mRNA maturation.

As used herein, the term "coding sequence" refers to that portion of a gene that encodes an amino acid sequence of a protein.

As used herein, the amino acids, which occur in the various amino acid sequences appearing herein, are identified according to their well-known, three-letter or one-letter abbreviations. The nucleotides, which occur in the various DNA fragments, are designated with the standard single-letter designations used routinely in the art (see, Table 1).

As used herein, "amino acid residue" refers to an amino acid formed upon chemical digestion (hydrolysis) of a polypeptide at its peptide linkages. The amino acid residues described herein are preferably in the "L" isomeric form. However, residues in the "D" isomeric form can be substituted for any L-amino acid residue, as long as the desired functional property is retained by the polypeptide. $NH_2$ refers to the free amino group present at the amino terminus of a polypeptide. COOH refers to the free carboxy group present at the carboxyl terminus of a polypeptide. In keeping with standard polypeptide nomenclature described in *J. Biol. Chem.*, 243:3552-3559 (1969) and adopted at 37 C.F.R. §§ 1.821-1.822, abbreviations for amino acid residues are shown in the following Table:

TABLE 1

Table of Correspondence

| SYMBOL | | |
|---|---|---|
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| Z | Glx | Glu and/or Gln |
| W | Trp | tryptophan |
| R | Arg | arginine |
| D | Asp | aspartic acid |
| N | Asn | asparagine |
| B | Asx | Asn and/or Asp |
| C | Cys | cysteine |
| X | Xaa | Unknown or other |

It should be noted that all amino acid residue sequences represented herein by formulae have a left to right orientation in the conventional direction of amino-terminus to carboxyl-terminus. In addition, the phrase "amino acid residue" is broadly defined to include the amino acids listed in the Table of Correspondence and modified and unusual amino acids, such as those referred to in 37 C.F.R. §§ 1.821-1.822, and incorporated herein by reference. Furthermore, it should be noted that a dash at the beginning or end of an amino acid residue sequence indicates a peptide bond to a further sequence of one or more amino acid residues or to an amino-terminal group such as NH$_2$ or to a carboxyl-terminal group such as COOH.

In a peptide or protein, suitable conservative substitutions of amino acids are known to those of skill in this art and may be made generally without altering the biological activity of the resulting molecule. Those of skill in this art recognize that, in general, single amino acid substitutions in non-essential regions of a polypeptide do not substantially alter biological activity (see, e.g., Watson et al. (1987) *Molecular Biology of the Gene,* 4th Edition, The Benjamin/Cummings Pub. Co., p. 224).

Such substitutions are preferably made in accordance with those set forth in TABLE 2 as follows:

TABLE 2

| | |
|---|---|
| Ala (A) | Gly; Ser |
| Arg (R) | Lys |
| Asn (N) | Gln; His |
| Cys (C) | Ser |
| Gln (Q) | Asn |
| Glu (E) | Asp |
| Gly (G) | Ala; Pro |
| His (H) | Asn; Gln |
| Ile (I) | Leu; Val |
| Leu (L) | Ile; Val |
| Lys (K) | Arg; Gln; Glu |
| Met (M) | Leu; Tyr; Ile |
| Phe (F) | Met; Leu; Tyr |
| Ser (S) | Thr |
| Thr (T) | Ser |
| Trp (W) | Tyr |
| Tyr (Y) | Trp; Phe |
| Val (V) | Ile; Leu |

Other substitutions are also permissible and may be determined empirically or in accord with known conservative substitutions.

As used herein, a DNA or nucleic acid homolog refers to a nucleic acid that includes a preselected conserved nucleotide sequence, such as a sequence encoding a therapeutic polypeptide. By the term "substantially homologous" is meant having at least 80%, preferably at least 90%, most preferably at least 95% homology therewith or a less percentage of homology or identity and conserved biological activity or function.

The terms "homology" and "identity" are often used interchangeably. In this regard, percent homology or identity may be determined, for example, by comparing sequence information using a GAP computer program. The GAP program uses the alignment method of Needleman and Wunsch (1970) *J. Mol. Biol.,* 48:443, as revised by Smith and Waterman (1981) *Adv. Appl. Math.,* 2:482. Briefly, the GAP program defines similarity as the number of aligned symbols (i.e., nucleotides or amino acids) which are similar, divided by the total number of symbols in the shorter of the two sequences. The preferred default parameters for the GAP program may include: (1) a unary comparison matrix (containing a value of 1 for identities and 0 for non-identities) and the weighted comparison matrix of Gribskov and Burgess (1986) *Nucl. Acids Res.,* 14:6745, as described by Schwartz and Dayhoff, eds., *ATLAS OF PROTEIN SEQUENCE AND STRUCTURE,* National Biomedical Research Foundation, pp. 353-358 (1979); (2) a penalty of 3.0 for each gap and an additional 0.10 penalty for each symbol in each gap; and (3) no penalty for end gaps.

Whether any two nucleic acid molecules have nucleotide sequences that are at least 80%, 85%, 90%, 95%, 96%, 97%, 98% or 99% "identical" can be determined using known computer algorithms such as the "FAST A" program, using for example, the default parameters as in Pearson and Lipman (1988) *Proc. Natl. Acad. Sci. USA,* 85:2444. Alternatively the BLAST function of the National Center for Biotechnology Information database may be used to determine identity In general, sequences are aligned so that the highest order match is obtained. "Identity" per se has an art-recognized meaning and can be calculated using published techniques. (See, e.g., *Computational Molecular Biology,* Lesk, A. M., ed., Oxford University Press, New York, 1988; *Biocomputing: Informatics and Genome Projects,* Smith, D. W., ed., Academic Press, New York, 1993; *Computer Analysis of Sequence Data,* Part I, Griffin, A. M., and Griffin, H. G., eds., Humana Press, New Jersey, 1994; *Sequence Analysis in Molecular Biology,* von Heinje, G., Academic Press, 1987; and *Sequence Analysis Primer,* Gribskov, M. and Devereux, J., eds., M Stockton Press, New York, 1991). While there exist a number of methods to measure identity between two polynucleotide or polypeptide sequences, the term "identity" is well known to skilled artisans (Carillo, H. & Lipton, D., (1988) *SIAM J. Applied Math.,* 48:1073. Methods commonly employed to determine identity or similarity between two sequences include, but are not limited to, those disclosed in *Guide to Huge Computers,* Martin J. Bishop, ed., Academic Press, San Diego, 1994; and Carillo, H. & Lipton, D., (1988) *SIAM J. Applied Math.,* 48:1073. Methods to determine identity and similarity are codified in computer programs. Preferred computer program methods to determine identity and similarity between two sequences include, but are not limited to, GCG program package (Devereux, J. et al. (1984) *Nucleic Acids Research,* 12(I):387), BLASTP, BLASTN, FASTA (Atschul, S. F. et al. (1990) *J. Mol. Biol.,* 215:403).

Therefore, as used herein, the term "identity" represents a comparison between a test and a reference polypeptide or polynucleotide. For example, a test polypeptide may be defined as any polypeptide that is 90% or more identical to a reference polypeptide.

As used herein, the term at least "90% identical to" refers to percent identities from 90 to 99.99 relative to the reference polypeptides. Identity at a level of 90% or more is indicative of the fact that, assuming for exemplification purposes a test and reference polypeptide length of 100 amino acids are compared, no more than 10% (i.e., 10 out of 100) amino acids in the test polypeptide differs from that of the reference polypeptides. Similar comparisons may be made between a test and reference polynucleotides. Such differences may be represented as point mutations randomly distributed over the entire length of an amino acid sequence or they may be clustered in one or more locations of varying length up to the maximum allowable, e.g., 10/100 amino acid difference (approximately 90% identity). Differences are defined as nucleic acid or amino acid substitutions, or deletions.

As used herein, stringency conditions refer to the washing conditions for removing the non-specific probes and conditions that are equivalent to either high, medium, or low stringency as described below:

| | |
|---|---|
| 1) high stringency: | 0.1 × SSPE, 0.1% SDS, 65° C. |
| 2) medium stringency: | 0.2 × SSPE, 0.1% SDS, 50° C. |
| 3) low stringency: | 1.0 × SSPE, 0.1% SDS, 50° C. |

It is understood that equivalent stringencies may be achieved using alternative buffers, salts and temperatures.

As used herein, "heterologous DNA" is DNA that encodes RNA and proteins that are not normally produced in vivo by the cell in which it is expressed or that mediates or encodes mediators that alter expression of endogenous DNA by affecting transcription, translation, or other regulatable biochemical processes or is not present in the exact orientation or position as the homologous DNA in a wildtype cell. Heterologous DNA may also be referred to as foreign DNA. Any DNA that one of skill in the art would recognize or consider as heterologous or foreign to the cell in which is expressed is herein encompassed by heterologous DNA. Examples of heterologous DNA include, but are not limited to, DNA that encodes traceable marker proteins, such as a protein that confers drug resistance, DNA that encodes therapeutically effective substances, such as anti-cancer agents, enzymes and hormones, and DNA that encodes other types of proteins, such as antibodies. Antibodies that are encoded by heterologous DNA may be secreted or expressed on the surface of the cell in which the heterologous DNA has been introduced.

As used herein, "isolated" in reference to a nucleic acid molecule or polypeptide or other biomolecule means that the nucleic acid or polypeptide has been separated from the genetic environment from which the polypeptide or nucleic acid was obtained. It may also mean altered from the natural state. For example, a polynucleotide or a polypeptide naturally present in a living animal is not "isolated," but the same polynucleotide or polypeptide separated from the coexisting materials of its natural state is "isolated", as the term is employed herein. Thus, a polypeptide or polynucleotide produced and/or contained within a recombinant host cell is considered isolated. Also intended as an "isolated polypeptide" or an "isolated polynucleotide" are polypeptides or polynucleotides that have been purified, partially or substantially, from a recombinant host cell or from a native source. For example, a recombinantly produced version of a compound can be substantially purified by the one-step method described in Smith and Johnson (1988) Gene, 67:31-40. The terms isolated and purified are sometimes used interchangeably.

Thus, by "isolated" is meant that the nucleic acid is free of the coding sequences of those genes that, in the naturally-occurring genome of the organism (if any) immediately flank the gene encoding the nucleic acid of interest. Isolated DNA may be single-stranded or double-stranded, and may be genomic DNA, cDNA, recombinant hybrid DNA, or synthetic DNA. It may be identical to a native DNA sequence, or may differ from such sequence by the deletion, addition, or substitution of one or more nucleotides.

Isolated or purified, as it refers to preparations made from biological cells or hosts, means any cell extract containing the indicated DNA or protein, including a crude extract of the DNA or protein of interest. For example, in the case of a protein, a purified preparation can be obtained following an individual technique or a series of preparative or biochemical techniques and the protein of interest can be present at various degrees of purity in these preparations. The procedures may include for example, but are not limited to, ammonium sulfate fractionation, gel filtration, ion exchange change chromatography, affinity chromatography, density gradient centrifugation and electrophoresis.

As used herein, "production by recombinant means by using recombinant DNA methods" refers to the use of the well known methods of molecular biology for expressing proteins encoded by cloned DNA, and may include methods such as gene shuffling and phage display with screening for desired specificities.

As used herein, a composition refers to any mixture of two or more products or compounds. It may be a solution, a suspension, liquid, powder, a paste, aqueous, non-aqueous or any combination thereof.

As used herein, a combination refers to any association between two or more items.

As used herein, "substantially identical to a product" means sufficiently similar so that the property of interest is sufficiently unchanged so that the substantially identical product can be used in place of the product.

As used herein, the term "vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/or expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer generally to circular double stranded DNA loops which, in their vector form are not bound to the chromosome. "Plasmid" and "vector" are used interchangeably as the plasmid is the most commonly used form of vector. Other such forms of expression vectors that serve equivalent functions and that become known in the art subsequently may be used.

As used herein, "predisposition to develop a disease or disorder" means that a subject having a particular genotype and/or haplotype has a higher likelihood than one not having such a genotype and/or haplotype for developing a particular disease or disorder.

As used herein, "morbidity" refers to conditions, such as diseases or disorders, that compromise the health and well-being of an organism, such as an animal. Morbidity susceptibility or morbidity-associated genes are genes that, when altered, for example, by a variation in nucleotide sequence, facilitate the expression of a specific disease clinical phenotype. Thus, morbidity susceptibility genes have the potential, upon alteration, of increasing the likelihood or general risk that an organism will develop a specific disease, which may decrease the longevity of the organism.

As used herein, "mortality" refers to the statistical likelihood that an organism, particularly an animal, will not survive a full predicted lifespan. Hence, a trait or a marker, such as a polymorphism, associated with increased mortality is observed at a lower frequency in older than younger segments of a population.

As used herein, the phrase "increasing the longevity of a subject in need thereof" refers to prolonging the life and/or health of a subject or organism. The methods provided herein are contemplated to increase the longevity or improve the health of a subject or organism by the administration of agents that disrupt the binding the Val(646) isoform of D-AKAP2 to RIα subunit of PKA. For example, protein phosphorylation is an important mechanism for enzyme regulation and signal transduction in eukaryotic cells, and therefore is an important mechanism to the longevity of cells and organisms as a whole. cAMP dependent protein kinase (PKA) mediates a variety of hormonal and neurotransmitter responses by phosphorylating a wide variety of substrates including enzymes, membrane receptors, ion channels and transcription factors. AKAPs direct the subcellular localization of cAMP-dependent protein kinase by binding to its regulatory subunits and therefore play a role in G-protein mediated receptor-signalling pathways (see, e.g., Huang et al. (1997) *Proc. Natl. Acad. Sci., USA* 94:11184). As set forth herein, AKAPs, such as D-AKAP2, have PKA binding regions therein.

In addition, the main way to rapidly regulate contractility in the mammalian heart is through the β-adrenergic receptor (β-AR) pathway. This mechanism is important as a means of responding to neurotransmitter (norepinephrine) or hormone (epinephrine) release. β-ARs belong to the large family of G protein-coupled receptors characterized by a typical structure with seven transmembrane domains. These receptors contain phosphorylation sites, which serve as targets for protein kinase A (PKA), protein kinase C, and β-adrenergic receptor kinases to desensitize the receptor in order to prevent an excessive β-adrenergic stimulation. The combination of the β-receptor, the G-protein complex, and adenylyl cyclase is termed the β-adrenergic system that enhances activity of adenylate cyclase increasing cAMP levels. cAMP then activates PKA which initiates a cascade of events eventually leading to an increase in heart rate and contractility. Therefore, PKA, and thus D-AKAP2, are involved in both the signal transduction after β-adrenergic stimulation and the receptor desensitization through its phosphorylation.

The D-AKAP2 variants at amino acid 646 of SEQ ID NOs:64 and 65 described herein map to the conserved AKB domain of D-AKAP2, which was previously shown to interact with the regulatory subunit of PKA. In accordance with the methods provided herein, it has been demonstrated that this variation in D-AKAP2 impacts the binding to PKA in an isoform specific manner both in vitro and in vivo. The Val (646) variant at amino acid 646 of SEQ ID NO:65, which has previously been identified as a deleterious allele associated with morbidity in the age-stratified approach (see, e.g., U.S. patent application US20020040130A1 and PCT WO 02/04489), binds three-fold tighter to the RIα isoform when compared to the Ile(646) variant. At the cellular level, this affinity difference resulted in a decrease in mitochondrial localization of the Ile (646) variant. Accordingly, agents that disrupt the binding the Val(646) isoform of D-AKAP2 to RIα subunit of PKA are contemplated herein as having the ability to increase the longevity of a particular subject or organism.

As used herein, "transgenic animal" refers to any animal, preferably a non-human animal, e.g., a mammal, bird or an amphibian, in which one or more of the cells of the animal contain heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical crossbreeding, or in vitro fertilization, but rather is directed to the introduction of a recombinant DNA molecule. This molecule may be integrated within a chromosome, or it may be extrachromosomally replicating DNA. In the typical transgenic animals described herein, the transgene causes cells to express a recombinant form of a protein. However, transgenic animals in which the recombinant gene is silent are also contemplated, as for example, using the FLP or CRE recombinase dependent constructs. Moreover, "transgenic animal" also includes those recombinant animals in which gene disruption of one or more genes is caused by human intervention, including recombination and antisense techniques.

As used herein, "signal moiety" refers to any moiety that allows for the detection of a nucleic acid molecule. Included are moieties covalently attached to nucleic acids and those that are not.

As used herein, "molecule that modulates or effects the biological activity of an D-AKAP2 protein" refers to any drug, small molecule, nucleic acid (sense and antisense), ribozyme, protein, peptide, lipid, carbohydrate etc., or combination thereof, that directly or indirectly changes, alters, abolishes, increases or decreases a biological activity attributed to D-AKAP2 protein.

As used herein, "biological activity of an D-AKAP2 protein" refers to, but is not limited to: binding of D-AKAP2 to protein kinase A or its subunits (such as RI-α and/or RII-α); localization of D-AKAP2 protein to a subcellular site, e.g., the mitochondria; localization of protein kinase A to the mitochondria and/or binding of D-AKAP2 protein to other proteins including other signalling enzymes.

As used herein, "combining" refers to contacting the biologically active agent with a cell or animal such that the agent is introduced into the cell or animal. For a cell, any method that results in an agent traversing the plasma membrane is useful. For an animal, any of the standard routes of administration of an agent, e.g., oral, rectal, transmucosal, intestinal, intravenous, intraperitoneal, intraventricular, subcutaneous, intramuscular, etc., can be used.

As used herein, "solid support" refers to a support substrate or matrix, such as silica, polymeric materials or glass. At least one surface of the support can be partially planar. Regions of the support may be physically separated, for example with trenches, grooves, wells or the like. Some examples of solid supports include slides and beads. Supports are of such composition so as to allow for the immobilization or attachment of nucleic acids and other molecules such that these molecules retain their binding activity and/or biological activity.

As used herein, "array" refers to a collection of elements, such as nucleic acids, containing three or more members. An addressable array is one in which the members of the array are identifiable, typically by position on a solid support. Hence, in general, the members of the array will be immobilized to discrete identifiable loci on the surface of a solid phase.

As used herein, "specifically hybridizes" refers to hybridization of a probe or primer preferentially to a target sequence versus a non-target sequence. Those of skill in the art are familiar with parameters that affect hybridization; such as temperature, probe or primer length and composition, buffer composition and salt concentration and can readily adjust these parameters to achieve specific hybridization of a nucleic acid to a target sequence.

As used herein "nucleic acid" refers to polynucleotides such as deoxyribonucleic acid (DNA) and ribonucleic acid (RNA). The term should also be understood to include, as equivalents, derivatives, variants and analogs of either RNA or DNA made from nucleotide analogs, single-stranded (sense or antisense) and double-stranded polynucleotides. Deoxyribonucleotides include deoxyadenosine, deoxycytidine, deoxyguanosine and deoxythymidine. For RNA, the uracil base is uridine.

As used herein, "at a position corresponding to" refers to a position of interest (i.e., base number or residue number) in a nucleic acid molecule or protein relative to the position in another reference nucleic acid molecule or protein. Corresponding positions can be determined by comparing and aligning sequences to maximize the number of matching nucleotides or residues, for example, such that identity between the sequences is greater than 95%, preferably greater than 96%, more preferably greater than 97%, even more preferably greater than 98% and most preferably greater than 99%. The position of interest is then given the number assigned in the reference nucleic acid molecule. For example, it is shown herein that a particular polymorphism in D-AKAP2 occurs at nucleotide 2073 of SEQ ID NO:63. To identify the corresponding nucleotide in another allele or isolate, the sequences are aligned and then the position that lines up with 2073 is identified. Since various alleles may be of different length, the position designate 2073 may not be nucleotide 2073, but instead is at a position that "corresponds" to the position in the reference sequence.

As used herein, "primer" and "probe" refer to a nucleic acid molecule including DNA, RNA and analogs thereof, including protein nucleic acids (PNA), and mixtures thereof. Such molecules are typically of a length such that they are statistically unique (i.e., occur only once) in the genome of interest. Generally, for a probe or primer to be unique in the human genome, it contains at least 14, 16 or contiguous nucleotides of a sequence complementary to or identical to a gene of interest. Probes and primers can be 10, 20, 30, 50, 100 or more nucleic acids long.

As used herein, "antisense nucleic acid molecule" refers to a molecule encoding a sequence complementary to at least a portion of an RNA molecule. The sequence is sufficiently complementary to be able to hybridize with the RNA, preferably under moderate or high stringency conditions to form a stable duplex. The ability to hybridize depends on the degree of complementarity and the length of the antisense nucleic acid. Generally, the longer the hybridizing nucleic acid, the more base mismatches with an RNA it can contain and still form a stable duplex. One skilled in the art can ascertain a tolerable degree of mismatch by use of standard procedures to determine the melting point of the hybridized complex.

As used herein, a "variant protein" or "variant peptide" refers to a protein or peptide encoded by a mutein variant of a D-AKAP2 gene which results in a change of an amino acid residue at a particular position relative to that position in the protein encoded by the predominant allele. Accordingly, a mutein protein or peptide refers to a polypeptide sequence that differs or varies from a respective naturally occurring sequence by one, two or more amino acid residues. For example, in the peptides provided herein, combinations of 2, 3, 4, 5, 6, 7, 8, 9, 10 or more residue substitutions compared to a particular reference sequence, such as SEQ ID NOs:1 or 2, are contemplated herein in a single peptide. In a particular embodiment, the residue substitutions can be any combination of one or more of the single amino acid substitutions set forth herein, such as in Examples 5-9. In addition, other amino acid residue substitutions can be added to those disclosed herein, both conservative and non-conservative.

As used herein, "signal transduction" refers to the propagation of a signal. In general, an extracellular signal is transmitted through the cell membrane to become an intracellular signal. This signal can then stimulate a cellular response. The term also encompasses signals that are propagated entirely within a cell. The polypeptide molecules involved in signal transduction processes are typically receptor and non-receptor protein kinases, receptor and non-receptor protein phosphatases, nucleotide exchange factors, transcription factors, G-coupled protein receptors, G-proteins, and GTPase regulators. One of the key biochemical mechanisms involved in signal transduction is protein phosphorylation. D-AKAP2 proteins are involved in signal transduction as they bind to protein kinase A (PKA) and are thought to anchor the kinase at a location, e.g., the mitochondria, where PKA acts to phosphorylate a specific substrate, either at the mitochondria or at an ion channel. Thus, an alteration in D-AKAP2 binding to PKA, localization to the mitochondria, or phosphorylation by PKA, among other steps, will result in an alteration in signal transduction. Assays including those that determine phosphorylation by PKA, association of PKA and D-AKAP2 and localization of D-AKAP2 can be used to monitor the state of signal transduction.

As used herein, "binding to PKA", refers to the interaction of the PKA binding domain (also referred to herein as the A-Kinase binding (AKB) domain) of an D-AKAP2 protein and the regulatory subunits RI and/or RII of the protein kinase A holoenzyme. For example, the AKB domain of human D-AKAP2 corresponds to amino acids 623-649 of SEQ ID NOs:63-65.

B. Polymorphic AKAPs

Polymorphisms of the genome can lead to altered gene function, protein function or mRNA instability. AKAPs provide a mechanism for regulating ubiquitous cAMP-dependent kinase (PKA) activity by tethering PKA to specific subcellular locations thereby segregating it with particular components in a given signaling pathway and contributing to specificity in cellular responses to extracellular signals. AKAPs thus play a fundamental role in the basic functioning of cells, the response of cells to their environment and ultimately in the coordination of vital systems within an organism. Therefore, polymorphisms in AKAP gene sequences may significantly affect the proper functioning of cells and systems within organisms and could be directly linked with certain disorders or could predispose an organism to a variety of diseases and disorders, especially those involving alterations in cellular protein phosphorylation and/or signal transduction. Among such disorders and diseases are:

neurodegenerative diseases, such as Alzheimer's Disease, cardiovascular disorders, cardiac disorders, particularly disorders associated with altered left ventricular function, cardiomyopathies, proliferative disorders, bipolar disorder and other neurological disorders, obesity, neoplastic disease, diabetes, certain peripheral retinopathies, such as retinitis pigmentosa, and autoimmune disorders, such as Lupus erythematosus. The discovery of AKAP gene polymorphisms, such as those described herein, provides for the identification and development of diagnostic and prognostic methods, also provided herein, and the development of drug therapies and treatment regimens. Furthermore, polymorphisms of AKAP genes aid in the study of AKAP protein structure and function, which also contributes to the development of diagnostic methods and therapies.

1. D-AKAP2

Although the mechanisms for targeting of D-AKAP2 are not known, the D-AKAP2 protein can be found associated with mitochondria. The sequence of a human D-AKAP2 cDNA (also referred to as D-AKAP2) is available in the GenBank database, at accession numbers AF037439 and NM 007202, and is provided in SEQ ID NO:63. The D-AKAP2 gene is located on chromosome 17.

The sequence of a mouse D-AKAP2 cDNA is also available in the GenBank database (see accession number AF021833). The mouse D-AKAP2 protein contains two RGS domains near the amino terminus that is characteristic of proteins that interact with Ga subunits and possess GTPase activating protein-like activity (Huang et al. (1997) *PNAS, USA*, 94:11184-11189; and Wang et al. (2001) *PNAS, USA*, 98(6):3220-3225). The human D-AKAP2 protein also has sequences homologous to two RGS domains. The carboxy-terminal 40 residues of the mouse D-AKAP2 protein are responsible for the interaction with the regulatory subunits of PKA. This sequence is fairly well conserved between the mouse D-AKAP2 and human D-AKAP2 proteins.

2. Polymorphisms of the Human D-AKAP2 Gene and Polymorphic D-AKAP2 Proteins

Polymorphisms of AKAP genes that alter gene expression, regulation, protein structure and/or protein function are more likely to have a significant effect on the regulation of enzyme (particularly PKA) activity, cellular transduction of signals and responses thereto and on the basic functioning of cells than polymorphisms that do not alter gene and/or protein function. Included in the polymorphic AKAPs provided herein are human D-AKAP2 proteins containing differing amino acid residues at position number 646 of SEQ ID NO:64.

Amino acid 646 of the human D-AKAP2 protein (SEQ ID NO:64) is located in the carboxy-terminal region of the protein within a segment that participates in the binding of R-subunits of PKAs. This segment includes the carboxy-terminal 40 amino acids.

The amino acid residue reported for position 646 of the human D-AKAP2 protein is an isoleucine. However, an allelic variant of the human D-AKAP2 gene is at the polymorphic site at position 2073 of the coding sequence (see SEQ ID NO:63) and encodes a valine at position 646 of the D-AKAP2 protein. This allelic variant has been found to vary in frequency in DNA samples from younger and older segments of a healthy population. This allele has the A at position 2073 of the D-AKAP2 gene coding sequence of SEQ ID NO:63 changed to a G. Consequently, the codon for amino acid 646 changes from ATT, coding for isoleucine, to GTT, coding for valine, as set forth in SEQ ID NO:65.

C. Peptides, Polypeptides and Peptide Mimetics

Provided herein are D-AKAP2 mutein proteins, mutein peptides thereof, and methods for identifying molecules (agents) that bind to and modulate the activity of PKA proteins. Included among muteins that bind to PKAs, particularly the regulatory subunits RIα and RIIα, are peptides derived from the AKB binding domain of the Ile/Val(646) variants of human D-AKAP2 corresponding to amino acids 623-649 of SEQ ID NOs:64 and 65; polypeptides and peptide mimetics thereof, including cyclic peptides. In one embodiment, exemplary D-AKAP2-derived peptides provided herein comprise between 12 and 39 amino acid residues, wherein the peptide comprises amino acids 7-21 of SEQ ID NOs:1 or 2. In another embodiment, exemplary peptides comprise between 12 and 39 amino acid residues, wherein the peptide comprises a segment of SEQ ID NOs:1 or 2, wherein the length of the segment ranges from at least amino acids 12-23 of SEQ ID NOs:1 or 2, up to amino acids 1-27 of SEQ ID NOs:1 or 2. Accordingly, peptides having a length of 13, 14, 15, 16, 17, 18, 19, 20, 21, 22, 23, 24, 25, 26, 27, 28, 29, 30, 31, 32, 33, 34, 35, 36, 37, 38, or 39 amino acids are provided herein. In another embodiment, exemplary D-AKAP2-derived peptides provided herein comprise between 15 and 39 amino acid residues, wherein the peptide comprises amino acids 7-21 of SEQ ID NOs:1 or 2. In one embodiment, the peptide binds to a regulatory subunit of PKA. In one embodiment the peptide binds to RIIα. In another embodiment, the peptide comprises at least amino acids 11-24 of SEQ ID NOs:1 or 2 and binds to RIα. In a particular embodiment, the peptides provided herein bind to both RIα and RIIα subunits.

In one embodiment, the peptide exhibits a preferred or exclusive binding to PKA-RIα subunits relative to PKA-RIIα subunits; or enhanced binding to both RIα and RIIα subunits. In this particular embodiment, the peptide can be selected from the group consisting of peptides that correspond to the substitution in SEQ ID NOs:1 or 2 of one, two or more: of Q at residue 9 with F, I, L, V, H, M, R, T, W or Y; of L at residue 12 with F, W or Y; of V at residue 21 with I, L or W; and of M at residue 25 with F, I, L, T, V, W or Y. In a particular embodiment, the peptide is 27 amino acids in length. In another embodiment, V at residue 21 is substituted with W. In yet another embodiment, V at residue 21 is substituted with W, and the peptide further comprises the substitution of either one or both of Q at residue 9 with F, and of M at residue 25 with F.

In another embodiment, the peptide exhibits a preferred or exclusive binding to PKA-RIIα subunits relative to PKA-RIα subunits. In this particular embodiment, the peptide can be selected from the group consisting of peptides that correspond to the substitution in SEQ ID NO:2 of one, two or more: of L at residue 12 with A, C, or K; of A at residue 13 with F, H, I, K, L, M or N; of W at residue 14 with C; of K at residue 15 with C; of K at residue 18 with C; of M at residue 19 with C; of S at residue 22 with C; and of D at residue 23 with C. In a particular embodiment, the peptide is 27 amino acids in length.

In yet another embodiment, the peptide is 27 amino acids in length and exhibits preferred or exclusive binding to PKA-RIIα subunits relative to PKA-RIα subunits. In this particular embodiment, the peptide can be selected from the group consisting of peptides that correspond to the substitution in SEQ ID NO:1 of one, two or more: of A at residue 13 with F, H, I, L, M and S; of W at residue 14 with C; of K at residue 15 with C; of K at residue 18 with C; of M at residue 19 with C; of S at residue 22 with C; and of D at residue 23 with C.

In another embodiment, the D-AKAP2-derived peptides have substantially no ability to bind to PKA-RIα subunit while maintaining the ability to bind to PKA-RIIα subunit, compared to the PKA R-subunit binding ability of the peptide of SEQ ID NOs:1 or 2. In this particular embodiment the peptide can be selected from the group consisting of:

| | |
|---|---|
| VQGNTDEAQEELFWKIAKMIVSD[I/V]MQQ; | (SEQ ID NO:27) |
| VQGNTDEAQEELIWKIAKMIVSD[I/V]MQQ; | (SEQ ID NO:28) |
| VQGNTDEAQEELLWKIAKMIVSD[I/V]MQQ; | (SEQ ID NO:29) |
| VQGNTDEAQEELAWCIAKMIVSD[I/V]MQQ; | (SEQ ID NO:30) |
| VQGNTDEAQEELAWKIACMIVSD[I/V]MQQ; | (SEQ ID NO:31) |
| VQGNTDEAQEELAWKIAKCIVSD[I/V]MQQ; and | (SEQ ID NO:32) |
| VQGNTDEAQEELAWKIAKMIVCD[I/V]MQQ. | (SEQ ID NO:33) |

In another embodiment, the D-AKAP2-derived peptides have substantially no ability to bind to a PKA-RIα subunit while maintaining a reduced ability to bind to a PKA-RIIα subunit, compared to the PKA R-subunit binding ability of the peptide of SEQ ID NOs:1 or 2. In this particular embodiment, the peptide can be selected from the group consisting of:

| | |
|---|---|
| VQGNTDEAQEECAWKIAKMIVSD[I/V]MQQ; | (SEQ ID NO:34) |
| VQGNTDEAQEEKAWKIAKMIVSD[I/V]MQQ; | (SEQ ID NO:35) |
| VQGNTDEAQEELHWKIAKMIVSD[I/V]MQQ; | (SEQ ID NO:36) |
| VQGNTDEAQEELKWKIAKMIVSD[I/V]MQQ; | (SEQ ID NO:37) |
| VQGNTDEAQEELMWKIAKMIVSD[I/V]MQQ; | (SEQ ID NO:38) |
| VQGNTDEAQEELNWKIAKMIVSD[I/V]MQQ; | (SEQ ID NO:39) |
| VQGNTDEAQEELVWKIAKMIVSD[I/V]MQQ; | (SEQ ID NO:40) |
| VQGNTDEAQEELWWKIAKMIVSD[I/V]MQQ; | (SEQ ID NO:41) |
| VQGNTDEAQEELYWKIAKMIVSD[I/V]MQQ; | (SEQ ID NO:42) |
| VQGNTDEAQEELAWKIAKMIVSC[I/V]MQQ; | (SEQ ID NO:43) |
| TDEAQEELAWKIAKMIVSD; | (SEQ ID NO:8) |
| DEAQEELAWKIAKMIVS; and | (SEQ ID NO:9) |
| EAQEELAWKIAKMIV. | (SEQ ID NO:4) |

In still a further embodiment, the D-AKAP2-derived peptide has enhanced binding to both PKA-RIα subunit and PKA RIIα subunit, compared to PKA R-subunit binding ability of the peptide of SEQ ID NOs:1 or 2. In this particular embodiment, the peptide can be selected from the group consisting of:

| | |
|---|---|
| VQGNTDEAFEELAWKIAKMIVSD[I/V]MQQ; | (SEQ ID NO:44) |
| VQGNTDEAIEELAWKIAKMVSD[I/V]MQQ; | (SEQ ID NO:45) |
| VQGNTDEALEELAWKIAKMIVSD[I/V]MQQ; | (SEQ ID NO:46) |
| VQGNTDEAVEELAWKIAKMIVSD[I/V]MQQ; | (SEQ ID NO:47) |
| VQGNTDEAQEELAWKIAKMIVSD[I/V]FQQ; | (SEQ ID NO:48) |
| VQGNTDEAQEELAWKIAKMIVSD[I/V]IQQ; and | (SEQ ID NO:49) |
| VQGNTDEAQEELAWKIAKMIVSD[I/V]LQQ. | (SEQ ID NO:50) |

In yet another embodiment, the peptide that has enhanced ability to bind to PKA-RIα subunit, while maintaining a normal or reduced ability to bind to PKA-RIIα subunit, compared to the PKA R-subunit binding ability of the peptide of SEQ ID NOs:1 or 2. In this particular embodiment, the peptide can be selected from the group consisting of:

| | |
|---|---|
| VQGNTDEAQEEFAWKIAKMIVSD[I/V]MQQ; | (SEQ ID NO:51) |
| VQGNTDEAQEELAWKIAKMIISD[I/V]MQQ; and | (SEQ ID NO:52) |
| VQGNTDEAQEELAWKIAKMILSD[I/V]MQQ. | (SEQ ID NO:53) |

In yet a further embodiment, the D-AKAP peptide has an ability to bind to PKA-RIα subunit but substantially no ability to bind to PKA-RIIα subunit, compared to the PKA R-subunit binding ability of the peptide of SEQ ID NOs:1 or 2. In this particular embodiment, the peptide can comprise VQGNTDEAQEELAWKIAKMIWSD[I/V]MQQ (SEQ ID NO:54).

In yet a further embodiment, the D-AKAP peptide has a D-amino acid at the position indicated in bold, and an enhanced ability to bind to PKA-RIα subunit, and a reduced ability to bind to PKA-RIIα subunit, compared to the PKA R-subunit binding ability of the peptide of SEQ ID NOs:1 or 2. In this particular embodiment, the peptide can be selected from the group consisting of:

| | |
|---|---|
| VQGNTTEAQEELAWKIAKMIVSD[I/V]MQQ; | (SEQ ID NO:17) |
| VQGNTDEAFEELAWKIAKMIVSD[I/V]MQQ; | (SEQ ID NO:18) |
| VQGNTDEAIEELAWKIAKMIVSD[I/V]MQQ; | (SEQ ID NO:19) |
| VQGNTDEALEELAWKIAKMIVSD[I/V]MQQ; | (SEQ ID NO:20) |
| VQGNTDEAVEELAWKIAKMIVSD[I/V]MQQ; | (SEQ ID NO:21) |
| VQGNTDEAWEELAWKIAKMIVSD[I/V]MQQ; | (SEQ ID NO:22) |
| VQGNTDEAYEELAWKIAKMIVSD[I/V]MQQ; | (SEQ ID NO:23) |
| VQGNTDEAQEELAWKIAKMILSD[I/V]MQQ; | (SEQ ID NO:24) |
| VQGNTDEAQEELAWKIAKMIVLD[I/V]MQQ; and | (SEQ ID NO:25) |
| VQGNTDEAQEELAWKIAKMIVSD[I/V]FQQ. | (SEQ ID NO:26) |

In another embodiment, the D-AKAP peptide has enhanced ability to bind to PKA-RIα subunit, and a reduced ability to bind to PKA-RIIα subunit, compared to the peptide of SEQ ID NOs:1 or 2, wherein the peptide is selected from the group consisting of:

| | |
|---|---|
| FEELAWKIAKMIWSDVMQQC; | (SEQ ID NO:104; PV-37) |
| FEELAWKIAKMIWSDVFQQC; | (SEQ ID NO:103; PV-38) |
| QEEFAWKIAKMIVSDVFQQC; | (SEQ ID NO:105; PV-47) |
| QEEFAWKIAKMIISDVFQQC;. | (SEQ ID NO:106; PV-48) |

In another embodiment, the peptide has enhanced ability to bind to PKA-RIα subunit, while maintaining a normal ability to bind to PKA-RIIα subunit, compared to the peptide of SEQ ID NO:1 or 2, wherein the peptide is:

| | |
|---|---|
| FEELAWKIAKMIISDVFQQC. | (SEQ ID NO:107; PV-49) |

In another embodiment, peptide variants provided herein having one or more amino acid substitutions in SEQ ID NOs:1 or 2, include peptides having any combination of 2, 3, 4, 5, 6, 7, 8, 9, 10 or more of the amino acid residue substitutions set forth herein, such as those described above and in Examples 5-9. In addition to these combinations of variants, conservative substitutions can be added at residues that have not yet been modified or at already modified residues within the peptides.

Also provided herein, based on the particular effect that a specific amino acid residue substitution has on the binding of a substituted peptide variant to either one or both of RIα or RIIα, one or more amino acid residue substitutions can be selected to either selectively increase or decrease (i.e., disrupt) the binding affinity, and thereby increase the selectivity of a particular peptide for either RIα or RIIα. The residues can be selected based on the effect of the residue substitutions provided herein as set forth in Examples 5-9 and FIG. 1. Accordingly, 2, 3, 4, 5, 6, 7, 8, 9, 10 or more residues that enhance binding of a peptide to either one or both of RI or RII subunits can be combined. Accordingly, 2, 3, 4, 5, 6, 7, 8, 9, 10 or more residues that decrease binding of a peptide to either one or both of RI or RII subunits can be combined. In certain embodiments, 2, 3, 4, 5, 6, 7, 8, 9, 10 or more residues that either increase or decrease binding of a peptide to either one or both of RI or RII subunits can be combined (e.g., residues substituted to increase binding to one R subunit and residues substituted to decrease binding to the other R subunit), and the like.

Accordingly, combinations of two or more amino acid substitutions that increase binding affinity for RIα and/or decrease binding affinity for RIIα are contemplated herein. In another embodiment, combinations of two or more amino acid substitutions that decrease binding affinity for RIα and/or increase binding affinity for RIIα are contemplated herein.

For example, in one embodiment, peptides are provided having in a region corresponding to SEQ ID NOs:1 or 2, a combination of any 2 amino acid residue substitutions set forth herein. In another embodiment, peptides are provided having in a region corresponding to SEQ ID NOs:1 or 2, a combination of any 3 amino acid residue substitutions set forth herein. In another embodiment, peptides are provided having in a region corresponding to SEQ ID NOs:1 or 2, a combination of any 4 amino acid residue substitutions set forth herein. In another embodiment, peptides are provided having in a region corresponding to SEQ ID NOs:1 or 2, a combination of any 5 amino acid residue substitutions set forth herein. In another embodiment, peptides are provided having in a region corresponding to SEQ ID NOs:1 or 2, a combination of any 6 amino acid residue substitutions set forth herein. In another embodiment, peptides are provided having in a region corresponding to SEQ ID NOs:1 or 2, a combination of any 7 amino acid residue substitutions set forth herein. In another embodiment, peptides are provided having in a region corresponding to SEQ ID NOs:1 or 2, a combination of any 8 amino acid residue substitutions set forth herein. In another embodiment, peptides are provided having in a region corresponding to SEQ ID NOs:1 or 2, a combination of any 9 amino acid residue substitutions set forth herein. In another embodiment, peptides are provided having in a region corresponding to SEQ ID NOs:1 or 2, a combination of any 10 amino acid residue substitutions set forth herein.

Accordingly, provided herein are polypeptides that are muteins of a D-AKAP2 polypeptide, wherein the mutein exhibits modified binding to a regulatory subunit of PKA compared to a native D-AKAP2. The native D-AKAP2 can comprise a sequence of amino acids set forth as SEQ ID NOs:1 or 2. Also provided are polypeptides that are muteins of a D-AKAP2 polypeptide, wherein the mutein exhibits modified binding to a regulatory subunit of PKA compared to a control. The control is a polypeptide that consists essentially of the sequence of amino acids set forth as SEQ ID NOs:1 or 2. In one embodiment, the polypeptides exhibit enhanced binding to PKA-RIα subunits. These peptides can further exhibit normal or reduced binding to PKA-RIIα subunits.

In another embodiment, the polypeptides exhibit enhanced binding to PKA-RIIα subunits relative to PKA-RIα subunits. The peptides can further exhibit normal or reduced binding to PKA-RIα subunits. In another embodiment, the peptides exhibit enhanced binding to both RIα and RIIα subunits. In another embodiment, the peptides exhibit reduced binding to PKA-RIα subunits. These peptides can further exhibit normal or increased binding to PKA-RIIα subunits. In another embodiment, the polypeptides exhibit reduced binding to PKA-RIIα. The peptides can further exhibit normal or increased binding to PKA-RIα subunits. In yet another embodiment, the peptides exhibit reduced binding to both RIα and RIIα subunits.

Also provided herein are variant D-AKAP2 peptides comprising one, two or more amino acid residue substitutions at positions corresponding to 1-27 of SEQ ID NOs:1 or 2, wherein the peptide further comprises a range of one or more amino acids, up to all of the amino acids, selected from amino acids 1-622 and 650-662 of SEQ ID NOs:64 or 65, wherein the one or more selected amino acids are contiguous with amino acid positions corresponding to 623-649 of SEQ ID NOs:64 or 65. In other words, polypeptides are provided herein that are at least 28 amino acids in length up to 662 amino acids that comprise the region corresponding to 623-649 of SEQ ID NOs:64 or 65, wherein the region corresponding to 623-649 of SEQ ID NOs:64 or 65 contains any combination of one, two or more of the amino acid residue substitutions provided herein, such as in the Examples or in the claims. Accordingly, in addition to containing single amino acid substitutions, D-AKAP2 proteins are provided having in a region corresponding to SEQ ID NOs:1 or 2 (e.g., the region corresponding to 623-649 of SEQ ID NOs:64 or 65), a combination of any 2, 3, 4, 5, 6, 7, 8, 9, 10 or more amino acid residue substitutions set forth herein, such as in the Examples and in the claims.

In other embodiments, the additional amino acid residues obtained from amino acids 1-622 and 650-662 of SEQ ID NOs:64 or 65 can contain conservative substitutions therein that do not alter the desired effect obtained by substituting one or more residues in the peptide region corresponding to 623-649 of SEQ ID NOs:64 or 65. In addition, these polypeptides can further comprise additional contiguous amino acids at either end of the D-AKAP2 variant protein, where the additional amino acid sequence can be used for a variety of purposes, such as protein targeting, to facilitate protein purification.

Peptide mimetics are molecules or compounds that mimic the necessary molecular conformation of a ligand or polypeptide for specific binding to a target molecule such as a PKA holoenzyme. In an exemplary embodiment, the peptides, polypeptides or peptide mimetics bind to the RI and/or RII regulatory subunits of the PKA holoenzyme. Such peptides and peptide mimetics include those of antibodies that specifically bind to a PKA holoenzyme and, typically, bind to the RI and/or RII regulatory subunits of a PKA holoenzyme. The peptides, polypeptides and peptide mimetics identified by methods provided herein can be agonists or antagonists of PKA holoenzymes.

Such peptides, polypeptides and peptide mimetics are useful for diagnosing, treating, preventing, and screening for a disease or disorder associated with PKA holoenzyme activity in a mammal. In addition, the peptides and peptide mimetics are useful for identifying, isolating, and purifying molecules or compounds that modulate the activity of a PKA holoenzyme, or specifically bind to a PKA holoenzyme, generally the RI and/or RII regulatory subunits of a PKA holoenzyme. Low molecular weight peptides and peptide mimetics can have strong binding properties to a target molecule, e.g., a PKA holoenzyme or the RI and/or RII regulatory subunits of a PKA holoenzyme.

Peptides, polypeptides and peptide mimetics that bind to PKA holoenzymes as described herein can be administered to mammals, including humans, to modulate PKA holoenzyme activity. Thus, methods for therapeutic treatment and prevention of neurodegenerative diseases, such as Alzheimer's Disease, cardiovascular disorders, cardiac disorders, particularly disorders associated with altered left ventricular function, cardiomyopathies, proliferative disorders, bipolar disorder and other neurological disorders, lipid-metabolism disorders, such as obesity, neoplastic disease, diabetes and certain peripheral retinopathies, such as retinitis pigmentosa, and autoimmune disorders, such as Lupus erythematosus, comprise administering a peptide, polypeptide or peptide mimetic compound in an amount sufficient to modulate such activity are provided. Also provided herein are methods for treating a subject having such a disease or disorder in which a peptide, polypeptide or peptide mimetic compound is administered to the subject in a therapeutically effective dose or amount.

Compositions containing the peptides, polypeptides or peptide mimetics provided herein can be administered for prophylactic and/or therapeutic treatments. In therapeutic applications, compositions can be administered to a patient already suffering from a disease, as described above, in an therapeutically effective amount sufficient to cure or at least partially arrest the symptoms of the disease and its complications. Amounts effective for this use will depend on the severity of the disease and the weight and general state of the patient and can be empirically determined.

In prophylactic applications, compositions containing the peptides, polypeptides and peptide mimetics are administered to a patient susceptible to or otherwise at risk of a particular disease. Such an amount is defined to be a "prophylactically effective dose". In this use, the precise amounts again depend on the patient's state of health and weight.

Accordingly, the peptides, polypeptides and peptide mimetics that bind to a PKA holoenzyme can be used to prepare pharmaceutical compositions containing, as an active ingredient, at least one of the peptides or peptide mimetics in association with a pharmaceutical carrier or diluent. The compounds can be administered, for example, by oral, pulmonary, parenteral (intramuscular, intraperitoneal, intravenous (IV) or subcutaneous injection), inhalation (via a fine powder formulation), transdermal, nasal, vaginal, rectal, or sublingual routes of administration and can be formulated in dosage forms appropriate for each route of administration (see, e.g., International PCT application Nos. WO93/25221 and WO94/17784; and European Patent Application 613,683).

Peptides, polypeptides and peptide mimetics that bind to PKA holoenzymes are useful in vitro as unique tools for understanding the biological role of PKA holoenzymes, including the evaluation of the many factors thought to influence, and be influenced by, the production of PKA holoenzyme. Such peptides, polypeptides and peptide mimetics are also useful in the development of other compounds that bind to and modulate the activity of a PKA holoenzyme, because such compounds provide important information on the relationship between structure and activity that should facilitate such development.

The peptides, polypeptides and peptide mimetics are also useful as competitive binders in assays to screen for new PKA holoenzymes or PKA holoenzyme agonists. In such assay embodiments, the compounds can be used without modification or can be modified in a variety of ways; for example, by labeling, such as covalently or non-covalently joining a moiety which directly or indirectly provides a detectable signal. In any of these assays, the materials thereto can be labeled either directly or indirectly. Exemplary labels for direct labeling include label groups such as: radiolabels such as $^{125}I$ enzymes (U.S. Pat. No. 3,645,090), peroxidase and alkaline phosphatase, and fluorescent labels (U.S. Pat. No. 3,940,475) capable of monitoring the change in fluorescence intensity, wavelength shift, or fluorescence polarization. Exemplary labels for indirect labeling include biotinylation of one constituent followed by binding to avidin coupled to one of the above label groups. The compounds can also include spacers or linkers in cases where the compounds are to be attached to a solid support.

In addition, based on their ability to bind to a PKA holoenzyme, the peptides, polypeptides and peptide mimetics can be used as reagents for detecting PKA holoenzymes in living cells, fixed cells, in biological fluids, in tissue homogenates and in purified, natural biological materials. For example, by labelling such peptides, polypeptides and peptide mimetics, cells having PKA holoenzymes can be identified. In addition, based on their ability to bind a PKA holoenzyme, the peptides, polypeptides and peptide mimetics can be used in in situ staining, FACS (fluorescence-activated cell sorting), Western blotting, ELISA and other analytical protocols. Based on their ability to bind to a PKA holoenzyme, the peptides, polypeptides and peptide mimetics can be used in purification of PKA holoenzymes or in purifying cells expressing the PKA holoenzymes, e.g., a polypeptide encoding the RI and/or RII regulatory subunits of a PKA holoenzyme.

The peptides, polypeptides and peptide mimetics can also be used as commercial reagents for various medical research and diagnostic uses. The activity of the peptides and peptide mimetics can be evaluated either in vitro or in vivo in one of the numerous models described in McDonald (1992) *Am. J. of Pediatric Hematology/Oncology,* 14:8-21.

D. Peptide, Polypeptide and Peptide Mimetic Therapy

Peptide analogs are commonly used in the pharmaceutical industry as non-peptide drugs with properties analogous to those of the template peptide. These types of non-peptide compounds are termed "peptide mimetics" or "peptidomimetics" (Luthman et al. *A Textbook of Drug Design and Development,* 14:386-406, 2nd Ed., Harwood Academic Publishers (1996); Joachim Grante (1994) *Angew. Chem. Int. Ed. Engl.,* 33:1699-1720; Fauchere (1986) *J. Adv. Drug Res.,* 15:29; Veber and Freidinger (1985) *TINS,* p. 392; and Evans et al. (1987) *J. Med. Chem.,* 30:1229). Peptide mimetics that are structurally similar to therapeutically useful D-AKAP2-derived peptides provided herein can be used to produce an equivalent or enhanced therapeutic or prophylactic effect. Preparation of peptidomimetics and structures thereof are known to those of skill in this art.

Systematic substitution of one or more amino acids of a consensus sequence with a D-amino acid of the same type (e.g., D-lysine in place of L-lysine) can be used to generate more stable peptides. In addition, constrained peptides containing a consensus sequence or a substantially identical consensus sequence variation can be generated by methods known in the art (Rizo et al. (1992) *An. Rev. Biochem.,* 61:387, incorporated herein by reference); for example, by adding internal cysteine residues capable of forming intramolecular disulfide bridges which cyclize the peptide.

Those skilled in the art appreciate that modifications can be made to the peptides and mimetics without deleteriously effecting the biological or functional activity of the peptide. Further, the skilled artisan would know how to design non-peptide structures in three dimensional terms, that mimic the peptides that bind to a target molecule, e.g., a PKA holoenzyme or, generally, the RI and/or RII subunit of PKA holoenzymes (see, e.g., Eck and Sprang (1989) *J. Biol. Chem.,* 26:17605-18795).

When used for diagnostic purposes, the peptides and peptide mimetics can be labeled with a detectable label and, accordingly, the peptides and peptide mimetics without such a label can serve as intermediates in the preparation of labeled peptides and peptide mimetics. Detectable labels can be molecules or compounds, which when covalently attached to the peptides and peptide mimetics, permit detection of the peptide and peptide mimetics in vivo, for example, in a patient to whom the peptide or peptide mimetic has been administered, or in vitro, e.g., in a sample or cells. Suitable detectable labels are well known in the art and include, by way of example, radioisotopes, fluorescent labels (e.g., fluorescein), and the like. The particular detectable label employed is not critical and is selected to be detectable at non-toxic levels. Selection of the such labels is well within the skill of the art.

Covalent attachment of a detectable label to the peptide or peptide mimetic is accomplished by conventional methods well known in the art. For example, when the $^{125}$I radioisotope is employed as the detectable label, covalent attachment of $^{125}$I to the peptide or the peptide mimetic can be achieved by incorporating the amino acid tyrosine into the peptide or peptide mimetic and then iodinating the peptide (see, e.g., Weaner et al. (1994) *Synthesis and Applications of Isotopically Labelled Compounds*, pp. 137-140). If tyrosine is not present in the peptide or peptide mimetic, incorporation of tyrosine to the N or C terminus of the peptide or peptide mimetic can be achieved by well known chemistry. Likewise, $^{32}$P can be incorporated onto the peptide or peptide mimetic as a phosphate moiety through, for example, a hydroxyl group on the peptide or peptide mimetic using conventional chemistry.

Labeling of peptidomimetics usually involves covalent attachment of one or more labels, directly or through a spacer (e.g., an amide group), to non-interfering position(s) on the peptidomimetic that are predicted by quantitative structure-activity data and/or molecular modeling. Such non-interfering positions generally are positions that do not form direct contacts with the macromolecule(s) to which the peptidomimetic binds to produce the therapeutic effect. Derivatization (e.g., labeling) of peptidomimetics should not substantially interfere with the desired biological or pharmacological activity of the peptidomimetic.

Peptides, polypeptides and peptide mimetics that can bind to a PKA holoenzyme or the RI and/or RII subunit of PKA holoenzymes and/or modulate the activity thereof, can be used for treatment of neurodegenerative diseases, such as Alzheimer's Disease, cardiovascular disorders, cardiac disorders, particularly disorders associated with altered left ventricular function, cardiomyopathies, proliferative disorders, bipolar disorder and other neurological disorders, lipid-metabolism disorders, such as obesity, neoplastic disease, diabetes, certain peripheral retinopathies, such as retinitis pigmentosa, and autoimmune disorders, such as Lupus erythematosus. The peptides, polypeptides and peptide mimetics can be delivered, in vivo or ex vivo, to the cells of a subject in need of treatment. Further, peptides which have a PKA holoenzyme activity can be delivered, in vivo or ex vivo, to cells which carry mutant or missing alleles encoding the PKA holoenzyme gene. Any of the techniques described herein or known to the skilled artisan can be used for preparation and in vivo or ex vivo delivery of such peptides, polypeptides and peptide mimetics that are substantially free of other human proteins. For example, the peptides, polypeptides and peptide mimetics can be readily prepared by expression in a microorganism or synthesis in vitro.

In particular embodiments, the peptides, polypeptides, and peptide mimetics provided herein are able to permeate cell membranes and thus affect binding of PKA to a D-AKAP2. For example, a peptide or mimetic may be modified to include a fatty-acid moiety by conventional methods, attached to either the amino terminus or the carboxy terminus of the peptide. Any fatty acid used in the art to achieve membrane-permeability of peptides may be employed, e.g., an N-stearylated peptide (Liotta et al. (1994) *J. Biol. Chem.*, 269:22996-23001) or N-myristoylated peptide (O'Brian et al. (1990) *Biochem. Pharmacol.*, 39:49-57; Eicholtz et al. (1993) *J. Biol. Chem.*, 268:1982-1986); and the like. Fatty acid-peptide conjugates have been used to inhibit protein kinase C (PKC) and tyrosine kinase activities in intact cells (Eichholtz et al. (1993) *J. Biol. Chem.*, 268:1982-1986; Liotta et al. (1994) *J. Biol. Chem.*, 269:22996-23001).

These peptides, polypeptides, and peptide mimetics may be introduced into cells by any conventional means. For example, a peptide may be incorporated into liposomes. Alternatively, the peptide can be formulated in a composition that includes an amphiphilic lipid, e.g., a head-to-tail amphiphile such as Lipofectin® or a cationic facial amphiphile (CFA) (a conjugate of polyamines and bile-acid-based amphiphiles).

The peptides or peptide mimetics can be introduced into cells, in vivo or ex vivo, by microinjection or by use of liposomes, for example. Alternatively, the peptides, polypeptides or peptide mimetics can be taken up by cells, in vivo or ex vivo, actively or by diffusion. In addition, extracellular application of the peptide, polypeptide or peptide mimetic can be sufficient to effect treatment of neurodegeneratives diseases, such as Alzheimer's Disease, cardiovascular disorders, cardiac disorders, particularly disorders associated with altered left ventricular function, cardiomyopathies, proliferative disorders, bipolar disorder and other neurological disorders, lipid-metabolism disorders, such as obesity, neoplastic disease, diabetes, certain peripheral retinopathies, such as retinitis pigmentosa, and autoimmune disorders, such as Lupus erythematosus. Other molecules, such as drugs or organic compounds, that: 1) bind to a PKA holoenzyme or RI and/or RII subunit thereof; or 2) have a similar function or activity to D-AKAP2 or a D-AKAP2 peptide or mimetic capable of binding a PKA holoenzyme or RI and/or RII subunit thereof, can be used in methods for treatment.

E. Rational Drug Design

The goal of rational drug design is to produce structural analogs of biologically active polypeptides or peptides of interest or of small molecules or peptide mimetics with which they interact (e.g., agonists and antagonists) in order to fashion drugs which are, e.g., more active or stable forms thereof; or which, for example, enhance or interfere with the function of a polypeptide in vivo (e.g., a PKA holoenzyme). In one approach, one first determines the three-dimensional structure of a protein of interest (e.g., a PKA holoenzyme or polypeptide having a RI and/or RII subunit) or, for example, of a PKA holoenzyme-D-AKAP2 complex, by X-ray crystallography, by computer modeling or most typically, by a combination of approaches. Also, useful information regarding the structure of a polypeptide can be gained by modeling based on the structure of homologous proteins. In addition, peptides can be analyzed by an alanine scan. In this technique, an amino acid residue is replaced by Ala, and its effect on the peptide's activity is determined. Each of the amino acid residues of the peptide is analyzed in this manner to determine the important regions of the peptide.

Also, a polypeptide or peptide that binds to a PKA holoenzyme or, generally, the RI and/or RII subunit of a PKA holoenzyme, can be selected by a functional assay, and then the crystal structure of this polypeptide or peptide can be determined. This approach can yield a pharmacophore upon which subsequent drug design can be based. Further, it is possible to bypass the crystallography altogether by generating anti-idiotypic polypeptides or peptides, (anti-ids) to a functional, pharmacologically active polypeptide or peptide that binds to a PKA holoenzyme or RI and/or RII subunit of a PKA holoenzyme. As a mirror image of a mirror image, the binding site of the anti-ids is expected to be an analog of the original target molecule, e.g., a PKA holoenzyme or polypeptide having a PKA holoenzyme. The anti-id can then be used to identify and isolate peptides from banks of chemically or biologically produced peptides. Selected peptides would then act as the pharmacophore.

Thus, one can design drugs which have, for example, improved activity or stability or which act as modulators (e.g., inhibitors, agonists or antagonists) of PKA holoenzyme activity, and are useful in the methods, particularly the methods for diagnosis, treatment, prevention, and screening of neurodegeneratives diseases, such as Alzheimer's Disease, cardiovascular disorders, cardiac disorders, particularly disorders associated with altered left ventricular function, cardiomyopathies, proliferative disorders, bipolar disorder and other neurological disorders, lipid-metabolism disorders, such as obesity, neoplastic disease, diabetes, certain peripheral retinopathies, such as retinitis pigmentosa, and autoimmune disorders, such as Lupus erythematosus. By virtue of the availability of nucleic acid that encodes PKA holoenzymes, sufficient amounts of the PKA holoenzyme can be made available to perform such analytical studies as X-ray crystallography. In addition, the knowledge of the amino acid sequence of a PKA holoenzyme or the RI and/or RII subunit thereof, e.g., the RI and/or RII subunit, can provide guidance on computer modeling techniques in place of, or in addition to, X-ray crystallography.

1. Methods of Identifying Additional Peptides and Peptide Mimetics That Bind to PKA Holoenzymes In addition to the D-AKAP2 derived peptides provided herein, other peptides having a differential binding affinity to the RI and/or RII subunits of PKA holoenzyme can be readily identified, for example, by random peptide diversity generating systems coupled with an affinity enrichment process. Specifically, random peptide diversity generating systems include the "peptides on plasmids" system (see, e.g., U.S. Pat. Nos. 5,270,170 and 5,338,665); the "peptides on phage" system (see, e.g., U.S. Pat. No. 6,121,238 and Cwirla et al. (1990) *Proc. Natl. Acad. Sci. USA*, 87:6378-6382); the "polysome system;" the "encoded synthetic library (ESL)" system; and the "very large scale immobilized polymer synthesis" system (see, e.g., U.S. Pat. No. 6,121,238; and Dower et al. (1991) *An. Rep. Med. Chem.*, 26:271-280.

For example, using the procedures described above, random peptides can generally be designed to have a defined number of amino acid residues in length (e.g., 12). To generate the collection of oligonucleotides encoding the random peptides, the codon motif (NNK)x, where N is nucleotide A, C, G, or T (equimolar; depending on the methodology employed, other nucleotides can be employed), K is G or T (equimolar), and x is an integer corresponding to the number of amino acids in the peptide (e.g., 12) can be used to specify any one of the 32 possible codons resulting from the NNK motif: 1 for each of 12 amino acids, 2 for each of 5 amino acids, 3 for each of 3 amino acids, and only one of the three stop codons. Thus, the NNK motif encodes all of the amino acids, encodes only one stop codon, and reduces codon bias.

The random peptides can be presented, for example, either on the surface of a phage particle, as part of a fusion protein containing either the pIII or the pVIII coat protein of a phage fd derivative (peptides on phage) or as a fusion protein with the Lacl peptide fusion protein bound to a plasmid (peptides on plasmids). The phage or plasmids, including the DNA encoding the peptides, can be identified and isolated by an affinity enrichment process using immobilized PKA holoenzyme having a RI and/or RII subunit. The affinity enrichment process, sometimes called "panning," typically involves multiple rounds of incubating the phage, plasmids, or polysomes with the immobilized PKA holoenzyme or RI and/or RII subunits thereof, collecting the phage, plasmids, or polysomes that bind to the PKA holoenzyme (along with the accompanying DNA or mRNA), and producing more of the phage or plasmids (along with the accompanying Lacl-peptide fusion protein) collected.

2. Characteristics of Peptides and Peptide Mimetics

Among the peptides, polypeptides and peptide mimetics for therapeutic application are those of having molecular weights from about 250 to about 8,000 daltons. If such peptides are oligomerized, dimerized and/or derivatized with a hydrophilic polymer (e.g., to increase the affinity and/or activity of the compounds), the molecular weights of such peptides can be substantially greater and can range anywhere from about 500 to about 120,000 daltons, generally from about 8,000 to about 80,000 daltons. Such peptides can contain 9 or more amino acids that are naturally occurring or synthetic (non-naturally occurring) amino acids. One skilled in the art can determine the affinity and molecular weight of the peptides and peptide mimetics suitable for therapeutic and/or diagnostic purposes (e.g., see Dower et al., U.S. Pat. No. 6,121,238).

The peptides can be covalently attached to one or more of a variety of hydrophilic polymers. Suitable hydrophilic polymers include, but are not limited to, polyalkylethers as exemplified by polyethylene glycol and polypropylene glycol, polylactic acid, polyglycolic acid, polyoxyalkenes, polyvinylalcohol, polyvinylpyrrolidone, cellulose and cellulose derivatives, dextran and dextran derivatives. When the peptide compounds are derivatized with such polymers, their solubility and circulation half-lives can be increased with little, if any, diminishment in their binding activity. The peptide compounds can be dimerized and each of the dimeric subunits can be covalently attached to a hydrophilic polymer. The peptide compounds can be PEGylated, i.e., covalently attached to polyethylene glycol (PEG).

F. Methods of Preparing Peptides and Peptide Mimetics

D-AKAP2 based peptides provided herein that bind to PKA holoenzymes can be prepared by classical methods known in the art, for example, by using standard solid phase techniques. The standard methods include exclusive solid phase synthesis, partial solid phase synthesis methods, fragment condensation, classical solution synthesis, and even by recombinant DNA technology (see, e.g., Merrifield (1963) *J. Am. Chem. Soc.*, 85:2149, incorporated herein by reference.)

Using the "encoded synthetic library" or "very large scale immobilized polymer synthesis" systems (see, e.g., U.S. Pat. Nos. 5,925,525, and 5,902,723), the minimum size of a peptide with the activity of interest can be determined. In addition, all peptides that form the group of peptides that differ from the desired motif (or the minimum size of that motif) in one, two, or more residues can be prepared. This collection of peptides then can be screened for the ability to bind to the target molecule, e.g., PKA holoenzyme or, generally, the RI and/or RII subunit of a PKA holoenzyme. This immobilized polymer synthesis system or other peptide synthesis methods can also be used to synthesize truncation analogs and deletion analogs and combinations of truncation and deletion analogs of the peptide compounds.

These procedures can also be used to synthesize peptides in which amino acids other than the 20 naturally occurring, genetically encoded amino acids are substituted at one, two, or more positions of the peptide. For instance, naphthylalanine can be substituted for tryptophan, facilitating synthesis. Other synthetic amino acids that can be substituted into the peptides include L-hydroxypropyl, L-3,4-dihydroxy-phenylalanyl, D amino acids such as L-d-hydroxylysyl and D-d-methylalanyl, L-α-methylalanyl, β amino acids, and isoquinolyl. D amino acids and non-naturally occurring synthetic amino acids can also be incorporated into the peptides (see, e.g., Roberts et al. (1983) *Unusual Amino/Acids in Peptide Synthesis*, 5(6):341-449).

The peptides can also be modified by phosphorylation (see, e.g., W. Bannwarth et al. (1996) *Biorganic and Medicinal Chemistry Letters*, 6(17):2141-2146), and other methods for making peptide derivatives (see, e.g., Hruby et al. (1990) *Biochem. J.*, 268(2):249-262). Thus, peptide compounds also serve as a basis to prepare peptide mimetics with similar or improved biological activity.

Those of skill in the art recognize that a variety of techniques are available for constructing peptide mimetics with the same or similar desired biological activity as the corresponding peptide compound but with more favorable activity than the peptide with respect to solubility, stability, and susceptibility to hydrolysis and proteolysis (see, e.g., Morgan et al. (1989) *An. Rep. Med. Chem.*, 24:243-252). Methods for preparing peptide mimetics modified at the N-terminal amino group, the C-terminal carboxyl group, and/or changing one or more of the amido linkages in the peptide to a non-amido linkage are known to those of skill in the art.

Amino terminus modifications include, but are not limited to, alkylating, acetylating and adding a carbobenzoyl group, forming a succinimide group (see, e.g., Murray et al. (1995) *Burger's Medicinal Chemistry and Drug Discovery*, 5th ed., Vol. 1, Manfred E. Wolf, ed., John Wiley and Sons, Inc.). C-terminal modifications include mimetics wherein the C-terminal carboxyl group is replaced by an ester, an amide or modifications to form a cyclic peptide.

In addition to N-terminal and C-terminal modifications, the peptide compounds, including peptide mimetics, can advantageously be modified with or covalently coupled to one or more of a variety of hydrophilic polymers. It has been found that when peptide compounds are derivatized with a hydrophilic polymer, their solubility and circulation half-lives can be increased and their immunogenicity is masked, with little, if any, diminishment in their binding activity. Suitable nonproteinaceous polymers include, but are not limited to, polyalkylethers as exemplified by polyethylene glycol and polypropylene glycol, polylactic acid, polyglycolic acid, polyoxyalkenes, polyvinylalcohol, polyvinylpyrrolidone, cellulose and cellulose derivatives, dextran and dextran derivatives. Generally, such hydrophilic polymers have an average molecular weight ranging from about 500 to about 100,000 daltons, including from about 2,000 to about 40,000 daltons and, from about 5,000 to about 20,000 daltons. The hydrophilic polymers also can have average molecular weights of about 5,000 daltons, 10,000 daltons and 20,000 daltons.

Methods for derivatizing peptide compounds or for coupling peptides to such polymers have been described (see, e.g., Zallipsky (1995) *Bioconjugate Chem.*, 6:150-165; Monfardini et al. (1995) *Bioconjugate Chem.*, 6:62-69; U.S. Pat. No. 4,640,835; U.S. Pat. No. 4,496,689; U.S. Pat. No. 4,301,144; U.S. Pat. No. 4,670,417; U.S. Pat. No. 4,791,192; U.S. Pat. No. 4,179,337 and WO95/34326, all of which are incorporated by reference in their entirety herein).

Other methods for making peptide derivatives are described, for example, in Hruby et al. (1990) *Biochem J.*, 268(2):249-262, which is incorporated herein by reference. Thus, the peptide compounds also serve as structural models for non-peptidic compounds with similar biological activity. Those of skill in the art recognize that a variety of techniques are available for constructing compounds with the same or similar desired biological activity as a particular peptide compound but with more favorable activity with respect to solubility, stability, and susceptibility to hydrolysis and proteolysis (see, e.g., Morgan et al. (1989) *An. Rep. Med. Chem.*, 24:243-252, incorporated herein by reference). These techniques include replacing the peptide backbone with a backbone composed of phosphonates, amidates, carbamates, sulfonamides, secondary amines, and N-methylamino acids.

Peptide compounds can exist in a cyclized form with an intramolecular disulfide bond between the thiol groups of the cysteines. Alternatively, an intermolecular disulfide bond between the thiol groups of the cysteines can be produced to yield a dimeric (or higher oligomeric) compound. One or more of the cysteine residues can also be substituted with a homocysteine.

G. Transgenic Animals

Methods for making transgenic animals using a variety of transgenes have been described in Wagner et al. (1981) *Proc. Nat. Acad. Sci. USA*, 78:5016-5020; Stewart et al. (1982) *Science*, 217:1046-1048; Constantini et al. (1981) *Nature*, 294:92-94; Lacy et al. (1983) *Cell*, 34:343-358; McKnight et al. (1983) *Cell*, 34:335-341; Brinstar et al. (1983) *Nature*, 306:332-336; Palmiter et al. (1982) *Nature*, 300:611-615; Palmiter et al. (1982) *Cell*, 29:701-710, and Palmiter et al. (1983) *Science*, 222:809-814. Such methods are described in U.S. Pat. Nos. 6,175,057; 6,180,849; and 6,133,502.

The term "transgene" is used herein to describe genetic material that has been or is about to be artificially inserted into the genome of a mammalian cell, particularly a mammalian cell of a living animal. The transgene is used to transform a cell, meaning that a permanent or transient genetic change, preferably a permanent genetic change, is induced in a cell following incorporation of exogenous DNA. A permanent genetic change is generally achieved by introduction of the DNA into the genome of the cell. Vectors for stable integration include, but are not limited to, plasmids, retroviruses and other animal viruses and YACS. Of interest are transgenic mammals, including, but are not limited to, cows, pigs, goats, horses and others, and particularly rodents, including rats and mice. Preferably, the transgenic-animals are mice.

Transgenic animals contain an exogenous nucleic acid sequence present as an extrachromosomal element or stably integrated in all or a portion of its cells, especially germ cells. Unless otherwise indicated, it will be assumed that a transgenic animal comprises stable changes to the germline sequence. During the initial construction of the animal, "chimeras" or "chimeric animals" are generated, in which only a subset of cells have the altered genome. Chimeras are primarily used for breeding purposes in order to generate the desired transgenic animal. Animals having a heterozygous alteration are generated by breeding of chimeras. Male and female heterozygotes are typically bred to generate homozygous animals.

The exogenous gene is usually either from a different species than the animal host, or is otherwise altered in its coding or non-coding sequence. The introduced gene may be a wild-type gene, naturally occurring polymorphism or a genetically manipulated sequence, for example having deletions, substitutions or insertions in the coding or non-coding regions. When the introduced gene is a coding sequence, it is usually operably linked to a promoter, which may be constitutive or inducible, and other regulatory sequences required for expression in the host animal.

Transgenic animals can comprise other genetic alterations in addition to the presence of alleles of AKAP genes. For example, the genome can be altered to affect the function of the endogenous genes, contain marker genes, or contain other genetic alterations (e.g., alleles of genes associated with cardiovascular disease).

A "knock-out" of a gene means an alteration in the sequence of the gene that results in a decrease of function of the target gene, preferably such that target gene expression is undetectable or insignificant. A knock-out of an endogenous AKAP gene means that function of the gene has been substantially decreased so that expression is not detectable or only present at insignificant levels. "Knock-out" transgenics can be transgenic animals having a heterozygous knock-out of an AKAP gene or a homozygous knock-out. "Knock-outs" also include conditional knock-outs. As used herein, "conditional" in reference to "knock-outs" and "knock-ins" means alteration of the target gene can occur upon, for example, exposure of the animal to a substance that promotes target gene alteration, introduction of an enzyme that promotes recombination at the target gene site (e.g., Cre in the Cre-lox system), or other method for directing the target gene alteration postnatally.

A "knock-in" transgenic animal refers to an animal that has had a modified gene introduced into its genome, wherein the modified gene can be of exogenous or endogenous origin (see, e.g., Roemer et al. (1991) New Biol., 3:331). Accordingly, a "knock-in" of a target gene means an alteration in a host cell genome that results in either expression of an altered target gene; or altered expression (e.g., increased (including ectopic)) of the target gene, e.g., by introduction of an additional copy of the target gene, or by operatively inserting a regulatory sequence that provides for enhanced expression of an endogenous copy of the target gene. "Knock-in" transgenics of interest can be transgenic animals having a knock-in of an AKAP gene. Such transgenics can be heterozygous or homozygous for the knock-in gene. "Knock-ins" also encompass conditional knock-ins. As used herein, "knock-in" transgenic animals also encompasses animals in which an animal gene is replaced by the human equivalent within the genome of that animal. These transgenic knock-in animals are useful for drug discovery, for target validation, where the compound is specific for the human target. Transgenic knock-ins can by produced using homologous recombination, using transposons (e.g., Westphal et al. (1997) Curr. Biol., 7:530, and the like), using mutant recombination sites (e.g., Araki et al. (1997) NAR, 25:868, and the like), using PCR (e.g., Zhang et al. Biotechniques, 25:784, and the like), and the like.

For example, the binding data generated herein related to certain amino acid positions within the 27-mer AKB binding domain is used to knock-in specific amino acids at specific positions in the genome of cells and organisms (e.g. animals, cells) to change the binding ratio of both PKA-RIα and PKA-RIIα subunits to its target protein D-AKAP2 in vivo. Such a changed binding ratio is contemplated herein to produce a changed phenotype useful to elucidate the biological function of D-AKAP2 and PKA subunits and their contribution to the manifestation of diseases set forth herein. Likewise, the binding data generated herein related to certain amino acid positions within the 27-mer AKB binding domain is used to knock-in specific amino acids at specific positions in the genome of cells and organisms (e.g., animals, cells) to disrupt the binding of one particular PKA-R subunit isoform to D-AKAP2 in vivo. Such a binding disruption is contemplated herein to cause a specific loss of function of D-AKAP2 resulting in a changed phenotype useful to elucidate the biological function of D-AKAP2 and PKA subunits and their contribution to the manifestation of diseases set forth herein.

The transgenic knock-in cellular systems or animals provided herein are useful to screen chemical compound libraries for the purpose of drug discovery. In addition, these transgenic knock-in cellular systems or animals are useful in assays along the entire drug development process.

A construct is suitable for use in the generation of transgenic animals if it allows the desired level of expression of an AKAP encoding sequence. Methods of isolating and cloning a desired sequence, as well as suitable constructs for expression of a selected sequence in a host animal, are well known in the art and are described below.

For the introduction of a gene into the subject animal, it is generally advantageous to use the gene as a gene construct wherein the gene is ligated downstream of a promoter capable of and operably linked to expressing the gene in the subject animal cells. Specifically, a transgenic non-human mammal showing high expression of the desired gene can be created by microinjecting a vector ligated with said gene into a fertilized egg of the subject non-human mammal (e.g., rat fertilized egg) downstream of various promoters capable of expressing the protein and/or the corresponding protein derived from various mammals (rabbits, dogs, cats, guinea pigs, hamsters, rats, mice etc., preferably rats etc.)

Useful vectors include *Escherichia coli*-derived plasmids, *Bacillus subtilis*-derived plasmids, yeast-derived plasmids, bacteriophages such as lambda, phage, retroviruses such as Moloney leukemia virus, and animal viruses such as vaccinia virus or baculovirus.

Useful promoters for such gene expression regulation include, for example, promoters for genes derived from viruses (cytomegalovirus, Moloney leukemia virus, JC virus, breast cancer virus, etc.), and promoters for genes derived from various mammals (humans, rabbits, dogs, cats, guinea pigs, hamsters, rats, mice, etc.), and birds (chickens, etc.) (e.g., genes for albumin, insulin II, erythropoietin, endothelin, osteocalcin, muscular creatine kinase, platelet-derived growth factor beta, keratins K1, K10 and K14, collagen types I and II, atrial natriuretic factor, dopamine beta-hydroxylase, endothelial receptor tyrosine kinase (generally abbreviated Tie2), sodium-potassium adenosine triphosphorylase (generally abbreviated Na,K-ATPase), neurofilament light chain, metallothioneins I and IIA, metalloproteinase I tissue inhibitor, MHC class I antigen (generally abbreviated H-2L), smooth muscle alpha actin, polypeptide chain elongation factor 1 alpha (EF-1 alpha), beta actin, alpha and beta myosin heavy chains, myosin light chains 1 and 2, myelin base protein, serum amyloid component, myoglobin, renin, etc.).

It is preferable that the above-mentioned vectors have a sequence for terminating the transcription of the desired messenger RNA in the transgenic animal (generally referred to as terminator); for example, gene expression can be manipulated using a sequence with such function contained in various genes derived from viruses, mammals and birds. Preferably, the simian virus SV40 terminator, etc., are commonly used. Additionally, for the purpose of increasing the expression of the desired gene, the splicing signal and enhancer region of each gene, a portion of the intron of a eukaryotic organism gene may be ligated 5' upstream of the promoter region, or between the promoter region and the translational region, or 3' downstream of the translational region as desired.

A translational region for a protein of interest can be obtained using the entire or portion of genomic DNA of blood, kidney or fibroblast origin from various mammals (humans, rabbits, dogs, cats, guinea pigs, hamsters, rats, mice, etc.), or of various commercially available genomic DNA libraries, as a starting material, or using complementary DNA prepared by a known method from RNA of blood, kidney or fibroblast origin as a starting material. Also, an exogenous gene can be obtained using complementary DNA prepared by a known method from RNA of human fibroblast origin as a starting material. All these translational regions can be used in transgenic animals.

To obtain the translational region, it is possible to prepare DNA incorporating an exogenous gene encoding the protein of interest in which the gene is ligated downstream of the above-mentioned promoter (preferably upstream of the translation termination site) as a gene construct capable of being expressed in the transgenic animal.

DNA constructs for random integration need not include regions of homology to mediate recombination. Where homologous recombination is desired, the DNA constructs will comprise at least a portion of the target gene with the desired genetic modification, and will include regions of homology to the target locus. Conveniently, markers for positive and negative selection are included. Methods for generating cells having targeted gene modifications through homologous recombination are known in the art. For various techniques for transfecting mammalian cells, see Keown et al. (1990) *Meth. Enzymol.*, 185:527-537.

The transgenic animal can be created by introducing an AKAP gene construct into, for example, an unfertilized egg, a fertilized egg, a spermatozoon or a germinal cell containing a primordial germinal cell thereof, preferably in the embryogenic stage in the development of a non-human mammal (more preferably in the single-cell or fertilized cell stage and generally before the 8-cell phase), by standard means, such as the calcium phosphate method, the electric pulse method, the lipofection method, the agglutination method, the microinjection method, the particle gun method, the DEAE-dextran method and other such method. Also, it is possible to introduce a desired AKAP gene into a somatic cell, a living organ, a tissue cell or other cell, by gene transformation methods, and use it for cell culture, tissue culture and any other method of propagation. Furthermore, these cells may be fused with the above-described germinal cell by a commonly known cell fusion method to create a transgenic animal.

For embryonic stem (ES) cells, an ES cell line may be employed, or embryonic cells may be obtained freshly from a host, e.g., mouse, rat, guinea pig, etc. Such cells are grown on an appropriate fibroblast-feeder layer or grown in the presence of appropriate growth factors, such as leukemia inhibiting factor (LIF). When ES cells have been transformed, they may be used to produce transgenic animals. After transformation, the cells are plated onto a feeder layer in an appropriate medium. Cells containing the construct may be detected by employing a selective medium. After sufficient time for colonies to grow, they are picked and analyzed for the occurrence of homologous recombination or integration of the construct. Those colonies that are positive may then be used for embryo manipulation and blastocyst injection. Blastocysts are obtained from 4 to 6 week old superovulated females. The ES cells are trypsinized, and the modified cells are injected into the blastocoel of the blastocyst. After injection, the blastocysts are returned to each uterine horn of pseudopregnant females. Females are then allowed to go to term and the resulting litters screened for mutant cells having the construct. By providing for a different phenotype of the blastocyst and the ES cells, chimeric progeny can be readily detected. The chimeric animals are screened for the presence of the modified gene and males and females having the modification are mated to produce homozygous progeny. If the gene alterations cause lethality at some point in development, tissues or organs can be maintained as allogeneic or congenic grafts or transplants, or in vitro culture.

Animals containing more than one transgene, such as allelic variants of AKAP genes and/or other genes associated with morbidity and/or mortality can be made by sequentially introducing individual alleles into an animal in order to produce the desired phenotype (manifestation of morbidity and/or predisposition to early mortality). In addition, animals containing one or more amino acid substitutions with that same transgene, such as D-AKAP2 can be made by sequentially introducing individual amino acid substitutions, or introducing one or more substitutions in a single construct, into an animal in order to produce the desired genotype and/or phenotype (manifestation of morbidity and/or predisposition to early mortality). For example, transgenic animals having one or more amino acid substitutions in the D-AKAP2 gene, include transgenic animals having a combination of 2, 3, 4, 5, 6, 7, 8, 9, 10 or more of the amino acid residue substitutions set forth herein, such as, but not limited to, those described above and in the Examples, or in the claims.

Accordingly, provided herein are transgenic non-human knock-in animals comprising a gene encoding the animal homolog of human D-AKAP2, wherein said gene has been modified to encode any combination of one or more amino acid substitutions in a 27-mer PKA binding region of the animal protein homolog of human D-AKAP2 corresponding to amino acids 623-649 of human D-AKAP2 set forth in SEQ ID NOs:63-65; or SEQ ID NOs:1 or 2. In one embodiment, the amino acid substitution in the animal homolog of human D-AKAP2 is selected from the group consisting of substitutions that correspond to the substitution in SEQ ID NOs:63-65 of one, two or more: of Q at residue 631 with F, I, L, V, H, M, R, T, W or Y; of L at residue 634 with F, W or Y; of V at residue 643 with I, L or W; and of M at residue 647 with F, I, L, T, V, W or Y. In this embodiment, the modified animal protein homolog of human D-AKAP2 can exhibit a preferred or exclusive binding to PKA-RIα subunits relative to PKA-RIIα subunits, or enhanced binding to both RIα and RIIα subunits, compared to the native unmodified animal protein homolog of human D-AKAP2.

In another embodiment, the amino acid substitution in the animal homolog of human D-AKAP2 is selected from the group consisting of substitutions that correspond to the substitution in SEQ ID NOs:63-65 of one, two or more: of L at residue 634 with A, C, or K; of A at residue 635 with F, H, I, K, L, M, N or S; of W at residue 636 with C; of K at residue 637 with C; of K at residue 640 with C; of M at residue 641 with C; of S at residue 644 with C; and of D at residue 645 with C. In this embodiment, the modified animal protein homolog of human D-AKAP2 can exhibit a preferred or exclusive binding to PKA-RIIα subunits relative to PKA-RIα subunits, compared to the native unmodified animal protein homolog of human D-AKAP2.

In another embodiment, the animal is a mouse, and wherein the amino acid substitution in the mouse D-AKAP2 is selected from the group consisting of substitutions that correspond to the substitution in SEQ ID NOs:55 or 56 of one, two or more: of Q at residue 341 with F, I, L, V, H, M, R, T, W or Y; of L at residue 344 with F, W or Y; of V at residue 353 with I, L or W; and of M at residue 357 with F, I, L, T, V, W or Y. In this embodiment, the modified animal protein homolog of human D-AKAP2 is mouse D-AKAP2 that exhibits a preferred or exclusive binding to PKA-RIα subunits relative to PKA-RIIα subunits, or enhanced binding to both RIα and RIIα subunits, compared to the native unmodified mouse D-AKAP2. In a particular embodiment, the amino acid substitution in the mouse D-AKAP2 corresponds to a single amino acid substitution in SEQ ID NOs:55 or 56 of Q at residue 341 with 1, and wherein the modified mouse D-AKAP2 exhibits a enhanced binding to PKA-RIα subunits, and normal binding to PKA-RIIα subunits compared to the native unmodified mouse D-AKAP2. In another embodiment, the amino acid substitution in the mouse D-AKAP2 corresponds to a single amino acid substitution in SEQ ID NOs:55 or 56 of V at residue 353 with W, and wherein the modified mouse D-AKAP2 exhibits a normal binding to PKA-RIα subunits, and disrupted or decreased binding to PKA-RIIα subunits compared to the native unmodified mouse D-AKAP2. In another embodiment, the amino acid substitution in the mouse D-AKAP2 corresponds to a triple amino acid substitution in SEQ ID NOs:55 or 56 of Q at residue 341 with F, of V at residue 353 with W, and of M at residue 357 with F, and wherein the modified mouse D-AKAP2 exhibits increased binding to RIα and decreased binding affinity for RIIα. In a particular embodiment, the modified mouse D-AKAP2 having the triple amino acid substitution exhibits approximately 10-fold increased binding to RIα and approximately 220-fold decreased binding affinity for RIIα.

In another embodiment, the animal is a mouse, and wherein the modified animal protein homolog of human D-AKAP2 is mouse D-AKAP2 that exhibits a preferred or exclusive binding to PKA-RIIα subunits relative to PKA-RIα subunits, compared to the native unmodified mouse D-AKAP2; and wherein the amino acid substitution in the mouse D-AKAP2 is selected from the group consisting of substitutions that correspond to the substitution in SEQ ID NOs:55 or 56 of one, two or more: of L at residue 344 with A, C, or K; of A at residue 345 with F, H, I, K, L, M, N or S; of W at residue 346 with C; of K at residue 347 with C; of K at residue 350 with C; of M at residue 351 with C; of S at residue 354 with C; and of D at residue 355 with C. In a particular embodiment, the amino acid substitution in the mouse D-AKAP2 corresponds to a single amino acid substitution in SEQ ID NOs:55 or 56 of A at residue 345 with L, and wherein the modified mouse D-AKAP2 exhibits normal binding to PKA-RIIα subunits, and disrupted binding to PKA-RIα subunits compared to the native unmodified mouse D-AKAP2.

H. Protein and Polypeptide Detection

1. Expression of Protein in a Cell Line

Using the nucleic acids described herein, variant D-AKAP2 proteins (referred to herein as D-AKAP2 muteins) may be expressed in a recombinantly engineered cell such as bacteria, yeast, insect, mammalian, or plant cells. Those of skill in the art are knowledgeable in the numerous expression systems available for expression of a nucleic acid encoding proteins such as polymorphic human D-AKAP2 proteins. Accordingly, provided herein are cells, comprising heterologous nucleic acid that encodes a mammalian D-AKAP2 variant protein or portion that exhibits a preferred or exclusive binding to PKA-RIα subunits relative to PKA-RIIα subunits; or enhanced binding to both RIα and RIIα subunits, compared to the unmodified full length D-AKAP2 protein or SEQ ID NOs:1 or 2. In one embodiment, the D-AKAP2 variant protein or portion thereof comprises at least one single amino acid substitution in the mammalian D-AKAP2 selected from the group consisting of substitutions that correspond to the substitution in SEQ ID NOs:64 or 65 of one, two or more: of Q at residue 631 with F, I, L, V, H, M, R, T, W or Y; of L at residue 634 with F, W or Y; of V at residue 643 with I, L or W; and of M at residue 647 with F, I, L, T, V, W or Y.

Also provided herein are cells comprising heterologous nucleic acid that encodes a mammalian D-AKAP2 variant protein or portion that exhibits a preferred or exclusive binding to PKA-RIIa subunits relative to PKA-RIα subunits, compared to the unmodified full length D-AKAP2 protein or SEQ ID NOs:1 or 2. In one embodiment, the D-AKAP2 variant protein or portion thereof comprises at least one single amino acid substitution in the mammalian D-AKAP2 selected from the group consisting of substitutions that correspond to the substitution in SEQ ID NOs:64 or 65 of one, two or more: of L at residue 634 with A, C, or K; of A at residue 635 with F, H, I, K, L, M, N or S; of W at residue 636 with C; of K at residue 637 with C; of K at residue 640 with C; of M at residue 641 with C; of S at residue 644 with C; and of D at residue 645 with C.

Also provided herein are cells, comprising heterologous nucleic acid that encodes a mammalian D-AKAP2 variant protein or portion comprising any one or more of the peptide sequences provided herein at the corresponding region in the mammalian D-AKAP2 variant protein.

2. Expression of Variant D-AKAP2 Proteins

Provided herein are D-AKAP2 muteins, or polypeptide fragments thereof, comprising a peptide region corresponding to an A-Kinase binding (AKB) domain set forth as amino acids 623-649 of SEQ ID NOs:64 or 65. In one embodiment, the sequence of said AKB domain peptide region corresponds to any of the peptide sequences described herein and in the Examples as well as in the claims. In one embodiment, the D-AKAP2 mutein can have 28 or more amino acid residues, wherein the amino acid sequence of the D-AKAP2 mutein additional to AKB domain peptide region, is 1 to 635 amino acids in length and corresponds to a contiguous region from amino acids 1-622 and/or 650-662 of SEQ ID NOs:64 or 65. In another embodiment, the D-AKAP2 mutein can be 662 amino acids in length, and further comprises amino acids 1-622 and 650-662 of SEQ ID NOs:64 or 65. Also provided are isolated nucleic acid molecules, vectors, and cells containing these vectors, comprising a sequence of nucleotides that encodes the D-AKAP2 mutein provided herein. Also provided herein are methods of producing a D-AKAP2 mutein by growing the cells comprising a vector under conditions whereby the D-AKAP2 mutein is expressed; and isolating the mutein. The cell can be any animal cell (e.g., mammalian or human), yeast cell, insect cell or bacterial cell.

The isolated nucleic acid encoding a full-length mammalian (e.g., human, mouse, and the like) D-AKAP2 protein, mutein provided herein, or a portion thereof, such as a peptide fragment containing one or more of the biologically significant variant sites set forth herein in Examples 5-9, may be introduced into a vector for transfer into host cells. Fragments of the polymorphic mammalian, e.g., human, D-AKAP2 proteins can be produced by those skilled in the art, without undue experimentation, by eliminating portions of the coding sequence from the isolated nucleic acids encoding the full-length proteins.

The isolated nucleic acid encoding a full length D-AKAP2 protein, mutein or portion thereof can be modified to use a preferred codon bias to increase the expression level of the AKAP protein. The codon usage of the target organism or cell for expression can be determined by methods such as described in U.S. Pat. Nos. 5,082,767 and 4,562,639 (incorporated herein by reference). The isolated nucleic acid can then be modified by mutagenesis, recombination, or produced by synthetic DNA synthesis or other techniques known in the art such that the modified nucleic acid encoding the D-AKAP2 protein, mutein or portion thereof has at least one codon optimized for expression in the target organism or host cell. Using such methods, the expression of D-AKAP2 protein, mutein or portion thereof can be increased above the expression of the unmodified sequences. Conversely, if lower expression is desired, the codon usage of the nucleic acid encoding the D-AKAP2 protein, mutein or portion thereof can be modified to select for non-preferred or less preferred codons of the target organism or cell, for expression such as by methods described in U.S. Pat. Nos. 5,786,464 and 6,114,148 (incorporated herein by reference).

Expression vectors are used to express the protein in the desired host cell. An expression vector includes vectors capable of expressing nucleic acids that are operatively linked with regulatory sequences, such as promoter regions, that are capable of effecting expression of such nucleic acids. Thus, an expression vector refers to a recombinant DNA or RNA construct, such as a plasmid, a phage, recombinant virus or other vector that, upon introduction into an appropriate host cell, results in expression of the cloned DNA. Appropriate expression vectors are well known to those of skill in the art and include those that are replicable in eukaryotic cells and/or prokaryotic cells and those that remain episomal or those which integrate into the host cell genome. Such plasmids for expression of polymorphic mammalian, e.g., human, D-AKAP2-encoding nucleic acids in eukaryotic host cells, particularly mammalian cells, include cytomegalovirus (CMV) promoter-containing vectors, such as PCMV5, the pSV2dhfr expression vectors, which contain the SV40 early promoter, mouse dhfr gene, SV40 polyadenylation and splice sites and sequences necessary for maintaining the vector in bacteria, and MMTV promoter-based vectors.

Expression vectors can be constructed which up-regulate or down-regulate expression of D-AKAP2, a mutein or portion thereof in a host cell or transgenic animal. Methods for down-regulation include antisense expression, RNAi constructs, ribozyme expression and other methods well known in the art. Such expression vectors may include the full length nucleotide sequence of D-AKAP2 sequence or mutein provided herein or a portion thereof. Vectors can be designed that are specific for down-regulating expression a specific allele of D-AKAP2, for example down-regulation of the Val(646) variant of D-AKAP2. Vectors can also be designed to down-regulate expression of all or most of alleles of D-AKAP2. Such vectors can also be designed to down-regulate D-AKAP2 homologs. Similarly, expression vectors can be designed which up-regulate D-AKAP2 expression or which express a high amount of a particular D-AKAP2 mutein or portion thereof. For example, promoters can be used which are known to regulate high levels of expression, for example viral promoters and other promoters such as described herein and known in the art. Codon optimization, as described above, can also be used to increase expression of full length D-AKAP2, a mutein or portion thereof. Another method of up-regulation is ectopic expression, the expression of D-AKAP2, a mutein or portion thereof in a cell-type or tissue that does not normally express D-AKAP2. Such ectopic expression can be accomplished by using tissue-specific or regulatable promoters. One example of such a regulatable promoter is the Tet-on/Tet-off system (available from Clontech, BD Biosciences, Palo Alto Calif.) in which gene expression is regulated by the administration of tetracycline or related analogs.

The nucleic acids encoding polymorphic human D-AKAP2 proteins, and vectors and cells containing the nucleic acids as provided herein permit production of the polymorphic protein variants, as well as antibodies to the proteins. This provides a means to prepare synthetic or recombinant polymorphic human D-AKAP2 proteins and fragments thereof that are substantially free of contamination from other AKAPs and proteins in general, the presence of which can interfere with analysis of the polymorphic proteins. In addition, the polymorphic proteins may be expressed in combination with selected other proteins that D-AKAP2 may associate with in cells. The ability to selectively express the polymorphic D-AKAP2 proteins alone or in combination with other selected proteins makes it possible to observe the functioning of the recombinant polymorphic proteins within the environment of a cell. The expression of isolated nucleic acids encoding an AKAP protein will typically be achieved by operably linking, for example, the DNA or cDNA to a promoter (which is either constitutive or regulatable), followed by incorporation into an expression vector. The vectors can be suitable for replication and integration in either prokaryotes or eukaryotes. Typical expression vectors contain transcription and translation terminators, initiation sequences, and promoters useful for regulation of the expression of the DNA encoding a protein. To obtain high level expression of a cloned gene, it is desirable to construct expression vectors which contain, a strong promoter to direct transcription, a ribosome binding site for translational initiation, and a transcription/translation terminator. One of skill in the art would recognize that modifications can be made to an D-AKAP2 protein without diminishing its biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids (e.g., poly His) placed on either terminus to create conveniently located purification sequences. Restriction sites or termination codons can also be introduced. There are expression vectors that specifically allow the expression of functional proteins. One such vector, Plasmid 577, described in U.S. Pat. No. 6,020,122 and incorporated herein by reference, has been constructed for the expression of secreted antigens in a permanent cell line. This plasmid contains the following DNA segments: (a) a fragment of pBR322 containing bacterial beta-lactamase and origin of DNA replication; (b) a cassette directing expression of a neomycin resistance gene under control of HSV-1 thymidine kinase promoter and poly-A addition signals; (c) a cassette directing expression of a dihydrofolate reductase gene under the control of a SV-40 promoter and poly-A addition signals; (d) cassette directing expression of a rabbit immunoglobulin heavy chain signal sequence fused to a modified hepatitis C virus (HCV) E2 protein under the control of the Simian Virus 40 T-Ag promoter and transcription enhancer, the hepatitis B virus surface antigen (HBsAg) enhancer I followed by a fragment of Herpes Simplex Virus-1 (HSV-1) genome providing poly-A addition signals; and (e) a fragment of Simian Virus 40 genome late region of no function in this plasmid. All of the segments of the vector were assembled by standard methods known to those skilled in the art of molecular biology. Plasmids for the expression of secreted AKAP proteins can be constructed by replacing the hepatitis C virus E2 protein coding sequence in plasmid 577 with a AKAP sequence of SEQ ID NO:63 or a fragment thereof. The resulting plasmid is transfected into CHO/dhfr-cells (DXB-111) (Uriacio et al. (1980) *PNAS*, 77:4451-4466); these cells are available from the A.T.C.C., 12301 Parklawn Drive, Rockville, Md. 20852, under Accession No. CRL 9096), using the cationic liposome-mediated procedure (P. L. Feigner et al. (1987) *PNAS* 84:7413-7417. Proteins are secreted into the cell culture media.

Incorporation of cloned DNA into a suitable expression vector, transfection of cells with a plasmid vector or a combination of plasmid vectors, each encoding one or more distinct proteins, or with linear DNA, and selection of transfected cells are well known in the art (see, e.g., Sambrook et al. (1989) *Molecular Cloning: A Laboratory Manual*, Second Edition, Cold Spring Harbor Laboratory Press). Heterologous nucleic acid may be introduced into host cells by any method known to those of skill in the art, such as transfection with a vector encoding the heterologous nucleic acid by calcium phosphate precipitation (see, e.g., Wigler et al. (1979) *Proc. Natl. Acad. Sci. USA,* 76:1373-1376) or lipofectamine (GIBCO BRL #18324-012). Recombinant cells can then be cultured under conditions whereby the polymorphic human D-AKAP2 protein encoded by the nucleic acid is expressed. Suitable host cells include mammalian cells (e.g., HEK293, including but are not limited to, those described in U.S. Pat. No. 5,024,939 to Gorman (see, also, Stillman et al. (1985) *Mol. Cell. Biol.,* 5:2051-2060); also, HEK293 cells available from ATCC under accession #CRL 1573, CHO, COS, BHKBI and Ltk$^-$ cells, mouse monocyte macrophage P388D1 and J774A-1 cells (available from ATCC, Rockville, Md.) and others known to those of skill in this art), yeast cells, including, but are not limited to, *Pichia pastoris, Saccharomyces cerevisiae, Candida tropicalis, Hansenula polymorpha,* human cells, bacterial cells, including, but are not limited to, *Escherichia coli,* and insect cells. Xenopus oocytes may also be used for expression of in vitro RNA transcripts of the DNA.

Heterologous nucleic acid may be stably incorporated into cells or may be transiently expressed using methods known in the art. Stably transfected mammalian cells may be prepared by transfecting cells with an expression vector having a selectable marker gene (such as, for example, the gene for thymidine kinase, dihydrofolate reductase, neomycin resistance, and the like), and growing the transfected cells under conditions selective for cells expressing the marker gene. To prepare transient transfectants, mammalian cells are transfected with a reporter gene (such as the *E. coli* β-galactosidase gene) to monitor transfection efficiency. Selectable marker genes are not included in the transient transfections because the transfectants are typically not grown under selective conditions, and are usually analyzed within a few days after transfection.

Heterologous nucleic acid may be maintained in the cell as an episomal element or may be integrated into chromosomal DNA of the cell. The resulting recombinant cells may then be cultured or subcultured (or passaged, in the case of mammalian cells) from such a culture or a subculture thereof. Methods for transfection, injection and culturing recombinant cells are known to the skilled artisan. Similarly, the polymorphic human D-AKAP2 proteins or fragments thereof may be purified using protein purification methods known to those of skill in the art. For example, antibodies or other ligands that specifically bind to the proteins may be used for affinity purification and immunoprecipitation of the proteins.

3. Protein Purification

The D-AKAP2 proteins may be purified by standard techniques well known to those of skill in the art. Recombinantly produced proteins can be directly expressed or expressed as a fusion protein. The recombinant protein is purified by a combination of cell lysis (e.g., sonication, French press) and affinity chromatography. The proteins, recombinant or synthetic, may be purified to substantial purity by standard techniques well known in the art, including detergent solubilization, selective precipitation with such substances as ammonium sulfate, column chromatography, immunopurification methods, and others. (See, for example, R. Scopes, *Protein Purification: Principles and Practice,* Springer-Verlag: New York (1982); Deutscher, *Guide to Protein Purification,* Academic Press (1990)). For example, antibodies may be raised to the proteins as described herein. Purification from *E. coli* can be achieved following procedures described in U.S. Pat. No. 4,511,503. The protein may then be isolated from cells expressing the protein and further purified by standard protein chemistry techniques as described herein. Detection of the expressed protein is achieved by methods known in the art and include, for example, radioimmunoassays, Western blotting techniques or immunoprecipitation.

I. Immunodetection of Variant D-AKAP2 Protein Species.

Generally, the variant regions of the variant AKAP protein species provided herein, when presented as an immunogen, should elicit production of a specifically reactive antibody. Immunoassays for determining binding are well known to those of skill in the art, as are methods of making and assaying for antibody binding specificity/affinity. Exemplary immunoassay formats include ELISA, competitive immunoassays, radioimmunoassays, Western blots, indirect immunofluorescent assays, in vivo expression or immunization protocols with purified protein preparations. In general, the detection of immunocomplex formation is well known in the art and may be achieved by methods generally based upon the detection of a label or marker, such as any of the radioactive, fluorescent, biological or enzymatic tags. Labels are well known to those skilled in the art (see U.S. Pat. Nos. 3,817,837; 3,850,752; 3,939,350; 3,996,345; 4,277,437; 4,275,149 and 4,366,241, each incorporated herein by reference). Of course, one may find additional advantages through the use of a secondary binding ligand such as a second antibody or a biotin/avidin ligand binding arrangement, as is known in the art.

1. Production of Polyclonal Antisera Against Specific Variant AKAPs

Antibodies can be raised to the variant AKAP protein species provided herein, including fragments thereof, both in their naturally occurring (full-length) forms and in recombinant forms. Additionally, antibodies are raised to these proteins in either their native configurations or in non-native configurations. Anti-idiotypic antibodies can also be generated. A variety of analytic methods are available to generate a hydrophilicity profile of proteins. Such methods can be used to guide the artisan in the selection of peptides for use in the generation or selection of antibodies which are specifically reactive, under immunogenic conditions. See, e.g., J. Janin, (1979) *Nature,* 277:491-492; Wolfenden et al. (1981) *Biochemistry* 20:849-855; Kyte and Doolite (1982) *J. Mol. Biol.,* 157:105-132; Rose et al. (1985) *Science,* 229:834-838.

A number of immunogens can be used to produce antibodies specifically reactive with a particular variant AKAP protein species. Isolated recombinant, synthetic, or native polypeptides are the preferred immunogens (antigen) for the production of monoclonal or polyclonal antibodies. Polypeptides are typically denatured, and optionally reduced, prior to formation of antibodies for screening expression libraries or other assays in which a putative AKAP protein is expressed or denatured in a non-native secondary, tertiary, or quarternary structure.

The particular variant region of the variant AKAP protein is injected into an animal capable of producing antibodies. Either monoclonal or polyclonal antibodies can be generated for subsequent use in immunoassays to measure the presence and quantity of the protein. Methods of producing polyclonal antibodies are known to those of skill in the art. In brief, an immunogen (antigen), preferably a purified protein, a protein coupled to an appropriate carrier (e.g., GST, keyhole limpet hemanocyanin, etc.), or a protein incorporated into an immunization vector such as a recombinant vaccinia virus (see, U.S. Pat. No. 4,722,848) is mixed with an adjuvant and animals are immunized with the mixture. The animal's immune response to the immunogen preparation is monitored by taking test bleeds and determining the titer of reactivity to the protein of interest. When appropriately high titers of antibody to the immunogen are obtained, blood is collected from the animal and antisera are prepared. Further fractionation of the antisera to enrich for antibodies reactive to the protein is performed where desired (See, e.g., Coligan, *Current Protocols in Immunology*, Wiley/Greene, NY (1991); and Harlow and Lane, *Antibodies: A Laboratory Manual*, Cold Spring Harbor Press, NY (1989)).

2. Western Blotting of Tissue Samples for the Variant D-AKAP2 Protein

Biological samples are homogenized in SDS-PAGE sample buffer (50 mM Tris-HCl, pH 6.8, 100 mM dithiothreitol, 2% SDS, 0.1% bromophenol blue, 10% glycerol), heated at 100° C. for 10 min and run on a 14% SDS-PAGE with a 25 mM Tris-HCl, pH 8.3, 250 mM Glycine, 0.1% SDS running buffer. The proteins are electrophoretically transferred to nitrocellulose in a transfer buffer containing 39 mM glycine, 48 mM Tris-HCl, pH 8.3, 0.037% SDS, 20% methanol. The nitrocellulose is dried at room temperature for 60 min and then blocked with a phosphate-buffered saline (PBS) solution containing either bovine serum albumin or 5% nonfat dried milk for 2 hours at 4° C.

The filter is placed in a heat-sealable plastic bag containing a solution of 5% nonfat dried milk in PBS with a 1:100 to 1:2000 dilution of affinity purified anti-AKAP peptide antibodies, incubated at 4° C. for 2 hours, followed by three 10 min washes in PBS. An alkaline phosphatase conjugated secondary antibody (i.e., anti-mouse/rabbit IgG), is added at a 1:200 to 1:2000 dilution to the filter in a 150 mM NaCl, 50 mM Tris-HCl, pH 7.5 buffer and incubated for 1 h at room temperature.

The bands are visualized upon the addition and development of a chromogenic substrate such as 5-bromo-4-chloro-3-indolyl phosphate/nitro blue tetrazolium (BCIP/NBT). The filter is incubated in the solution at room temperature until the bands develop to the desired intensity. Molecular mass determination is made based upon the mobility of pre-stained molecular weight standards (Rainbow Markers, Amersham, Arlington Heights, Ill.).

3. Microparticle Enzyme Immunoassay (MEIA)

Variant D-AKAP2 protein species and peptides are detected using a standard commercialized antigen competition EIA assay or polyclonal antibody sandwich EIA assay on the lMx.RTM Analyzer (Abbott Laboratories, Abbott Park, Ill.). Samples containing the D-AKAP2 protein are incubated in the presence of anti-D-AKAP2 coated microparticles. The microparticles are washed and secondary polyclonal anti-D-AKAP2 antibodies conjugated with detectable entities (i.e., alkaline phosphatase) are added and incubated with the microparticles. The microparticles are washed and the bound antibody/antigen/antibody complexes are detected by adding a substrate (i.e., 4-methyl umbelliferyl phosphate) (MUP) that will react with the secondary conjugated antibody to generate a detectable signal.

4. Immunocytochemistry

Intracellular localization of the variant D-AKAP2 protein species can be determined by a variety of in situ hybridization techniques. In one method, cells are fixed with fixed in 4% paraformaldehyde in 0.1 M PBS; pH7.4 for 5 min., rinsed in PBS for 2 min., dilapidated and dehydrated in an ethanol series (50, 70 and 95%) (5 min. each and stored in 95% ethanol at 4° C.).

The cells are stained with the primary anti-D-AKAP2 antibody and a mixture of secondary antibodies used for detection. Laser-scanning confocal microscopy is performed to localize the D-AKAP2 protein.

J. Biological Assays

Assays to measure the interaction between the variant D-AKAP2 protein species and variant peptides provided herein and the regulatory subunits RI and/or RII of the Protein Kinase A holoenzyme include immobilized binding assays, solution binding assays and the like. In some instances, it may be desirable to monitor binding between the variant D-AKAP2 protein species and variant peptides, and PKA. In other instances, it may be desirable to specifically monitor the binding between the variant D-AKAP2 protein species and variant peptides, and a cellular component (other than PKA) to which it binds. Assays may be performed in a variety of formats, including cell-based assays, such as di-hybrid screening or complementation assays as described in U.S. Pat. No. 5,283,173 and Patent Cooperation Treaty (PCT) Publication No. WO91/16457, respectively. Assays of this type are particularly useful for assessing intracellular efficacy of test compounds. Non-cell-based assays include scintillation proximity assays, cAMP competition assays, ELISA assays, radioimmunoassays, chemiluminescent assays, and the like. Such assay procedures are well known in the art and generally described, e.g., in Boudet et al. (1991) *J. Immunol. Meth.*, 142:73-82; Ngai et al. (1993) *J. Immunol. Meth.*, 158: 267-276; Pruslin et al. (1991) *J. Immunol. Meth.*, 137:27-35; Udenfriend et al. (1985) *Proc. Natl. Acad. Sci. USA*, 82:8672-8676; Udenfriend et al. (1987) *Anal. Biochem.*, 161:494-500; Bosworth and Towers, (1989) *Nature*, 341:167-168; Gilman, (1970) *Proc. Natl. Acad. Sci. USA*, 67:305-312; and U.S. Pat. No. 4,568,649.

1. In Vitro Binding Assay

Huang et al. (1997) *Proc. Natl. Acad. Sci. USA*, 272:8057-8064; Protein preparations containing D-AKAP2 fused to GST are incubated with glutathione resin in PBS for 2 hours at 4° C. with 0.1% Triton X-100, 1 mM phenylmethylsulfonyl fluoride, 1 mM EDTA, 5 mM benzamidine, and 5 mM β-mercaptoethanol and washed extensively with the same buffer. 200 micrograms of PKA regulatory subunit RII and/or RI were added to the resin and incubated at 4° C. Proteins associated with the D-AKAP2 are eluted and analyzed by Laemmli electrophoresis. The proteins were visualized by Coomassie Staining. PKA proteins can be radiolabeled or labeled with a fluorophore to allow detection; or can be assayed for phosphorylation activity as set forth in the next section.

2. PKA Phosphorylation of Protein Substrate

Cyclic AMP-dependent protein kinase (PKA) catalyzes the transfer of gamma phosphate from adenosine triphosphate (ATP) to a serine or threonine residue in a protein substrate. A short synthetic peptide (Leucine-Arg-Arg-Alanine-Serine-Leucine-Glycine or LRRASLG) is used as a substrate to assay the specific type of PKA activity as described in Pearson et al. (1991) *Meth. Enzymol.*, 200:62-81.

The PKA assay is typically carried out in a reaction of the enzyme with a peptide substrate and gamma $^{32}$P-ATP followed by separation of the $^{32}$P-peptide product from the unreacted gamma $^{32}$P-ATP on a phosphocellulose membrane. This method requires at least one basic amino acid residue in the peptide substrate. The peptide substrate can be tagged with a biotin group so that the biotinylated $^{32}$P-peptide product consistently binds to a streptavidin membrane in a manner independent of the peptide sequence as described in Goueli et al. (1995) *Anal. Biochem.*, 225:10-17. The separation of the $^{32}$P-peptide product from the free gamma $^{32}$P-ATP using affinity binding and ultrafiltration separation to analyze a mixture of samples as described in U.S. Pat. No. 5,869,275.

K. Screening Assays for Modulators

Modulators of D-AKAP2 biological activities may be identified by using any of the disclosed methods related to D-AKAP2 binding to PKA, D-AKAP2 localization in the mitochondria, binding to other signaling enzymes and phosphorylation by PKA. D-AKAP2 proteins are involved in signal transduction as they bind to protein kinase A (PKA) and are thought to anchor the kinase at a location, e.g., the mitochondria, where PKA acts to phosphorylate a specific substrate, either at the mitochondria or at an ion channel. Thus, an alteration in D-AKAP2 binding to PKA, localization to the mitochondria, or phosphorylation by PKA, among other steps, will result in an alteration in signal transduction.

Accordingly, provided herein are methods of screening for agents that decrease or disrupt the binding of a Val(646) variant of D-AKAP2 with RIα PKA, comprising combining a candidate agent with a cell comprising a nucleotide sequence which encodes a Val(646) variant D-AKAP protein corresponding to SEQ ID NO:65, operably linked to a promoter such that the nucleotide sequence is expressed as a D-AKAP2 protein in the cell; and determining the effect of the agent upon the localization of PKA to the mitochondria, wherein a decrease in localization to the mitochondria identifies an agent that decreases the binding of a Val(646) variant of D-AKAP2 with RIα PKA. Also provided are high-throughput methods of screening for agents that decrease (or disrupt) the binding of a Val(646) variant of D-AKAP2 to an RIα subunit of PKA, comprising combining a candidate agent with an admixture comprising RIα and a D-AKAP2 peptide sequence that binds to RIα; and determining the effect of the agent upon the localization of PKA to a mitochondria. The candidate agent can be combined with the admixture in a cell-free system. The candidate agent is combined with the admixture intracellularly. The peptide sequence can be any of the D-AKAP2 peptides described herein.

In particular, once a variant D-AKAP2 proteins species or variant D-AKAP peptide provided herein is contacted with a potential modulating molecule, the effect of the molecule on the binding between AKAP protein or peptide and PKA can be determined using the assays disclosed herein. For example, mitochondria can be isolated from cells exposed to the potential modulating molecule. PKA protein can then be isolated and quantitated or phosphorylation can be determined using the disclosed PKA assay. An increase in the amount of PKA protein in the mitochondria or the quantity of test peptide phosphorylated by mitochondrial isolated PKA would indicate a positive effect of the test molecule. Binding of the particular variant D-AKAP2 protein species, or peptide fragment thereof, and PKA could be directly assessed using an in vitro binding assay, or other disclosed binding assays such as set forth in Example 3 herein, or by immunoassays such as immunoprecipitation.

L. Assay Formats and Selection of Test Substances That Modulate at Least one D-AKAP2-mediated Activity of a PKA Holoenzyme Methods for identifying agents that modulate at least one D-AKAP2-mediated activity of a PKA holoenzyme are provided. The methods include phage display and other methods for assessing alterations in the activity of a D-AKAP2 protein and/or a PKA holoenzyme. Such methods or assays can use any means of monitoring or detecting the desired activity. A variety of formats and detection protocols are known for performing screening assays. Any such formats and protocols can be adapted for identifying modulators of D-AKAP2-mediated PKA holoenzyme activities. The following includes a discussion of exemplary protocols.

1. High Throughput Screening Assays

Although the above-described assay can be conducted where a single D-AKAP2 protein or peptide and/or PKA holoenzyme is screened, and/or a single test substance is screened in one assay, the assay typically is conducted in a high throughput screening mode, i.e., a plurality of the PKA holoenzymes are screened against and/or a plurality of the test substances are screened simultaneously (See, generally, *High Throughput Screening: The Discovery of Bioactive Substances* (Devlin, Ed.) Marcel Dekker, 1997; Sittampalam et al. (1997) *Curr. Opin. Chem. Biol.*, 1:384-91; and Silverman et al. (1998) *Curr. Opin. Chem. Biol.*, 2:397-403). For example, the assay can be conducted in a multi-well (e.g., 24-, 48-, 96-, 384-, 1536-well or higher density), chip or array format.

High-throughput screening (HTS) is the process of testing a large number of diverse chemical structures against disease targets to identify "hits" (Sittampalam et al. (1997) *Curr. Opin. Chem. Biol.*, 1:384-391). Current state-of-the-art HTS operations are highly automated and computerized to handle sample preparation, assay procedures and the subsequent processing of large volumes of data.

Detection technologies employed in high-throughput screens depend on the type of biochemical pathway being investigated (Sittampalam et al. (1997) *Curr. Opin. Chem. Biol*, 1:384-391). These methods include, radiochemical methods, such as the scintillation proximity assays (SPA), which can be adapted to a variety of enzyme assays (Lerner et al. (1996) *J. Biomol. Screening*, 1:1 35-143; Baker et al. (1996) *Anal. Biochem.*, 239:20-24; Baum et al. (1996) *Anal. Biochem.*, 237:129-134; and Sullivan et al. (1997) *J. Biomol. Screening*, 2:19-23) and protein-protein interaction assays (Braunwalder et al. (1996) *J. Biomol. Screening*, 1:23-26); Sonatore et al. (1996) *Anal. Biochem.* 240:289-297; and Chen et al. (1996) *J. Biol. Chem.*, 271:25308-25315), and non-isotopic detection methods, including but are not limited to, calorimetric and luminescence detection methods, resonance energy transfer (RET) methods, time-resolved fluorescence (HTRF) methods, cell-based fluorescence assays, such as fluorescence resonance energy transfer (FRET) procedures (see, e.g., Gonzalez et al. (1995) *Biophys. J.*, 69:1272-1280), fluorescence polarization or anisotropy methods (see, e.g., Jameson et al. (1995) *Methods Enzymol.*, 246:283-300; Jolley, (1996) *J. Biomol. Screening*, 1:33-38; Lynch et al. (1997) *Anal. Biochem.* 247:77-82), fluorescence correlation spectroscopy (FCS) and other such methods.

2. Test Substances

Test compounds, including small molecules, antibodies, proteins, nucleic acids, peptides, and libraries and collections thereof, can be screened in the above-described assays and assays described below to identify compounds that modulate the D-AKAP2-mediated activity of a PKA holoenzyme. Rational drug design methodologies that rely on computational chemistry can be used to screen and identify candidate compounds.

The compounds identified by the screening methods include inhibitors, such antagonists, and can be agonists. Compounds for screening include any compounds and collections of compounds available, known or that can be prepared.

a. Selection of Compounds

Compounds can be selected for their potency and selectivity of modulating either the phosphorylation activity of a PKA holoenzyme or the translocation (e.g., localization to mitochondria) of the PKA holoenzyme. As described herein, and as generally known, a variant D-AKAP2 protein species, or peptide fragment thereof (e.g., SEQ ID NOs:17-54, and the like), a target PKA holoenzyme and its substrate are combined under assay conditions permitting reaction of the enzyme with its substrate. The assay is performed in the absence of test compound, and in the presence of increasing concentrations of the test compound. In addition, to identify test compounds that modulate D-AKAP2 mediated PKA activity, these assays can be performed in the absence of D-AKAP2, or fragments thereof. Those of skill in the art will understand that if a test compound demonstrates modulating activity of PKA in the presence of D-AKAP2, or fragments therof, and not in its absence, then that compound is identified and selected as a D-AKAP2 mediated modulator of PKA activity. The concentration of test compound at which 50% of the enzymatic activity (e.g., phosphorylation activity) is inhibited by the test compound is the $IC_{50}$ value (Inhibitory Concentration) or $EC_{50}$ (Effective Concentration) value for that compound. Within a series or group of test compounds, those having lower $IC_{50}$ or $EC_{50}$ values are considered more potent inhibitors of the PKA enzymatic activity than those compounds having higher $IC_{50}$ or $EC_{50}$ values. The $IC_{50}$ measurement is often used for more simplistic assays, whereas the $EC_{50}$ is often used for more complicated assays, such as those employing cells.

Typically candidate compounds have an $IC_{50}$ value of 100 nM or less as measured in an in vitro assay for inhibition of PKA holoenzyme activity. The test compounds also are evaluated for selectivity toward a particular isoform of PKA, such as an RIα or and RIIα containing PKA. As described herein, and as generally known, a test compound is assayed for its potency toward a panel of variant D-AKAP2 protein species, or peptide fragments thereof (e.g., SEQ ID NOs:17-54, and the like) and/or a target PKA holoenzyme, and other enzymes and an $IC_{50}$ value or $EC_{50}$ value is determined for each test compound in each assay system. A compound that demonstrates a low $IC_{50}$ value or $EC_{50}$ value for the target enzyme, e.g., PKA holoenzyme, and a higher $IC_{50}$ value or $EC_{50}$ value for other enzymes within the test panel (e.g., urokinase tissue plasminogen activator, thrombin, Factor Xa), is considered to be selective toward the target enzyme. Generally, a compound is deemed selective if its $IC_{50}$ value or $EC_{50}$ value in the target enzyme assay is at least one order of magnitude less than the next smallest $IC_{50}$ value or $EC_{50}$ value measured in the selectivity panel of enzymes.

Compounds are also evaluated for their activity in vivo. The type of assay chosen for evaluation of test compounds depends on the pathological condition to be treated or prevented by use of the compound, as well as the route of administration to be evaluated for the test compound.

The following examples are included for illustrative purposes only and are not intended to limit the scope of the invention. The practice of methods and development of the products provided herein employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, *Molecular Cloning A Laboratory Manual*, 2nd Ed., ed. by Sambrook, Fritsch and Maniatis (Cold Spring Harbor Laboratory Press: 1989); *DNA Cloning*, Volumes I and II (D. N. Glover, ed., 1985); *Oligonucleotide Synthesis* (M. J. Gait, ed., 1984); Mullis et al., U.S. Pat. No. 4,683,195; *Nucleic Acid Hybridization* (B. D. Hames & S. J. Higgins, eds., 1984); *Transcription and Translation* (B. D. Hames & S. J. Higgins, eds., 1984); *Culture of Animal Cells* (R. I. Freshney, Alan R. Liss, Inc., 1987); *Immobilized Cells and Enzymes* (IRL Press, 1986); B. Perbal, *A Practical Guide To Molecular Cloning* (1984); the treatise, *Methods In Enzymology* (Academic Press, Inc., New York); *Gene Transfer Vectors For Mammalian Cells* (J. H. Miller and M. P. Calos, eds., 1987, Cold Spring Harbor Laboratory); *Methods In Enzymology*, Vols. 154 and 155 (Wu et al., eds.); *Immunochemical Methods In Cell and Molecular Biology* (Mayer and Walker, eds., Academic Press, London, 1987); *Handbook of Experimental Immunology*, Volumes I-IV (D. M. Weir and C. C. Blackwell, eds., 1986); *Manipulating the Mouse Embryo*, (Cold Spring Harbor Laboratory Press, Cold Spring Harbor, N.Y., 1986).

EXAMPLE 1

Assay of the Binding of D-AKAP2, A-Kinase Binding (AKB) Domain Ile/Val Variants to PKA The variable amino acid (Ile/Val) is located at amino acid 646 of SEQ ID NOs:64 and 65 in the AKB domain of D-AKAP2. This domain is the docking site for PKA and is highly conserved among species. Similar to other AKAPs, the AKB domain forms an amphipathic helix with hydrophobic amino acids on one face of the helix. To determine whether the D-AKAP2 Ile/Val variation resulted in an alteration in its binding properties to PKA, the binding of each variant to the regulatory subunit of PKA was investigated.

Binding of each AKB domain variant to PKA was first examined using an in vitro pull-down assay, in which the 40 C-terminal residues of D-AKAP2 (amino acids 623-662 of SEQ ID NO:64) containing the AKB were fused to glutathione-S-transferase (GST). The GST fusion constructs were made by fusing the 40 C-terminal amino acids of D-AKAP2 to the C-terminus of GST and subcloning between the NdeI and BamHI sites of pRSET (Invitrogen, Carlsbad, Calif.). The constructs were transfected into BL21 cells and expressed for 6 hours at 20° C. The cells were lysed in PBS with 5 mM BME and 0.1% Triton X-100. 3 µl of supernatant were added to 200 µl of this buffer and 10 µl glutathione beads. After three washes, RIα (53 µg, 20 µM) and RIIα (2.4 µg, 2 µM) were added to the beads, respectively, and the total volume was adjusted to 40 µl. After incubating for 30 min at 4° C., the beads were washed three times, and separated in a 10% acrylamide gel.

The Ile/Val substitution resulted in an isoform specific difference in PKA binding. The RIα isoform of PKA bound with a significantly higher affinity to the Val variant. The higher affinity was seen for both the mouse and the human AKB domains. The residue differences between mouse and human downstream of the Ile/Val position had no effect on the binding properties. Moreover, there was no difference in binding of the variants to the RIIα isoform.

EXAMPLE 2

Assay of the Binding Affinity of Each Ile/Val AKB Domain Variant to PKA R-subunit Isoforms To assess the magnitude of the affinity difference, binding of both Ile/Val variants to the R-subunit isoforms of PKA was analyzed in a quantitative assay. Twenty-seven residue peptides containing the two AKB domain Ile/Val variants (SEQ ID NOs:1 and 2, respectively) of D-AKAP2 with a C-terminal cysteine were synthesized by SynPep Corporation (Dublin, Calif.). The peptides were HPLC (high performance liquid chromatography) purified and mass spectrometry checked. Both peptides were labeled with tetramethyl rhodamine-5-maleiamide (Molecular Probes, Eugene, Oreg.) at the cysteine residue and HPLC purified. Increasing concentrations of RIα and RIIβ, respectively, were equilibrated with 10 nM of peptide for at least one hour at room temperature in 10 mM HEPES, 150 mM NaCl, 3 mM EDTA, 0.005% polysorbate 20. For RIIα tests, 1 nM of labeled peptide was used since the binding affinity to RIIα was higher than to RIα and RIIβ. Fluorescence anisotropy was monitored using a Fluoromax-2 (Spex, JobinYvon Horiba, Edison, N.J.) equipped with polarizers. The fluorophore was excited at 541 nm (5-10 nm bandpass) and emission was monitored at 575 nm (5-10 nm bandpass). For each protein three separate binding experiments were averaged and fit to a 1:1 binding model using the non-linear regression application in GraphPad Prism version 3.00 (GraphPad Software, San Diego, Calif.).

Peptides of each AKB Ile/Val variant (SEQ ID NOs:1 and 2) were synthesized and fluorescence-labeled. Binding of the labeled peptides to the regulatory subunit isoforms was monitored using a fluorescence assay in which binding of the peptide was proportional to an increase in steady state anisotropy. There was no difference in binding of the AKB variants to either the RIIα or RIIβ isoforms. In addition, the RII isoforms bound tighter to the variants than the R1α isoform. However, as indicted by the pull-down experiments, R1α displayed differential binding to the AKB variants. The Val variant (SEQ ID NO:2) had a nearly three-fold increase in binding affinity when compared to the Ile variant (SEQ ID NO:1). The interaction was specific since no binding was observed to a deletion construct of RIα that lacked the AKAP binding domain (delta 1-91 RIα).

EXAMPLE 3

In vivo Assays of the Association of the AKB Ile646Val Variants and the PKA Regulatory Subunits and Targeting to Mitochondria To determine whether the observed in vitro affinity differences resulted in a difference in cellular compartmentalization, the association of the AKB Ile/Val variants and the PKA regulatory subunits in vivo was examined. The 30 amino acid mitochondrial anchoring domain of D-AKAP1 (Chen et al. (1997) *J. Biol. Chem.*, 272:15247-57; and Huang et al. (1997) *J. Biol. Chem.*, 272:8057-8064) was fused to the C-terminal 156 residues of mouse (amino acids 217-372 of SEQ ID NO:55) and human (amino acids 507-662 of SEQ ID NO:64) D-AKAP2, respectively, followed by a Flag-tag and subcloned into pcDNA4 (Invitrogen, Carlsbad, Calif.). The dimerization/docking (D/D) domain of RIα and full-length RIIα were each fused with green fluorescent protein (GFP) and cloned into pEGFPN1 (Clontech, Palo Alto, Calif.). Equal molar ratios of the Flag-tagged D-AKAP2 constructs and either RIIα-GFP or RIα-D/D-GFP constructs were mixed and transfected into 10T(1/2) cells using cytofectene (BioRad, Hercules, Calif.). The AKB domain was detected by immuno-staining with monoclonal antibodies against the Flag-tag (Kodak, Rochester, N.Y.) followed by rhodamine-conjugated secondary antibody (Jackson Lab, Bar Harbor, Me.). The cells were imaged using a Zeiss microscope equipped with a digital camera. Each channel was exposed for the same amount of time.

In this assay, the AKB domain within the C-terminal 156 residues of D-AKAP2 from mouse (Val) and human (Ile) was fused to the mitochondrial anchoring domain from D-AKAP1 and tethered to the outer mitochondrial membrane (Chen et al. (1997) *J. Biol. Chem.*, 272:15247-15257; and Huang et al. (1997) *J. Biol. Chem.*, 272:8057-8064). The binding of the AKB domain with the PKA regulatory domains was detected as the co-transfected PKA regulatory domains co-localized to the mitochondria. Both the human and mouse AKB domains can target RIIα to the mitochondria effectively, in accordance with their similar affinity in vitro. However, for R1α there was a difference in co-localization between the variants. The Val variant effectively targeted RIα to the mitochondria. The Ile variant, however, was unable to target RIα, which was evenly diffused in the cytosol suggesting that the Ile variant of D-AKAP2 may have impaired ability to sequester RIα.

The D-AKAP2 variants at amino acid 646 of SEQ ID NOs:64 and 65 described herein map to the conserved AKB domain of D-AKAP2, which was previously shown to interact with the regulatory subunit of PKA. In accordance with the methods provided herein, it has been demonstrated that this variation impacts the binding to PKA in an isoform specific manner both in vitro and in vivo. The Val(646) variant at amino acid 646 of SEQ ID NO:65, which has previously been identified as a deleterious allele associated with morbidity in the age-stratified approach (see, e.g., U.S. patent application No. US20020040130A1 and PCT WO 02/04489), binds three-fold tighter to the RIα isoform when compared to the Ile(646) variant. At the cellular level, this affinity difference resulted in a decrease in mitochondrial localization of the Ile (646) variant.

EXAMPLE 4

Development of a Detection System to Verify Binding of 27-mer Peptides to PKA Homodimers A peptide SPOT-synthesis technique was applied to study the interaction of a 27-mer D-AKAP2-derived peptide VQGNTDEAQEELAWKIAKMIVSDIMQQ (SEQ ID NO:1) with the regulatory subunit PKA-RIIα. However, prior to binding studies on cellulose membranes, the interaction of the 27-mer with PKA was confirmed by ELISA (enzyme-linked immunosorbent assay).

a) ELISA Assays

The peptide biotin-bA-bA-VQGNTDEAQEELAWKI-AKMIVSDIMQQ (SEQ ID NO:14) was synthesized as a C-terminal amide in milligram quantity and purified to a 96% purity by HPLC. Its identity was confirmed by MALDI TOF (matrix-assisted laser desorption ionization time-of-flight) mass spectrometry. The peptide was immobilized in neutravidin (NA)-coated 96-well microtiter plates and incubated with various concentrations of PKA-RIIα-GFP. Binding was detected using an anti-GFP antibody (3E6, Quantum Biotechnologies, QBiogene, Carlsbad, Calif.) in combination with a second horseradish peroxidase labeled antibody. Microtiterplates were coated with 40 μg/ml Neutravidin (NA) and subsequently incubated with 25 μM peptide. Various concentrations (0-5 μg/ml) of PKA-RIIα-GFP were added. Bound subunit was detected using a mouse anti-GFP antibody (1 μg/ml) and an anti-mouse-IgG-antibody labeled with peroxidase (1 μg/ml). Negative controls were utilized that contained either a microtiter plate with only neutravidine or only peptide, or neither one. The only signal detected was in wells containing both neutravidin and peptide, indicating that the 27-mer peptide corresponding to SEQ ID NO:1, when immobilized on Neutravidin coated wells, is able to bind to PKA-RIIα in the same experiment.

EXAMPLE 5

Assay of Binding Properties of the 27-mer Peptide Dependent Upon Amino Acid Sequence Composition and Length a) Identification of critical residues for binding PKA within the 27-mer peptide (SEQ ID NO:1) corresponding to the binding domain of D-AKAP2.

To identify key residues within the 27-mer Ile/Val peptides (SEQ ID NO:1) for interaction with PKA, an alanine, an aspartic acid, and a lysine scan was performed. The filters for the peptide arrays were prepared by SPOT-synthesis and incubated with PKA-RIIα-GFP (see, e.g., Frank R., (1992) Tetrahedron, 48(42):9217-9232; Kramer et al. (1994) Comp. Meth. Enzymol., 6:388-395; Kramer et al. (1997) Meth. Mol. Biol., 87:25-39; and Kramer et al. (1999) J. Peptide Res., 54:319-327). Binding was detected using an anti-GFP antibody (3E6, Quantum Biotechnologies, QBiogene, Carlsbad, Calif.) in combination with a secondary antibody and a chemiluminescence-imager. All scans revealed a clear key residue pattern.

Residues of the 27-mer peptide that cannot be substituted for while retaining the ability to bind RIIα: in the Ala-scan are residues 16, 20 and 21; in the Asp-scan are residues 12, 13, 16, 17, 20, 21 and 24; in the Lys-scan are residues 12, 13, 16, 17, 20, 21, and 24 of the 27-mer peptide (SEQ ID NO:1). Residues that result in reduced binding upon substitution in the Ala-scan are residues 10, 12, and 23; in the Asp-scan are residues 14 and 15; and in the Lys-scan is residue 14 of the 27-mer peptide (SEQ ID NO:1). These results indicate a helical structure of the binding domain. Although the variable position (Ile/Val) occurs at amino acid residue 24, in this experiment only isoleucine containing peptides were synthesized.

b) Amino- and Carboxy-terminal truncation experiments to identify minimal peptide length capable of binding to PKA-RIα and PKA-RIIα.

Several truncation analogs of the 27-mer peptide corresponding to SEQ ID NO:1 have been synthesized and tested for binding. N-terminal truncations, C-terminal truncations, and N/C-terminal truncations were performed. For example, Table 3 sets forth N/C-terminal truncations where, sequentially, both an N- and a C-terminal amino acid were omitted in each SPOT-synthesis.

TABLE 3

| PEPTIDES | Relative ability to bind to: RIa | RIIa | SEQ ID NO: |
|---|---|---|---|
| VQGNTDEAQEELAWKIAKMIVSDIMQQ | +++ | +++ | SEQ ID NO:1 |
| QGNTDEAQEELAWKIAKMIVSDIMQ | +++ | +++ | SEQ ID NO:5 |
| GNTDEAQEELAWKIAKMIVSDIM | +++ | +++ | SEQ ID NO:6 |
| NTDEAQEELAWKIAKMIVSDI | +++ | +++ | SEQ ID NOs:3 and 7 |
| TDEAQEELAWKIAKMIVSD | – | ++ | SEQ ID NO:8 |
| DEAQEELAWKIAKMIVS | – | ++ | SEQ ID NO:9 |
| EAQEELAWKIAKMIV | – | + | SEQ ID NO:4 |

TABLE 3-continued

| PEPTIDES | Relative ability to bind to: RIa | RIIa | SEQ ID NO: |
|---|---|---|---|
| AQEELAWKIAKMI | – | – | SEQ ID NO:10 |
| QEELAWKIAKM | – | – | SEQ ID NO:11 |
| EELAWKIAK | – | – | SEQ ID NO:12 |
| ELAWKIA | – | – | SEQ ID NO:13 |

In this experiment, only the isoleucine variant 27-mer peptide (SEQ ID NO:1) was used (amino acid position of variation corresponds to position 24 of SEQ ID NO:1). Incubation with PKA-RIα-GFP and PKA-RIIα-GFP and detection with antibodies was performed as described above. It has been found that several residues from the N- and C-terminus can be omitted without significant loss of binding. The shortest peptide with no reduced signal intensity identified for both RIα and RIIα is a 21-mer with the following sequence:

(SEQ ID NOs:3 and 7)
NH2-NTDEAQEELAWKIAKMIVSDI-COOH.

It is important to note that the Ile/Val polymorphic amino acid position corresponding to the last residue in the above peptide SEQ ID NOs:3 and 7 (or residue 24 in SEQ ID NO:1) is essential for binding to the RIα subunit. If the peptide is truncated to exclude residue 24 in SEQ ID NO:1, the remaining peptide does not bind to RIα at all. In addition, if the peptide is truncated to exclude residue 24 in SEQ ID NO:1, binding to RIIα is reduced. In this particular N/C-terminal dual truncation assay, it has been found that the shortest peptide that still binds to RIIα is a 15-mer: NH2-EAQEELAWKIAKMIV-COOH (SEQ ID NO:4).

In addition, the minimal sequence required for regulatory subunit binding was also assessed using N- and C-terminal truncations of the 27-residue human D-AKAP2 sequence. N-terminal or C-terminal truncated peptides were synthesized using SPOT synthesis on cellulose membrane as described herein. Binding was evaluated by incubating each membrane with GFP-RIα D/D and GFP-RIIα D/D as indicated below. The dimerization/docking (D/D) domain of bovine RIα (residues 1-109) and mouse RIIα (residues 1-46), fused to green fluorescence protein (GFP) were subcloned into a pRSET expression vector (Invitrogen, Carlsbad, Calif.) downstream of a histidine tag. The proteins, GFP-RIα D/D and GFP-RIIα D/D were expressed in E. coli BL21 (DE3) and purified using Talon (Clontech, Palo Alto, Calif.) resin. The His tag was cleaved using thrombin and the protein further purified using an S75-Sephadex (16/60) gel filtration column (Pharmacia, Peapack, N.J.) in 50 mM MES pH 5.8, 50 mM NaCl, 2 mM EDTA, 2 mM EGTA, 2 mM DTT. The protein was stored at 4° C.

Bound protein was detected using a primary antibody against GFP and enzyme conjugated secondary antibody for amplification of signal. The membrane was then analyzed by chemiluminescence. The results are set forth in Tables 4 and 5.

TABLE 4

| PEPTIDES | Relative ability to bind to: RIIα | RIα | SEQ ID NO: |
|---|---|---|---|
| VQGNTDEAQEELAWKIAKMIVSDIMQQ | +++ | +++ | SEQ ID NO:1 |
| QGNTDEAQEELAWKIAKMIVSDIMQQ | +++ | +++ | SEQ ID NO:66 |
| GNTDEAQEELAWKIAKMIVSDIMQQ | +++ | +++ | SEQ ID NO:67 |
| NTDEAQEELAWKIAKMIVSDIMQQ | +++ | +++ | SEQ ID NO:68 |
| TDEAQEELAWKIAKMIVSDIMQQ | +++ | +++ | SEQ ID NO:69 |
| DEAQEELAWKIAKMIVSDIMQQ | +++ | +++ | SEQ ID NO:70 |
| EAQEELAWKIAKMIVSDIMQQ | ++ | +++ | SEQ ID NO:71 |
| AQEELAWKIAKMIVSDIMQQ | ++ | +++ | SEQ ID NO:72 |
| QEELAWKIAKMIVSDIMQQ | ++ | +++ | SEQ ID NO:73 |
| EELAWKIAKMIVSDIMQQ | ++ | ++ | SEQ ID NO:74 |
| ELAWKIAKMIVSDIMQQ | ++ | + | SEQ ID NO:75 |
| LAWKIAKMIVSDIMQQ | + | − | SEQ ID NO:76 |
| AWKIAKMIVSDIMQQ | + | − | SEQ ID NO:77 |
| WKIAKMIVSDIMQQ | − | − | SEQ ID NO:78 |
| KIAKMIVSDIMQQ | − | − | SEQ ID NO:79 |
| IAKMIVSDIMQQ | − | − | SEQ ID NO:80 |
| AKMIVSDIMQQ | − | − | SEQ ID NO:81 |
| KMIVSDIMQQ | − | − | SEQ ID NO:82 |

TABLE 5

| PEPTIDES | Relative ability to bind to: RIIα | RIα | SEQ ID NO: |
|---|---|---|---|
| VQGNTDEAQEELAWKIAKMIVSDIMQQ | +++ | +++ | SEQ ID NO:1 |
| VQGNTDEAQEELAWKIAKMIVSDIMQ | +++ | +++ | SEQ ID NO:83 |
| VQGNTDEAQEELAWKIAKMIVSDIM | +++ | +++ | SEQ ID NO:84 |
| VQGNTDEAQEELAWKIAKMIVSDI | +++ | +++ | SEQ ID NO:85 |
| VQGNTDEAQEELAWKIAKMIVSD | +++ | − | SEQ ID NO:86 |
| VQGNTDEAQEELAWKIAKMIVS | ++ | − | SEQ ID NO:87 |
| VQGNTDEAQEELAWKIAKMIV | ++ | − | SEQ ID NO:88 |
| VQGNTDEAQEELAWKIAKMI | − | − | SEQ ID NO:89 |
| VQGNTDEAQEELAWKIAKM | − | − | SEQ ID NO:90 |
| VQGNTDEAQEELAWKIAK | − | − | SEQ ID NO:91 |
| VQGNTDEAQEELAWKIA | − | − | SEQ ID NO:92 |
| VQGNTDEAQEELAWKI | − | − | SEQ ID NO:93 |
| VQGNTDEAQEELAWK | − | − | SEQ ID NO:94 |
| VQGNTDEAQEELAW | − | − | SEQ ID NO:95 |
| VQGNTDEAQEELA | − | − | SEQ ID NO:96 |
| VQGNTDEAQEEL | − | − | SEQ ID NO:97 |
| VQGNTDEAQEE | − | − | SEQ ID NO:98 |
| VQGNTDEAQE | − | − | SEQ ID NO:99 |

The C-terminal truncations defined clearly the C-terminal boundary for binding to the isoforms. There was an absence of binding to both regulatory subunits at a defined residue from the C-terminus. For RIα, binding abruptly stopped after the C-terminal isoleucine (VQGNTDEAQEELAWKIAKMIVSDI; SEQ ID NO:85), suggesting that the C-terminal ( . . . MQQ) residues are not required for binding (Table 5). This C-terminal isoleucine residue is the location of a single nucleotide polymorphism of D-AKAP2, which codes for either a valine or isoleucine at this position (I646V; SEQ ID NOs:64 and 65). For RIIα, binding abruptly stopped at the upstream valine position (VQGNTDEAQEELAWKIAKMIV; SEQ ID NO:88), suggesting that more C-terminal residues ( . . . SDIMQQ; SEQ ID NO:1, amino acids 22-27), which contain the polymorphism, are dispensable for the RIIα binding site (Table 5). This is consistent with the I646V polymorphic site only having an effect on binding to the RIα isoform.

The N-terminal truncations did not result in a clear-cut boundary, but rather there was a titratable decrease in signal for both RIα and RIIα isoforms starting at the glutamine (QEELAWKIAKMIVSDIMQQ; SEQ ID NO:73) (Table 4). This suggests that the N-terminal negative charges play a role in enhancing the affinity to both isoforms.

EXAMPLE 6

Assay of the Binding Properties of the two Naturally Occurring Allelic Variants of the D-AKAP2 Protein a) Optimization of peptide density and regeneration protocols.

First, the optimal peptide density for further synthesis was determined to improve quantification of binding differences between both PKA isoforms. This was achieved by synthesizing two sets of membranes containing two peptide sequences representing the Ile and Val alleles, respectively:

VQGNTDEAQEELAWKIAKMIVSD<u>I</u>MQQ    (SEQ ID NO:1)

VQGNTDEAQEELAWKIAKMIVSD<u>V</u>MQQ    (SEQ ID NO:2)

Both peptides were synthesized as 5 spots varying in peptide density from 50% to 0.1% membrane saturation. Then, set 1 was incubated with PKA-RIα-GFP, set 2 with PKA-RIIα-GFP to determine the optimal peptide density for the binding assay. Subsequently, the membranes were regenerated and incubated with the other regulatory subunit, respectively (set 1 with PKA-RIIα-GFP, set 2 with PKA-RIα-GFP). This was to verify the feasibility of regenerating the membranes, which was beneficial for the following experiments as well as to identify the preferred order of incubation.

Membranes after incubation and GFP-signal development, as well as quantification of the signal intensities revealed that the signal intensity for PKA-RIα-GFP decreases with reduction of the peptide density, whereas the highest signals for PKA-RIIα-GFP are observed for reduced peptide densities between 5 and 10%. These findings correlate with a higher affinity of the peptides for PKA-RIIα-GFP. A reduced peptide density of 10% suitable for both regulatory subunits was suggested for further experiments.

For PKA-RIIα-GFP, an approximate 10-fold higher signal intensity compared to PKA-RIα-GFP was measured. Since both membranes were incubated simultaneously under the same conditions this finding must be due to the higher affinity of PKA-RIIα-GFP for the D-AKAP2-derived peptide. No significant PKA-RIIα-GFP binding differences between the Ile and Val variants of the D-AKAP2-derived peptide were observed. However, allele-specific differences were obtained for PKA-RIα-GFP.

After stripping and regeneration of membranes similar results were obtained compared to a fresh filter set. The signal intensity was about 10% lower. However, the regeneration protocol is suitable since no signals were observed in a control experiment with the detection antibodies alone. The preferred order for further experiments was determined to be incubation of peptide membranes with PKA-RIα-GFP followed by PKA-RIIα-GFP due to the differences in signal intensity.

b) Quantification of allele-specific binding differences.

Two 27-mer peptides representing the Ile and Val variants (SEQ ID NOs:1 and 2, respectively) were synthesized and purified in milligram quantities and the affinity to PKA-RIα-GFP was determined using well-known surface plasmon resonance in combination with BIAcore chips (see, e.g., *Current Opinion in Biotechnology* (1997) 8:50-57; *Current Opinion in Biotechnology* (1994) 5:389-395; *Current Opinion in Biotechnology* (1994) 5:65-71; *Structure* (1995) 3:969; *Current Biology* (1995) pp. 699-705; *Analytical Biochemistry* (1991) 201:197-210; and macinfac.bio.unc.edu/biacore.html). PKA-RIα-GFP was coupled to BIAcore CM5 chips. BSA was immobilized on control chips.

| Chip 1: | PKA-RIa-GFP (1681 RU) | Chip 2: | BSA (1424 RU) |
|---|---|---|---| cell with the regulatory subunit and the control protein BSA was measured, such that slight unspecific binding to BSA directly reduces the apparent affinity. However, similar to previous results, an affinity difference of PKA-RIα-GFP to both allelic 27-mer peptides was observed (Table 6).

EXAMPLE 7

Identification of Substituted Peptide Sequences That are Able to Disrupt the Interaction Between D-AKAP2 and PKA Completely by Either Binding Specifically PKA-RIα- or -RIIα or by Binding Both PKA Isoforms Substitution analysis of both allelic peptides (VQGNTDEAQEELAWKIAKMIVSDVMQQ; SEQ ID NO:2 and VQGNTDEAQEELAWKIAKMIVSDIMQQ; SEQ ID NO:1) was conducted. Each amino acid of the 27-mer peptide was substituted, one amino acid at a time per peptide, by any naturally occurring L- and D- amino acid. For both peptides complete L- and D- substitution analysis membranes have been screened for binding of PKA-RIα-GFP. After regeneration, the peptide arrays were incubated with PKA-RIIα-GFP. After binding, detection was carried out with an anti-GFP antibody in combination with a peroxidase-labeled secondary antibody.

a) Peptide Array Synthesis

The cellulose-bound peptide libraries were automatically prepared according to standard SPOT synthesis protocols (Frank, R., (1992) *Tetrahedron*, 48:9217-9232) using a SPOT synthesizer (Abimed GmbH, Langenfeld, Germany) as described in Kramer et al. (1998) *Methods Mol. Biol.*, 87:25-39 and Wenschuh et al. (2000) *Biopolymers*, 55:188-206. The peptides were synthesized on an amino functionalized cellulose membrane as distinct spots. A β-alanine dipeptide spacer was inserted between the C-terminus of the peptide and the membrane support. The peptide loading of the membranes was reduced by mixing 10% Fmoc-β-alanine-OPfp and 90% acetylated β-alanine-OPfp active esters for the first coupling step. This peptide loading was optimized in advance by varying the Fmoc-β-alanine-OPfp percentage from 0.1% to 50%. The peptide was extended stepwise using standard Fmoc solid-phase peptide synthesis followed by cleavage of the side chain protecting groups under trifluoroacetic acid (TFA) conditions. Sequence files were generated with the software DIGEN (Jerini AG, Berlin, Germany). All peptides were N-terminally acetylated. For synthesis quality control, a selection of peptides that was synthesized in duplicate was

TABLE 6

PKA-RIα-GFP binding affinity

| | PKA-RIα-GFP | |
|---|---|---|
| Ac-VQGNTDEAQEELAWKIAKMIVSD$\underline{V}$MQQ-NH$_2$ | $5.0 \times 10^{-7}$ | SEQ ID NO:15 |
| Ac-VQGNTDEAQEELAWKIAKMIVSD$\underline{I}$MQQ-NH$_2$ | $8.6 \times 10^{-7}$ | SEQ ID NO:16 |

The affinities in this assay are lower compared to those determined by fluorescence anisotropy. The most likely reason is that in this study the signal difference between the flow cleaved from the solid support by ammonia vapor in the dry state. Subsequently, identity was verified by MALDI-MS (Voyager-DE, Applied Biosystems, Foster City, Calif., USA).

b) Peptide Array Screening

The peptide arrays were pre-incubated with T-TBS blocking buffer (TBS pH 8.0, 0.05% Tween 20 in the presence of blocking reagent; Roche Diagnostics Chemiluminescence detection kit 1500694, Mannheim, Germany). Subsequently, the peptide arrays were incubated with solutions of GFP-RIα D/D or GFP-RIIα D/D at a final concentration of 1.0 µg/ml for 2 h in T-TBS blocking buffer. After washing three times for 10 min with T-TBS, the anti-GFP antibody 3E6 (Quantum Biotechnologies, QBiogene, Carlsbad, Calif.) was added to a final concentration of 1 µg/ml in T-TBS blocking buffer for 1 h followed by washing three times for 10 min with T-TBS. Finally, the arrays were incubated with a second anti-mouse IgG peroxidase-labeled antibody (Catalog #: A5906, Sigma, Deisenhofen, Germany) which was applied at a concentration of 1 µg/ml in T-TBS blocking buffer for 1 h, followed by washing three times for 10 min with T-TBS. Analysis and quantification of peptide-bound GFP-RIα D/D- or GFP-RIIα D/D-antibody complexes was done using a chemiluminescence substrate and the Lumi-Imager® (Roche Diagnostics, Mannheim, Germany). All steps were carried out at room temperature. Binding of the detection antibodies to the peptides was excluded by control incubations with antibody 3E6 and the anti-mouse IgG peroxidase-labeled antibody alone. For a given membrane, binding of GFP-RIα D/D was performed first. Subsequently, the membrane was regenerated using detergent (Kramer et al. (1998) *Methods Mol. Biol.,* 87:25-39) and complete removal of the GFP-RIα D/D was proven by a control incubation with antibody 3E6 and the anti-mouse IgG peroxidase-labeled antibody alone. Afterwards, binding of GFP-RII D/D to the peptide array was assessed.

The results of the incubated membranes containing the single amino acid substitutions using L-amino acids are shown in FIG. 1. FIG. 1 shows the amino acid substitution analysis of both isoforms (V/I24; SEQ ID NOs:1 and 2: of a 27-mer D-AKAP2 peptide that is the binding domain for the RIα and RIIα subunits of protein kinase A (PKA). Each amino acid of the respective D-AKAP2 peptide (vertical lane) was substituted, one amino acid at a time, by a single L-amino acid (horizontal line). The top filters show the results of substituting amino acid residues in the Valine variant (SEQ ID NO:2; and the bottom filters represent the substitutions in the Isoleucine variant (SEQ ID NO:1). The left hand filters were analyzed with PKA-RIα-GFP and right hand filters with PKA-RIIa-GFP, respectively. Key amino acid residues for the binding to both RIα and RIIα are indicated to be residues 12, 13, 16, 17, 20 and 21. The vertical dark boxes occurring at residues 10-21 of the V/I24 peptides in the proline column indicate loss of binding to both isoforms after proline substitution in the middle part of the peptide. The light colored boxes mark substitutions specifically disrupting or significantly decreasing the binding to PKA-RIα-GFP. Substitutions that significantly enhance the binding of both V/I24 peptides to PKA-RIα-GFP are dark-circled and correspond to the substitution in SEQ ID NOs:1 and 2 of one, two or more: of Q at residue 9 with F, I, L, V, H, M, R, T, W or Y; of L at residue 12 with F, W or Y; of V at residue 21 with I, L or W; and of M at residue 25 with F, I, L, T, V, W or Y. For light-colored boxes and circled markings, the binding to PKA-RIIα-GFP can be either increased, normal, decreased or even completely disrupted.

Key residues for binding of D-AKAP2 peptide variants to PKA-RIα-GFP and PKA-RIIα-GFP are I16, A17, I20, and V21. For binding to both PKA-GFP subunits (RIα and RIIα) these critical residues cannot be substituted on the peptide without loss of binding except by physicochemically very similar ones, which will lead to reduced binding (e.g., A17 by I or V). The substitution pattern reflects the postulated helical binding structure of the peptide. Key residues are found on one side of the helical wheel and proline substitutions in the central part of the peptide corresponding to residues 10-21 are disadvantageous for the binding to both isoforms of PKA.

In this substitution analysis only slight differences between the valine and isoleucine variants were observed. However, it was not the objective to compare both allelic peptides quantitatively.

D-amino acid substitutions in the central part of the peptide reduce the binding ability to both PKA subunits. The binding to PKA-RIIα-GFP was regularly decreased throughout the entire peptide for all substitutions. There were a few substitutions, which enhanced the binding to PKA-RIα-GFP in the context of all other substitutions. The following list indicates those peptides and substitutions with D-amino acid analogs in underlined and bold one-letter code.

```
VQGNTTEAQEELAWKIAKMIVSD[I/V]MQQ;     (SEQ ID NO:17)

VQGNTDEAFEELAWKIAKMIVSD[I/V]MQQ;     (SEQ ID NO:18)

VQGNTDEAIEELAWKIAKMIVSD[I/V]MQQ;     (SEQ ID NO:19)

VQGNTDEALEELAWKIAKMIVSD[I/V]MQQ;     (SEQ ID NO:20)

VQGNTDEAVEELAWKIAKMIVSD[I/V]MQQ;     (SEQ ID NO:21)

VQGNTDEAWEELAWKIAKMIVSD[I/V]MQQ;     (SEQ ID NO:22)

VQGNTDEAYEELAWKIAKMIVSD[I/V]MQQ;     (SEQ ID NO:23)

VQGNTDEAQEELAWKIAKMILSD[I/V]MQQ;     (SEQ ID NO:24)

VQGNTDEAQEELAWKIAKMIVLD[I/V]MQQ;     (SEQ ID NO:25)
and

VQGNTDEAQEELAWKIAKMIVSD[I/V]FQQ.     (SEQ ID NO:26)
```

EXAMPLE 8

Identification of Peptide Sequences That Show Preferential and/or Enhanced Binding to Either PKA-RIα or -RIIα

As a result of the substitution analysis conducted as described in Example 7 and set forth in FIG. 1, it has been found that amino acid residues L12 and A13 are key residues for PKA-RIα binding but not for PKA-RIIα binding, which indicates that binding of the 27-mer peptides to PKA-RIα-GFP is more entailed compared to PKA-RIIα-GFP. Also residues D23 and V/I24 (corresponding to the polymorphic position within the 27-mer peptides), are residues with a limited preference for certain amino acids regarding the binding to PKA-RIα-GFP.

Exemplary substitution analogs leading to preferred or exclusive binding of the 27-mer peptides to PKA-RIα-GFP relative to PKA-RIIα-GFP; or enhanced binding to both RIα and RIIα isoforms correspond to the substitution in SEQ ID NOs:1 and/or 2 of one, two or more: of Q at residue 9 with F, I, L, V, H, M, R, T, W or Y; of L at residue 12 with F, W or Y; of V at residue 21 with I, L or W; and of M at residue 25 with F, I, L, T, V, W or Y.

For the 27-mer Val-isoform (SEQ ID NO:2), exemplary substitution analogs leading to preferred or exclusive binding to PKA-RIIα-GFP relative to PKA-RIα-GFP correspond to the substitution in SEQ ID NO:2: of L at residue 12 with A, C, or K; of A at residue 13 with F, H, I, K, L, M or N; of W at residue 14 with C; of K at residue 15 with C; of K at residue 18 with C; of M at residue 19 with C; of S at residue 22 with C; and of D at residue 23 with C.

For the 27-mer Ile-isoform (SEQ ID NO:1), exemplary substitution analogs leading to a preferred or exclusive binding to PKA-RIIα-GFP relative to PKA-RIα-GFP correspond to the substitution in SEQ ID NO:1; of A at residue 13 with F, H, I, L, M and S; of W at residue 14 with C; of K at residue 15 with C; of K at residue 18 with C; of M at residue 19 with C; of S at residue 22 with C; and of D at residue 23 with C.

The following is an exemplary list of peptides substituted with L- and D-amino acid residues bearing specific novel binding properties. Since the design of these experiments was not done to disclose binding differences between the two allelic peptides (SEQ ID NOs:1 and 2), both peptide syntheses can be used as mutual replications. Peptides that show similar binding properties in two independent experiments are indicated below.

A. Peptides with substantially no binding to PKA-RIα-GFP but normal binding to PKA-RIIα-GFP. Substituted L-amino acids are indicated in bold, and the polymorphic site in brackets:

```
VQGNTDEAQEELFWKIAKMIVSD[I/V]MQQ;    (SEQ ID NO:27)

VQGNTDEAQEELIWKIAKMIVSD[I/V]MQQ;    (SEQ ID NO:28)

VQGNTDEAQEELLWKIAKMIVSD[I/V]MQQ;    (SEQ ID NO:29)

VQGNTDEAQEELAWCIAKMIVSD[I/V]MQQ;    (SEQ ID NO:30)

VQGNTDEAQEELAWKIACMIVSD[I/V]MQQ;    (SEQ ID NO:31)

VQGNTDEAQEELAWKIAKCIVSD[I/V]MQQ;    (SEQ ID NO:32)
and

VQGNTDEAQEELAWKIAKMIVCD[I/V]MQQ.    (SEQ ID NO:33)
```

B. Peptides with substantially no binding to PKA-RIα-GFP and reduced binding to PKA-RIIα-GFP. Substituted L-amino acids are indicated in bold, and the polymorphic site in brackets:

```
VQGNTDEAQEECAWKIAKMIVSD[I/V]MQQ;    (SEQ ID NO:34)

VQGNTDEAQEEKAWKIAKMIVSD[I/V]MQQ;    (SEQ ID NO:35)

VQGNTDEAQEELHWKIAKMIVSD[I/V]MQQ;    (SEQ ID NO:36)

VQGNTDEAQEELKWKIAKMIVSD[I/V]MQQ;    (SEQ ID NO:37)

VQGNTDEAQEELMWKIAKMIVSD[I/V]MQQ;    (SEQ ID NO:38)

VQGNTDEAQEELNWKIAKMIVSD[I/V]MQQ;    (SEQ ID NO:39)

VQGNTDEAQEELVWKIAKMIVSD[I/V]MQQ;    (SEQ ID NO:40)

VQGNTDEAQEELWWKIAKMIVSD[I/V]MQQ;    (SEQ ID NO:41)

VQGNTDEAQEELYWKIAKMIVSD[I/V]MQQ;    (SEQ ID NO:42)
and

VQGNTDEAQEELAWKIAKMIVSC[I/V]MQQ.    (SEQ ID NO:43)
```

C) Peptides with enhanced binding to both, PKA-RIα-GFP and PKA RIIα-GFP. Substituted L-amino acids are indicated in bold, and the polymorphic site in brackets:

```
VQGNTDEAFEELAWKIAKMIVSD[I/V]MQQ;    (SEQ ID NO:44)

VQGNTDEAIEELAWKIAKMIVSD[I/V]MQQ;    (SEQ ID NO:45)

VQGNTDEALEELAWKIAKMIVSD[I/V]MQQ;    (SEQ ID NO:46)

VQGNTDEAVEELAWKIAKMIVSD[I/V]MQQ;    (SEQ ID NO:47)

VQGNTDEAQEELAWKIAKMIVSD[I/V]FQQ;    (SEQ ID NO:48)

VQGNTDEAQEELAWKIAKMIVSD[I/V]IQQ;    (SEQ ID NO:49)
and

VQGNTDEAQEELAWKIAKMIVSD[I/V]LQQ.    (SEQ ID NO:50)
```

D. Peptides with enhanced binding to PKA-RIα-GFP but normal or reduced binding to PKA-RIIα-GFP. Substituted L-amino acids are indicated in bold, and the polymorphic site in brackets:

```
VQGNTDEAQEEFAWKIAKMIVSD[I/V]MQQ;    (SEQ ID NO:51)

VQGNTDEAQEELAWKIAKMIISD[I/V]MQQ;    (SEQ ID NO:52)
and

VQGNTDEAQEELAWKIAKMILSD[I/V]MQQ.    (SEQ ID NO:53)
```

E. Peptide with binding to PKA-RIα-GFP but substantially no binding to PKA-RIIα-GFP. Substituted L-amino acids are indicated in bold, and the polymorphic site in brackets:

```
VQGNTDEAQEELAWKIAKMIWSD[I/V]MQQ    (SEQ ID NO:54)
```

F. Peptides with enhanced binding to PKA-RIα-GFP but reduced binding to PKA-RIIα-GFP. Substituted D-amino acids are indicated in bold and underlined, and the polymorphic site in brackets:

VQGNTEAQEELAWKIAKMIVSD[I/V]MQQ; (SEQ ID NO:17)

VQGNTDEAFEELAWKIAKMIVSD[I/V]MQQ; (SEQ ID NO:18)

VQGNTDEAIEELAWKIAKMIVSD[I/V]MQQ; (SEQ ID NO:19)

VQGNTDEALEELAWKIAKMIVSD[I/V]MQQ; (SEQ ID NO:20)

VQGNTDEAVEELAWKIAKMIVSD[I/V]MQQ; (SEQ ID NO:21)

VQGNTDEAWEELAWKIAKMIVSD[I/V]MQQ; (SEQ ID NO:22)

VQGNTDEAYEELAWKIAKMIVSD[I/V]MQQ; (SEQ ID NO:23)

VQGNTDEAQEELAWKIAKMILSD[I/V]MQQ; (SEQ ID NO:24)

VQGNTDEAQEELAWKIAKMIVLD[I/V]MQQ; and (SEQ ID NO:25)

VQGNTDEAQEELAWKIAKMIVSD[I/V]FQQ. (SEQ ID NO:26)

EXAMPLE 9

In vivo Assays of the Association of AKB Variants and the PKA Regulatory Subunits and Targeting to Mitochondria In addition to defining the helical motif critical for binding, the peptide array revealed several key substitutions along the helix that either enhanced binding to RIα relative to RIIα or disrupted binding to RIα while maintaining RIIα binding (see Examples 7 and 8). For example, valine at position 21, when substituted with a tryptophan abolished binding to RIIα but maintained affinity for RIα. In contrast, a single substitution at position 13, abolished binding to only the RIα isoform. Several other substitutions at positions 9, 12, 21 and 25 seemed to enhance binding to RIα, while reducing binding to RIIα.

Figure 2:
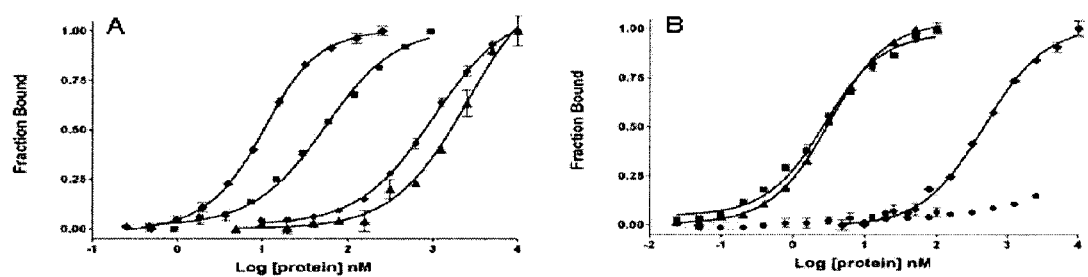
FIGS. 2A and 2B show the binding of AKB (dual) (■), AKB (RI) [Q9F, V21W, M25F] (♦), AKB (RII) [A13L] (▲) and AKB (null) (●) peptides to full-length RIα (A) and RIIα (B). Each peptide was fluorescently labeled and incubated with the corresponding regulatory subunit for 1 hour in 10 mM Hepes, 150 mM NaCl, 3 mM EDTA pH 7.4. Fluorescence anisotropy was used to monitor bound peptide.

Using these isoform-selective positions as guides, several peptides were synthesized with the desired selectivity by using single or multiple substitutions and their activity tested in a quantitative fluorescence binding assay (FIG. 2).

a) Peptide Synthesis and Fluorescence Labeling

The wild type D-AKAP2 peptide referred to herein as "AKB(dual)" (VQGNTDEAQEELAWKIAKMIVSD-VMQQ; SEQ ID NO:2) for the in-solution peptide binding assays was synthesized by SynPep (Dublin, Calif.). The following peptides were synthesized by Anaspec (San Jose, Calif.):

```
                     (SEQ ID NO:29; "AKB(RII)")
VQGNTDEAQEELLWKIAKMIVSDVMQQ (SEQ ID NO:100; "AKB(nuII)")
VQGNTDEAQEELAWKIEKMIWSDVMQQ (SEQ ID NO:101)
VQGNTDEAQEELAWKIAKMIWSDVMQQ (SEQ ID NO:102)
Ac-DLAWKIAKMIVSDVMQQ
```

Additional multiple substitution peptides (PV-37, 38, 47, 48, 49) were synthesized by Peptron (Korea). All peptides contained a C-terminal Cys for conjugation of the fluorescence probe and contained an amide protected C-terminus. The peptides were HPLC purified and the molecular mass verified by mass spectrometry. Peptide purities were greater than 95%.

Each peptide was fluorescently labeled using a 25 mM solution of tetramethylrhodamine-5-maleimide (catalog number T-6027; Molecular Probes, Eugene, Oreg.) dissolved in DMSO. The peptides were labeled by incubating with a three-fold molar excess of the label for 16 hr at 4° C. in 20 mM Tris, pH 7.0 and 1 mM tris-(2-carboxyethyl) phosphine, hydrochloride (TCEP) (non-thiol reducing agent, Molecular Probes). The sample was quenched with 1 mM, β-mercaptoethanol to bind to any unreacted maleimide and diluted with 0.1% TFA for purification by HPLC. The labeled peptides were resolved using a C18 column with a water/acetonitrile gradient containing 0.1% TFA. The concentration of each peptide was determined by absorbance at 541 nm after diluting into 100% methanol and using an extinction coefficient of 91,000 $M^{-1}$ $cm^{-1}$ for absorbance of the rhodamine label at 541 nm (Molecular Probes Catalog). The peptides were stored at 4° C. in 50% acetonitrile.

b) RIα and RIIα Production

Full-length murine RIIα was expressed in *E. coli* BL21 (DE3). Full-length bovine RIα was expressed in *E. coli* 222. The proteins were purified as previously described using a cAMP affinity resin (Hamuro et al. (2002) *J. Mol. Biol.*, 321:703). The protein concentrations were determined using the following extinction coefficients at 280 nm, which were calculated using a standard concentration of protein calibrated using quantitative amino acid analysis: RIα 52,603 $M^{-1}$ $cm^{-1}$ and RIIα 62,456 $M^{-1}$ $cm^{-1}$. The proteins were stored at 4° C. in 50 mM MES pH 5.8, 50 mM NaCl, 2 mM EDTA, 2 mM EGTA, 2 mM DTT.

c) Fluorescence Anisotropy

Binding of each fluorescently labeled peptide to the regulatory subunits was monitored using fluorescence anisotropy. RIα and RIIα were serially diluted beginning at 1 μM and 0.1 μM, respectively, into 10 mM HEPES pH 7.4, 0.15 M NaCl, 3 mM EDTA, 0.005% Surfactant P20 (Biacore) containing either 10 nM or 1 nM of fluorescently labeled peptide for RIα and RIIα, respectively. The samples were equilibrated for at least 1 hour at room temperature and fluorescence anisotropy monitored using a Fluoromax-2 (Jobin Yvon Horiba, SPEX Division, Edison, N.J.) equipped with Glan-Thompson polarizers. The rhodamine-labeled peptide was excited at 541 nm (5-10 nm bandpass) and emission monitored at 575 nm (5-10 nm bandpass). The anisotropy was calculated directly with the Fluoromax software using the following equation:

$$r = (I_{VV} - G \cdot I_{VH})/(I_{VV} + 2G \cdot I_{VH}) \quad (1)$$

where r is the steady state anisotropy, $I_{VV}$ is the fluorescence intensity with the excitation and emission polarizers oriented in the vertical position (0° from normal), $I_{VH}$ is the fluorescence intensity with the excitation polarizer in the vertical position and the emission polarizer oriented in the horizontal position (90°) relative to the excitation polarizer, G is the monochromator grating factor which is equal to $(I_{HV}/I_{HH})$, with the first subscript indicating the position of the excitation polarizer and the second subscript indicating position of the emission polarizer. Three separate binding experiments were averaged and fit to a 1:1 binding model using the non-linear regression application in GraphPad Prism version 3.00 (GraphPad Software, San Diego, Calif.).

TABLE 7

Dissociation constants ($K_D$) with standard error (n = 3) for peptides binding to RIα and RIIα determined using a fluorescence anisotropy binding assay.

| Peptide | RIα (nM) ($K_D$) | RIIα (nM) (KD) |
|---|---|---|
| AKB (dual), WT (SEQ ID NO:108)<br>VQGNTDEAQEELAWKIAKMIVSDVMQQC | 48 ± 4 | 2.2 ± 0.2 |
| AKB (RII), RII specific (SEQ ID NO:109)<br>VQGNTDEAQEELLWKIAKMIVSDVMQQC | 2493 ± 409 | 2.7 ± 0.1 |
| AKB (RI), RI specific (SEQ ID NO:103)<br>FEELAWKIAKMIWSDVFQQC | 5.2 ± 0.5 | 456 ± 33 |
| AKB (null) (SEQ ID NO:110)<br>VQGNTDEAQEELAWKIEKMIWSDVMQQC | 998 ± 66 | > 10,000 |

Substituted residues are underlined and in bold.

The binding affinities of three peptides designated RIIα-specific (A13L; SEQ ID NO:109), RIα-specific (Q9F, V21W, and M25F; SEQ ID NO:103) and null (A17E and V21W; SEQ ID NO:110) were compared with the unsubstituted peptide (FIG. 2 and Table 7) using fluorescence anisotropy. The results shown in Table 7 and FIG. 2 indicate that the A13L substitution did not affect binding to RIIα, but dramatically affected binding to RIα, establishing this peptide as an RIIα-specific peptide, AKB(RII) (Table 7). The triple substituted RIα-specific peptide not only resulted in a considerable reduction in affinity to RIIα, but also enhanced binding to RIα by a factor of ten (Table 7). The null peptide bound very poorly to RIα and binding to RIIα could not be detected (FIG. 2).

c) Assay of Truncated and Substituted Peptides

Several additional truncated and substituted peptides were synthesized and their affinity to RIα and RIIα evaluated using fluorescence anisotropy (see Table 8). Binding was evaluated for both RIα and RIIα0 using fluorescence anisotropy as described herein. Substituted residues are in bold in Table 8.

Tryptophan at a position corresponding to residue 21 of SEQ ID NO:2 is important for discriminating against binding to the RIIα subunit. PV-38 (SEQ ID NO:103) is designated an RI-specific binding peptide because it exhibits enhanced binding to RIα and substantially no binding (e.g., very weak binding) to RIIα compared to unmodified SEQ ID NO:108, AKB (RI), and is indicated with an asterisk.

TABLE 8

|  |  | $K_D$ (nM) | |
| --- | --- | --- | --- |
|  |  | RIα | RIIα |
| SEQ ID NO:108 (residues 9-28) | . . . QEELAWKIAKMIVSDVMQQC | 48 ± 4 | 2.2 ± 0.2 |
| SEQ ID NO:111 (residues 9-28) | . . . QEELAWKIAKMIWSDVMQQC | 120 ± 13 | 83 ± 7 |
| SEQ ID NO:112 | Ac-DLAWKIAKMIVSDVMQQC | 773 ± 49 | 107 ± 5 |
| PV-37 | FEELAWKIAKMIWSDVMQQC | 19 ± 0.7 | 150 ± 11 |
| *PV-38 | FEELAWKIAKMIWSDVFQQC | 5.2 ± 0.5 | 456 ± 33 |
| PV-47 | QEEFAWKIAKMIVSDVFQQC | 39 ± 3 | 89 ± 5 |
| PV-48 | QEEFAWKIAKMIISDVFQQC | 12 ± 2 | 124 ± 12 |
| PV-49 | FEELAWKIAKMIISDVFQQC | 1.1 ± 0.1 | 2.5 ± 0.2 |

PV-37 (SEQ ID NO:104);
PV-38 (SEQ ID NO:103);
PV-47 (SEQ ID NO:105);
PV-48 (SEQ ID NO:106);
PV-49 (SEQ ID NO:107)

To determine whether the N-terminal negative charges were important for high affinity binding as suggested from the truncation data, a truncation peptide corresponding to SEQ ID NO:102 was synthesized that did not contain the two N-terminal Glu residues, but instead contained an N-terminal α-acetylated Asp. This peptide also showed reduced binding to both regulatory subunits confirming the requirement of at least one of the N-terminal negative charges. Also evident from these mutations is the importance of the bulky hydrophobic tryptophan at position 21 in selectively reducing the affinity to the type II isoform. The single mutant V21W (SEQ ID NO:111 showed dramatically reduced binding to RIIα, while only showing modestly decreased affinity toward RIα (Table 8). This position is therefore a critical position along the helix for establishing RI/RII selectivity. In the background of V21W, further substitutions at position 9 and 25 dramatically enhanced binding to RIα while further disrupting RIIα binding (see PV-37 and PV-38, Table 8). RIIα also seemed to be less tolerant of the Leu to Phe substitution at position 12 (PV-47 and PV-48, Table 8). PV-49, which is identical to PV-38 except that it has an Ile instead of a Trp at position 21, bound with the greatest affinity to RIα (Table 8). However, this peptide also bound very tightly to RIIα. This again reinforced that a bulky aromatic residue at position 21 was important to select against RIIα binding. Interestingly, the Phe at positions 9 and 25 are only disruptive to RIIα binding when Trp is present at position 21 (PV-38). When Trp at position 21 is replaced with Ile, the affinity for RIIα is restored and the affinity for RIα further enhanced (PV-49). Thus, it is contemplated herein that Trp at position 21 (i) and the Phe at position 25 (i+4) may interact to form additional unfavorable interactions for RIIα binding.

EXAMPLE 10

In vivo Assays of the Association of AKB Variants and the PKA Regulatory Subunits and Targeting to Mitochondria To test the ability of the mutations set forth in Table 7 [AKB(dual), AKB(RI), AKB(RII) and AKB(null)] to co-localize with selected PKA isoforms in cells, a flag-tagged AKB domain construct targeted to the mitochondria was prepared using the AKB domain and a mitochondria targeting sequence from D-AKAP1 as set forth in Example 3. The respective mutations were then incorporated into the AKB domain of D-AKAP2 to test for selectivity in the cell. The targeting constructs of the AKB domain were made by fusing the C-terminal 156 residues of mouse D-AKAP2 with the N-terminal mitochondrial-targeting domain of D-AKAP1 (residues 1-30 of D-AKAP1a). After adding a flag tag to the C-terminus, the constructs were sub-cloned into the pCI vector (Promega, Madison, Wis.). The mutations of the AKB domain corresponding to those set forth in Table 7 herein were made with the QuickChange mutagenesis method (Makarova et al. (2000) *Biotechniques,* 29:970-972). Full-length bovine RIα and mouse RIIα were fused with green fluorescent protein (GFP) by subcloning into pEGFPN1

(Clontech, Palo Alto, Calif.). Equal amounts of the targeting constructs and either GFP-RIα or GFP-RIIα constructs were co-transfected into 10T(1/2) cells using Lipofectamin (Invitrogen, Carlsbad, Calif.). The AKB domain was detected by immuno-staining with monoclonal antibodies against the Flag-tag (Kodak, Rochester, N.Y.) followed by a rhodamine-conjugated secondary antibody (Jackson Lab, Bar Harbor, Me.). The cells were imaged using a radiance confocal microscope (BioRad, Hercules, Calif.).

By concentrating D-AKAP2 at the mitochondria, the co-localization of the AKB domain and the R isoforms was easily detected. GFP constructs of RIα and RIIα were co-transfected into 10T (1/2) cells with Flag-tagged wild type AKB (dual), AKB(RII), AKB(RI) and AKB(null). The results indicated that all of the AKB domains localized well to the mitochondria. The AKB(dual) was able to recruit both GFP-RIα and GFP-RIIα to the mitochondria. The RII-specific peptide, AKB(RII), recruited RII to the mitochondria but was incapable of recruiting GFP-RI. In contrast, the RI-specific peptide, AKB(RI), only localized GFP-RI to the mitochondria; GFP-RII was not localized by the targeted AKB(RI) peptide. The null peptide, AKB(null), could not co-localize either GFP-RIα or RIIα.

EXAMPLE 11

Construction of Transgenic Knock-in Mice Containing Single Specific Amino Acid Substitutions in D-AKAP2

Constructs to knock-in specific amino acid substitutions in mice are designed as follows, which results in a change in the binding of D-AKAP2 to both PKA isoforms (containing RI or RII subunits) and subsequently the D-AKAP2 mediated function. The mouse D-AKAP2 cDNA sequence has been cloned (see, Huang et al. (1997) *PNAS*, 94:11184-11189) and is available at accession #NM_019921. Although Huang et al., believed the 372 amino acid protein was full-length, it may represent a truncated version of the mouse D-AKAP2 protein. The genomic organization and structure of the mouse D-AKAP2 gene is available in draft form from Genbank (accession #AL646042 and #AC084019). The mouse protein and nucleic acid sequences are set forth in SEQ ID NOs:55 and 56. In SEQ ID NOs:55 and 56, the first amino acid (met) corresponds to amino acid position 291 in the human D-AKAP2 protein set forth as SEQ ID NOs:64 and 65. The PKA binding sequence (27-amino acid peptide) corresponds to amino acids 333-359 of the mouse D-AKAP2 protein SEQ ID NO:56 and to amino acids 623-649 of the human D-AKAP2 protein SEQ ID NOs:64 and 65.

A) Based on the mouse cDNA sequence set forth in SEQ ID NO:55, a modified D-AKAP2 knock-in mouse is created, using well-known methods, by introducing a Q9I substitution in the region of mouse D-AKAP2 corresponding to the 27-mer peptide region set forth in SEQ ID NOs:1 and 2 (which corresponds to a Q341I substitution in the mouse D-AKAP2 protein set forth in SEQ ID NO:56). The knock-in is created by replacing the codon corresponding to nucleotides 1021-1023 of SEQ ID NO:55 with either one of the codons "ATT" or "ATC". The phenotype of this particular Q341I knock-in mouse corresponds to enhanced binding of the modified D-AKAP2 protein to PKA-RIα-GFP, but normal binding to PKA-RIIα-GFP.

B) Based on the mouse cDNA sequence set forth in SEQ ID NO:55, a modified D-AKAP2 knock-in mouse is created, using well-known methods, by introducing an A13L substitution in the region of mouse D-AKAP2 corresponding to the 27-mer peptide region set forth in SEQ ID NOs:1 and 2 (which corresponds to a A345L substitution in the mouse D-AKAP2 protein set forth in SEQ ID NO:56). The knock-in is created by replacing the codon corresponding to nucleotides 1033-1035 of SEQ ID NO:55 with either one of the codons "TTA", "TTG", "CTT", "CTC", "CTA" or "CTG". The phenotype of this particular A345L knock-in mouse corresponds to disrupted binding of the modified D-AKAP2 protein to PKA-RIα-GFP, but normal binding to PKA-RIIα-GFP.

C) Based on the mouse cDNA sequence set forth in SEQ ID NO:55, a modified D-AKAP2 knock-in mouse is created, using well-known methods, by introducing a V21W substitution in the region of mouse D-AKAP2 corresponding to the 27-mer peptide region set forth in SEQ ID NOs:1 and 2 (which corresponds to a V353W substitution in the mouse D-AKAP2 protein set forth in SEQ ID NO:56). The knock-in is created by replacing the codon corresponding to nucleotides 1057-1059 of SEQ ID NO:55 with either one of the codons "TGA" or "TGG". The phenotype of this particular V353W knock-in mouse corresponds to normal binding of the modified D-AKAP2 protein to PKA-RIα-GFP, but disrupted binding to PKA-RIIα-GFP.

EXAMPLE 12

Construction of Transgenic Triple-mutant Knock-in Mice Containing Three Specific Amino Acid Substitutions in D-AKAP2

Based on the mouse cDNA sequence set forth in SEQ ID NO:55, a modified D-AKAP2 knock-in mouse is created, using well-known methods, by introducing a Q9F, V21W, M25F triple-mutant substitution in the region of mouse D-AKAP2 corresponding to the 27-mer peptide region set forth in SEQ ID NOs:1 and 2 (which corresponds to a Q341F, V353W, M357F substitution in the mouse D-AKAP2 protein set forth in SEQ ID NO:56). The knock-in is created by replacing the codon corresponding to nucleotides 1021-1023 (9QF) of SEQ ID NO:55 with either one of the codons "TTT" or "TTC"; by replacing the codon corresponding to nucleotides 1057-1059 of SEQ ID NO:55 with either one of the codons "TGA" or "TGG"; and replacing the codon corresponding to nucleotides 1069-1071 of SEQ ID NO:55 with either one of the codons "TTT" or "TTC". The phenotype of this particular Q341 F, V353W, M357F triple-mutant knock-in mouse corresponds to RIα-specific binding (e.g., corresponding to approximately 10-fold increased binding to RIα and approximately 220-fold decreased binding affinity for RIIα; see Table 7).

Since modifications will be apparent to those of skill in this art, it is intended that this invention be limited only by the scope of the appended claims.

What is claimed:

1. A polypeptide that is a mutein of SEQ ID NO: 2, wherein the mutein exhibits modified binding to a regulatory subunit of PKA compared to SEQ ID NO: 2 and wherein said mutein:
   is a peptide selected from the group consisting of a) a peptide having the sequence SEQ ID NO: 2, b) a peptide having the sequence SEQ ID NO: 2 further comprising a C-terminal cysteine, c) a peptide having the sequence SEQ ID NO: 2 wherein residues 1-8 are deleted, and d) a peptide having the sequence SEQ ID NO: 2 wherein residues 1-8 are deleted further comprising a C-terminal cysteine;
   except that said peptide has an amino acid residue substitution at the residue equivalent to residue 21 of SEQ ID NO: 2 of Trp and/or Ile for Val, or an amino acid residue substitution at the residue equivalent to residue 12 of SEQ ID NO: 2 of Phe for Leu; and
   zero, one, or two amino acid residue substitutions selected from the group consisting of Phe, Ile, Leu, Val, His, Met, Arg, Thr, Trp, or Tyr at the residue equivalent to residue 9 of SEQ ID NO: 2 for Gln; and Phe, Ile, Leu, Thr, Val, Trp, or Tyr at the residue equivalent to residue 25 of SEQ ID NO: 2 for Met.

2. A polypeptide of claim 1, wherein the mutein exhibits modified binding to a regulatory subunit of PKA compared to a peptide having the sequence SEQ ID NO: 2.

3. The polypeptide of claim 1 that exhibits enhanced binding to PKA-RIα subunits.

4. The polypeptide of claim 3 that exhibits normal or reduced binding to PKA-RIIα subunits.

5. The polypeptide of claim 1 that exhibits reduced binding to PKA-RIIα subunits.

6. The polypeptide of claim 5 that exhibits normal or increased binding to PKA-RIα subunits.

7. The peptide of claim 1, wherein the peptide exhibits a preferred or exclusive binding to PKA-RIα subunits relative to PKA-RIIα subunits.

8. A peptide that has enhanced ability to bind to PKA-RIα subunit, and a reduced ability to bind to PKA-RIIα subunit, compared to the peptide of SEQ ID NOs:1 or 2, wherein the peptide is selected from the group consisting of:

```
FEELAWKIAKMIWSDVMQQC;    (SEQ ID NO:104; PV-37)

FEELAWKIAKMIWSDVFQQC;    (SEQ ID NO:103; PV-38)

QEEFAWKIAKMIVSDVFQQC;    (SEQ ID NO:105; PV-47)

QEEFAWKIAKMIISDVFQQC;    (SEQ ID NO:106; PV-48).
```

9. The mutein of claim 1, wherein said mutein comprises an amino acid substitution at residue 21 of Ile or Trp for Val.

10. The mutein of claim 1, wherein said mutein comprises an amino acid substitution at residue 21 of Trp for Val.

11. The mutein of claim 9, wherein said mutein comprises an amino acid substitution at residue 9 of Phe for Gln.

12. The mutein of claim 1, wherein said mutein is a peptide having the sequence SEQ ID NO: 2 wherein amino acids 1-8 are deleted or a peptide having the sequence SEQ ID NO: 2 wherein amino acids 1-8 are deleted further comprising a C-terminal cysteine.

13. The mutein of claim 9, wherein said mutein is a peptide having the sequence SEQ ID NO: 2 wherein amino acids 1-8 are deleted or a peptide having the sequence SEQ ID NO: 2 wherein amino acids 1-8 are deleted further comprising a C-terminal cysteine.

14. The mutein of claim 10, wherein said mutein is a peptide having the sequence SEQ ID NO: 2 wherein amino acids 1-8 are deleted or a peptide having the sequence SEQ ID NO: 2 wherein amino acids 1-8 are deleted further comprising a C-terminal cysteine.

15. A peptide that has an enhanced ability to bind to PKA-RIα subunit, and a reduced ability to bind to PKA-RIIα subunit, compared to the peptide of SEQ ID NOs:1 or 2, wherein the peptide is selected from the group consisting of:

```
VQGNTDEAQEEFAWKIAKMIVSD[I/V]MQQ;      (SEQ ID NO:51)

VQGNTDEAQEELAWKIAKMIISD[I/V]MQQ; and  (SEQ ID NO:52)

VQGNTDEAQEELAWKIAKMILSD[I/V]MQQ.      (SEQ ID NO:53)
```

16. A peptide that binds to the PKA-RIα subunit but has substantially no ability to bind to the PKA-RIIα subunit, compared to the peptide of SEQ ID NOs:1 or 2, wherein the peptide is

```
VQGNTDEAQEELAWKIAKMIWSD[I/V]MQQ    (SEQ ID NO:54)
```

17. The mutein of claim 1, wherein said mutein is

```
FEELAWKIAKMIISDVFQQC.    (SEQ ID NO:107; PV-49)
```

* * * * *